United States Patent
Doronina et al.

(10) Patent No.: US 7,750,116 B1
(45) Date of Patent: Jul. 6, 2010

(54) ANTIBODY DRUG CONJUGATE METABOLITES

(75) Inventors: Svetlana O. Doronina, Snohomish, WA (US); Stephen C. Alley, Seattle, WA (US)

(73) Assignee: Seattle Genetics, Inc., Bothell, WA (US)

( * ) Notice: Subject to any disclaimer, the term of this patent is extended or adjusted under 35 U.S.C. 154(b) by 190 days.

(21) Appl. No.: 11/677,029

(22) Filed: Feb. 20, 2007

Related U.S. Application Data

(60) Provisional application No. 60/774,446, filed on Feb. 18, 2006.

(51) Int. Cl.
*C07K 5/00* (2006.01)

(52) U.S. Cl. .......................................... 530/330; 514/17

(58) Field of Classification Search ........................ None
See application file for complete search history.

(56) References Cited

U.S. PATENT DOCUMENTS

| | | | |
|---|---|---|---|
| 4,753,894 A | 6/1988 | Frankel et al. | |
| 4,816,397 A | 3/1989 | Boss et al. | |
| 4,816,567 A | 3/1989 | Cabilly et al. | |
| 4,943,628 A | 7/1990 | Rosen et al. | |
| 4,978,744 A | 12/1990 | Petit et al. | |
| 5,169,774 A | 12/1992 | Frankel et al. | |
| 5,225,539 A | 7/1993 | Winter | |
| 5,286,637 A | 2/1994 | Veronese et al. | |
| 5,410,024 A | 4/1995 | Petit et al. | |
| 5,545,806 A | 8/1996 | Lonberg et al. | |
| 5,569,825 A | 10/1996 | Lonberg et al. | |
| 5,625,126 A | 4/1997 | Lonberg et al. | |
| 5,629,197 A | 5/1997 | Ring et al. | |
| 5,633,425 A | 5/1997 | Lonberg et al. | |
| 5,635,483 A | 6/1997 | Pettit et al. | |
| 5,654,399 A | 8/1997 | Sakakibara et al. | |
| 5,661,016 A | 8/1997 | Lonberg et al. | |
| 5,767,237 A | 6/1998 | Sakakibara et al. | |
| 5,780,588 A | 7/1998 | Pettit et al. | |
| 5,821,337 A | 10/1998 | Carter et al. | |
| 5,840,699 A | 11/1998 | Sakakibara et al. | |
| 6,004,934 A | 12/1999 | Sakakibara et al. | |
| 6,048,720 A | 4/2000 | Dalborg et al. | |
| 6,054,297 A | 4/2000 | Carter et al. | |
| 6,054,561 A | 4/2000 | Ring | |
| 6,124,431 A | 9/2000 | Sakakibara et al. | |
| 6,214,345 B1 * | 4/2001 | Firestone et al. ......... | 424/178.1 |
| 6,407,213 B1 | 6/2002 | Carter et al. | |
| 6,569,834 B1 | 5/2003 | Pettit et al. | |
| 6,620,911 B1 | 9/2003 | Petit et al. | |
| 6,639,055 B1 | 10/2003 | Carter et al. | |
| 6,884,869 B2 | 4/2005 | Senter et al. | |
| 2002/0001587 A1 | 1/2002 | Erickson et al. | |
| 2003/0096743 A1 | 5/2003 | Senter et al. | |
| 2003/0130189 A1 | 7/2003 | Senter et al. | |
| 2004/0018194 A1 | 1/2004 | Francisco et al. | |
| 2004/0235068 A1 | 11/2004 | Levinson | |
| 2005/0106644 A1 | 5/2005 | Cairns et al. | |
| 2005/0107595 A1 | 5/2005 | Cairns et al. | |
| 2005/0232929 A1 | 10/2005 | Kadkhodayan et al. | |
| 2005/0238649 A1 * | 10/2005 | Doronina et al. ......... | 424/178.1 |
| 2005/0238650 A1 | 10/2005 | Crowley et al. | |
| 2005/0256030 A1 | 11/2005 | Feng | |
| 2006/0073152 A1 | 4/2006 | Dennis | |
| 2006/0182751 A1 | 8/2006 | Gazzard et al. | |
| 2006/0233794 A1 | 10/2006 | Law et al. | |
| 2007/0092520 A1 | 4/2007 | Dennis et al. | |
| 2007/0134243 A1 | 6/2007 | Gazzard et al. | |
| 2007/0212356 A1 | 9/2007 | Chen et al. | |

FOREIGN PATENT DOCUMENTS

| | | |
|---|---|---|
| CA | 2114156 A1 | 7/1994 |
| JP | 06-234790 A | 8/1994 |
| JP | 09-77791 A | 3/1997 |
| WO | WO 99/35164 A1 | 7/1999 |
| WO | WO 01/18032 A2 | 3/2001 |
| WO | WO 02/088172 A2 | 11/2002 |
| WO | WO 03/008378 A1 | 1/2003 |
| WO | WO 03/034903 A2 | 5/2003 |
| WO | WO 03/043583 A2 | 5/2003 |
| WO | WO 2004/032828 A2 | 4/2004 |
| WO | WO 2006/034488 A3 | 3/2006 |
| WO | WO 2006/083936 A3 | 8/2006 |
| WO | WO 2007/001851 A3 | 1/2007 |
| WO | WO 2007/109567 A1 | 9/2007 |

OTHER PUBLICATIONS

Alley et al., "Controlling the location of drug attachment in antibody-drug conjugates," *Proceedings of the AACR*, vol. 45, abstract # 627 (2004).

Afar et al., "Preclinical validation of anti-TMEFF2-auristatin E-conjugated antibodies in the treatment of prostate cancer," *Molecular Cancer Therapeutics*, 3(8):921-932 (2004).

Bhaskar et al., "E-Selectin Up-Regulation Allows for Targeted Drug Delivery in Prostate Cancer," *Cancer Research*, 63:6387-6394 (2003).

Carter, "Improving the Efficacy of Antibody-Based Cancer Therapies," *Nature Reviews* 1:118-129 (2001).

Dillman, "Monoclonal Antibodies for Treating Cancer," *Annals of Internal Medicine* 111:592-603 (1989).

Doronina et al., "Development of potent monoclonal antibody auristatin conjugates for cancer therapy," *Nature Biotechnology*, 21(7):778-784 (2003) + Erratum *Nature Biotechnology*, 21(8):941 (2003).

(Continued)

*Primary Examiner*—Sheela J Huff

(57) ABSTRACT

Methods of treating a refractory or drug resistant cancer, cell proliferative disorder and tumor cells are provided. Also provided are antibody drug conjugate metabolites.

1 Claim, 4 Drawing Sheets

OTHER PUBLICATIONS

Doronina et al., "Immunoconjugates comprised of drugs with impaired cellular permeability: A new approach to targeted therapy," SciFinder search result, abstract of paper from 228th ACS National Meeting held in Philadelphia, PA, Aug. 22-26, 2004.

Doronina et al., "Enhanced Activity of Monomethylauristatin F through Monoclonal Antibody Delivery: Effects of Linker Technology on Efficacy and Toxicity," *Bioconjugate Chem.*, 17:114-124 (2006).

Emery et al., "Humanized monoclonal antibodies for therapeutic applications," *Exp. Opin. Invest. Drugs* 3(3):241-251 (1994).

Francisco et al., "cAC10-vcMMAE, an anti-CD30-monomethyl auristatin E conjugate with potent and selective antitumor activity," *Blood*, 102(4):1458-1465 (2003).

Gaertner and Offord, "Site-specific attachment of functionalized poly(ethylene glycol) to the amino terminus of proteins." *Bioconj. Chem.*, 7(1):38-44, 1996.

Genet, J. P., "Recent studies on asymmetric hydrogenation. New catalysts and synthetic applications in organic synthesis," *Pure Appl. Chem.*, 74(1):77-83 (2002).

Hamblett et al., "Effect of drug loading on the pharmacology, pharmacokinetics, and toxicity of an anti-CD30 antibody-drug conjugate," *Proceedings of the AACR*, vol. 45, abstract # 624 (2004).

Inada et al., "Modification of proteins with polyethylene glycol derivatives." *Methods Enzymol.*, 242:65-90, 1994.

Kline et al., "Novel Antitumor Prodrugs Designed for Activation by Matrix Metalloproteinases-2 and -9," *Molecular Pharmaceutics*, 1(1):9-22 (2004).

Klussman et al., "Secondary mAb—vcMMAE conjugates are highly sensitive reporters of antibody internalization via the lysosome pathway," *Bioconjug Chem.*, 15(4):765-773 (2004).

Law et al., "CD70 is expressed on renal cell carcinoma and is a potential target for tumor cell elimination by antibody-drug conjugates," *Proceedings of the AACR*, vol. 45, abstract # 625 (2004).

Mao et al., "EphB2 as a Therapeutic Antibody Drug Target for the Treatment of Colorectal Cancer," *Cancer Research*, 64:781-788 (2004).

Meyer et al., "Recent Advances in Antibody Drug Conjugates for Cancer Therapy," *Annual Reports in Medical Chemistry*, 38(chapter 23):229-237 (2003).

Miyazaki et al., "Synthesis and Antitumor Activity of Novel Dolastatin 10 Analogs," *Chem. Pharm. Bull.*, 43(10):1706-1718 (1995).

Natsume et al., "Characterization of the Interaction of TZT-1027, a Potent Antitumor Agent, with Tubulin," *Jpn. J. Cancer*, 91:737-747 (2000).

Petit et al., "Antineoplastic agents 337. Synthesis of dolastatin 10 structural modifications," *Anti-Cancer Drug Design*, 10:529-544 (1995).

Petit et al., "Specific Activities of Dolastatin 10 and Peptide Derivatives against *Cryptococcus neoformans*," *Antimicrobial Agents and Chemotherapy*, 42(11):2961-2965 (1998).

Petit et al., "A Cobalt—Phosphine Complex Directed Reformatsky Approach to a Stereospecific Synthesis of the Dolastatin 10 Unit Dolaproine (Dap)[1]," *J. Org. Chem.*, 66:8640-8642 (2001).

Pettit et al., "The Absolute Configuration and Synthesis of Natural (−) - Dolastatin 10," *J. Am. Chem. Soc.*, 111:5463-5465 (1989).

Pettit et al., "Dolastatins 24. Synthesis of (−) -dolastatin 10. X-Ray molecular structure of *N,N*-dimethylvalyl-valyl-dolaisoleuine *tert*-butyl ester," *J. Chem. Soc. Perkin Trans.1*, 5:859-863 (1996).

Pettit et al., "Antineoplastic agents 365. Dolastatin 10 SAR probes," *Anticancer Drug Des.*, 13(4):243-277 (1998).

Press Release, "Seattle Genetics, Inc. (SGEN) to Present Advances In Preclinical Research At American Cancer Research Annual Meeting," Mar. 24, 2004, downloaded from internet on Aug. 31, 2004.

Schoffski et al., "Phase I and pharmacokinetic study of TZT-1027, a novel synthetic dolastatin 10 derivative, administered as a 1-hour intravenous infusion every 3 weeks in patients with advanced refractory cancer," *Annals of Oncology*, 15:671-679 (2004).

Senter et al., "Immunoconjugates comprised of drugs with impaired cellular permeability: A new approach to targeted therapy," *Proceedings of the AACR*, vol. 45, abstract # 623 (2004).

Thornber, "Isosterism and Molecular Modification in Drug Design." *Chem. Soc. Rev.*, 8(4):563-580, 1979.

Toki et al., "Protease-Mediated Fragmentation of *p*-Amidobenzyl Ethers: A New Strategy for the Activation of Anticancer Prodrugs," *J. Org. Chem.*, 67:1866-1872 (2002).

Vippagunta et al., "Crystalline Solids." *Adv. Drug Delivery Rev.*, 48:3-26, 2001.

Woyke et al., "In Vitro Activities and Postantifungal Effects of the Potent Dolastatin 10 Derivative Auristatin PHE," *Antimicrobial Agents and Chemotherapy*, 45(12):3580-3584 (2001).

Woyke et al., "Effect of auristatin PHE on microtube integrity and nuclear localization in Cryptococcus neoformans," *Antimicrobial Agents and Chemotherapy*, 46(12):3802-3808 (2003).

International Search Report of Oct. 2, 2006 for PCT application PCT/US04/38392.

Written Opinion of Oct. 2, 2006 for PCT application PCT/US04/38392.

Doronina et al., "Novel Linkers for Monoclonal Antibody-Mediated Delivery of Cell Impermeable Anticancer Agents", poster presentation at AACR-NCI-EORTC International Conference on Molecular Targets and Cancer Therapeutics; Nov. 2005.

Doronina et al., "Novel Linkers for Monoclonal Antibody-Mediated Delivery of Anticancer Agents", poster presentation at annual meeting of the American Association for Cancer Research, Apr. 16-20, 2005, Anaheim, California.

\* cited by examiner

ANTIBODY DRUG CONJUGATE METABOLITES

CROSS-REFERENCES TO RELATED APPLICATIONS

This application claims the benefit of U.S. Provisional Patent Application No. 60/774,446, filed Feb. 18, 2006, which is incorporated by reference herein in its entirety.

REFERENCE TO A SEQUENCE LISTING

This application includes a sequence listing as a text file, named 1000-00911US_ST25 created Jun. 1, 2009. The material contained in this text file is incorporated by reference in its entirety for all purposes.

BACKGROUND OF THE INVENTION

Among the barriers to successful cancer therapy is the development of drug resistance by tumors. Drug resistance can be mediated by many mechanisms. Of the cell-based mechanisms, ATP-driven xenobiotic efflux of drugs is mediated by P-glycoprotein (also referred to herein as "P-gp"), the product of the mdr1 gene. P-gp is found on a variety of normal tissues, including endothelium and biliary duct cells. P-gp is a member of a large family of ATP-binding cassette proteins, many of which are responsible for removal of toxic substances to the extracellular space.

P-gp recognizes and removes molecules which share characteristics including hydrophobic structures and large ring systems. Many drugs used in the treatment of cancer are P-gp substrates. Thus, one mechanism of cell-based resistance is drug export by P-gp. Such resistance can be conferred by mutation of P-gp to increase the affinity of P-gp for the drug molecule, by increasing the rate of transporter function, and/or by increasing the number of P-gp transporters per cell. The latter mechanism is most often mediated by gene amplification. To overcome P-gp mediated resistance, inhibitors of P-gp can be used. However, the efficacy of such inhibitors can be limited due to mutation of the P-gp transporter and/or gene amplification resulting in increased wild-type or mutant P-gp transporters at the cell surface. Administration of P-gp inhibitors also can be associated with toxicity in patients.

Therefore, the development of drugs that can circumvent P-gp-mediated drug resistance could have significant clinical benefit.

BRIEF SUMMARY OF THE INVENTION

The present invention provides methods of treating a patient that has a drug resistant cancer, such as a tumor, hematologic disease or cell proliferative disorder. In one aspect, a method is provided for treating drug-resistant cancer cells in a patient in need of such treatment. The method includes evaluating whether the patient has a drug-resistant cancer, and if the patient has a drug-resistant cancer, administering to the patient an effective amount of a Drug-Linker-Ligand conjugate of the formula:

$$L-(LU-D)_p \qquad I$$

or a pharmaceutically acceptable salt or solvate thereof wherein,

L- is a Ligand unit;

LU is a Linker unit;

p is an integer from 1 to about 20; and

-D is a Drug unit.

The patient can be monitored to determine the status of the cancer following administration of the Drug-Linker-Ligand conjugate. In some embodiments, the Drug unit is MMAF or a cytotoxic derivative thereof, wherein the Drug unit kills or inhibits the proliferation of the cancer cells.

The Ligand unit can be an antibody or a non-antibody molecule. Suitable antibodies include, for example, monoclonal antibodies, such as chimeric, humanized or human antibodies or an antigen-binding fragment thereof. In some embodiments, the Ligand unit comprises an antigen-binding region that binds to a target antigen. In some embodiments, the Ligand unit is an antibody or antibody fragment such as AC10, BR96, 1F6 or 2F2. In some embodiments, the Ligand unit is a humanized or chimeric derivative of an antibody such as AC10, BR96, 1F6 or 2F2. In some embodiments, the Ligand unit is a growth inhibitory antibody.

In some embodiments, the Drug-Linker-Ligand conjugate induces cell death. In some embodiments, the Drug-Linker-Ligand conjugate induces apoptosis.

In some embodiments, about 2 to about 8 Linker-Drug units are conjugated to the Ligand unit. In other embodiments, 2 to 6 or 2 to 4 Linker-Drug units are conjugated to the Ligand unit.

In some embodiments, the Linker unit has the formula:

$$-A_a-W_w-Y_y-$$

wherein:

-A- is a Stretcher unit;

a is 0 or 1;

each —W— is independently an Amino Acid unit;

w is independently an integer ranging from 0 to 12;

—Y— is a Spacer unit; and y is 0, 1 or 2.

The number of Amino Acid units, w, can be, for example, 2, 3, 4, 5, 6, 7, 8, 9, 10, 11 or 12, and the like. In one group of embodiments w is 2.

$W_w$ can be, for example, valine citrulline, 5-aminovaleric acid, homo phenylalanine lysine, tetraisoquinolinecarboxylate lysine, cyclohexylalanine lysine, isonepecotic acid lysine, beta-alanine lysine, glycine serine valine glutamine, or isonepecotic acid.

In some embodiments, the Drug-Linker-Ligand conjugate has the formula selected from the group consisting of:

$$L - \left( \left[ \begin{array}{c} O \\ \diagup \\ N-R^{17}-[C(R^{24})_2]_t \\ \diagdown \\ O \end{array} \right]_a - W_w - Y_y - D \right)_p,$$

-continued

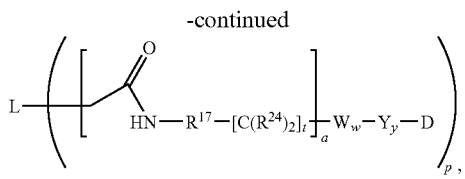

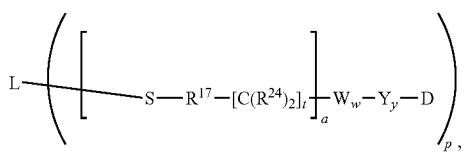

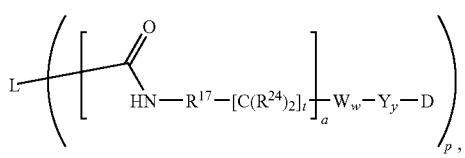

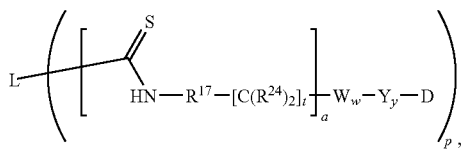

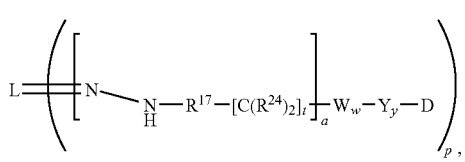

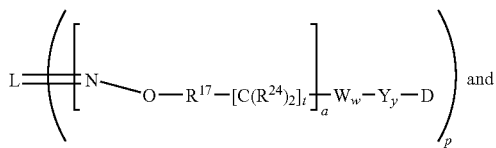 and

-continued

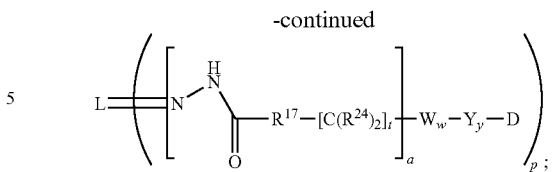

wherein L is an antibody or antibody fragment; $R^{17}$ is selected from the group consisting of $C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O$)$_r$—, or —($CH_2CH_2O$)$_r$—$CH_2$—; r is an integer ranging from 1 to 10; t is an integer of 0 to 1 and each $R^{24}$ is H or are combined to form =O.

In other embodiments, the Drug-Linker-Ligand conjugate has the formula:

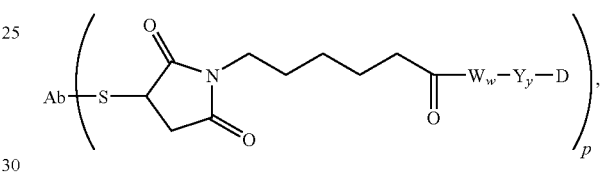

wherein Ab is an antibody or an antibody fragment, and S is a reactive thiol group of Ab.

In other embodiments, the Drug-Linker-Ligand conjugate has the formula:

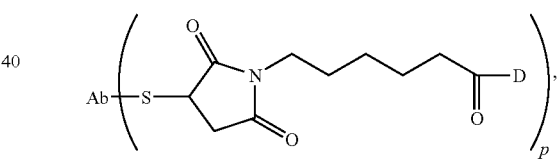

wherein Ab is an antibody or an antibody fragment, and S is a reactive thiol group of Ab.

In some embodiments, the Drug-Linker-Ligand conjugate has the formula:

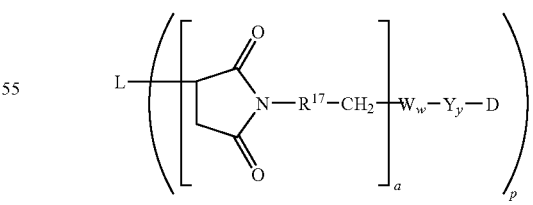

wherein L is an antibody or antibody fragment; $R^{17}$ is $C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-

$C_1$-$C_{10}$ alkylene-, —$(CH_2CH_2O)_r$—, or —$(CH_2CH_2O)_r$—$CH_2$—; and r is an integer ranging from 1 to 10.

In other embodiments, the Drug-Linker-Ligand conjugate has the formula:

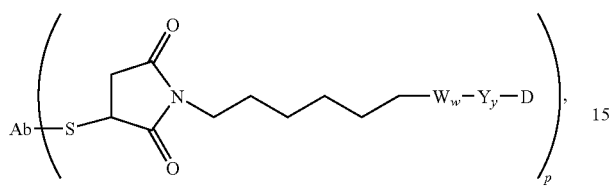

wherein Ab is an antibody or antibody fragment, and S is a reactive thiol group of Ab.

In other embodiments, the Drug-Linker-Ligand conjugate has the formula:

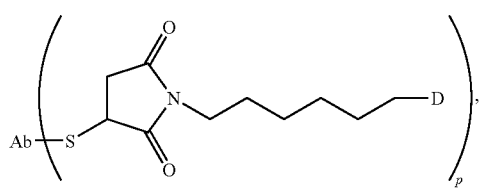

wherein Ab is an antibody or antibody fragment, and S is a reactive thiol group of Ab.

In some embodiments, the Drug-Linker-Ligand conjugate has the formula:

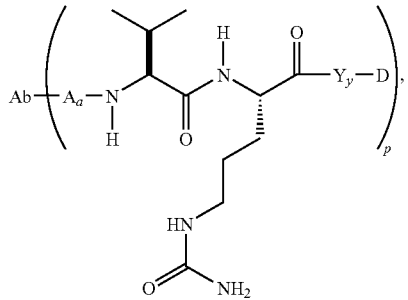

wherein Ab is an antibody or an, antibody fragment.

In some embodiments, the Drug-Linker-Ligand conjugate has the formula:

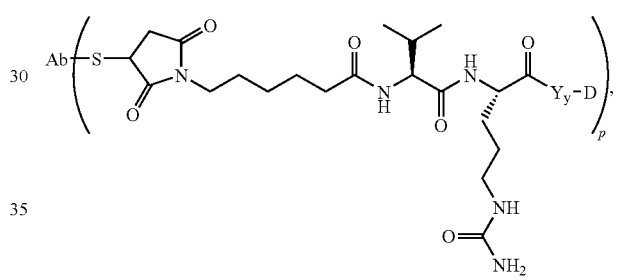

wherein Ab is an antibody or an antibody fragment, and S is a reactive thiol group of Ab.

In some embodiments, the Drug-Linker-Ligand conjugate has the formula:

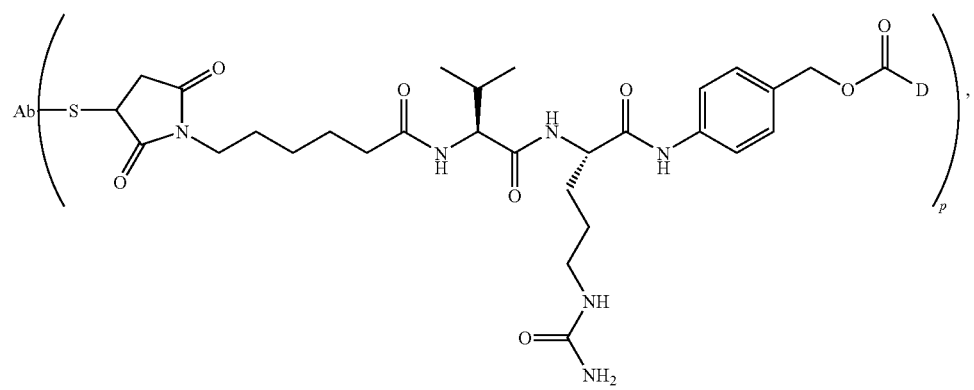

wherein Ab is an antibody or an antibody fragment, and S is a reactive thiol group of Ab.
In some embodiments, the Drug-Linker-Ligand conjugate has the formula:
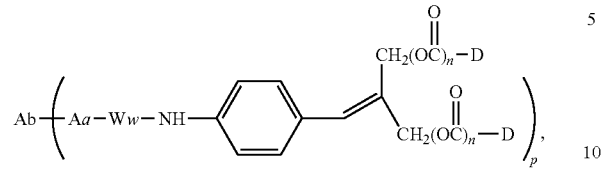
wherein Ab is an antibody or an antibody fragment.
In some embodiments, the Drug-Linker-Ligand conjugate has the formula:
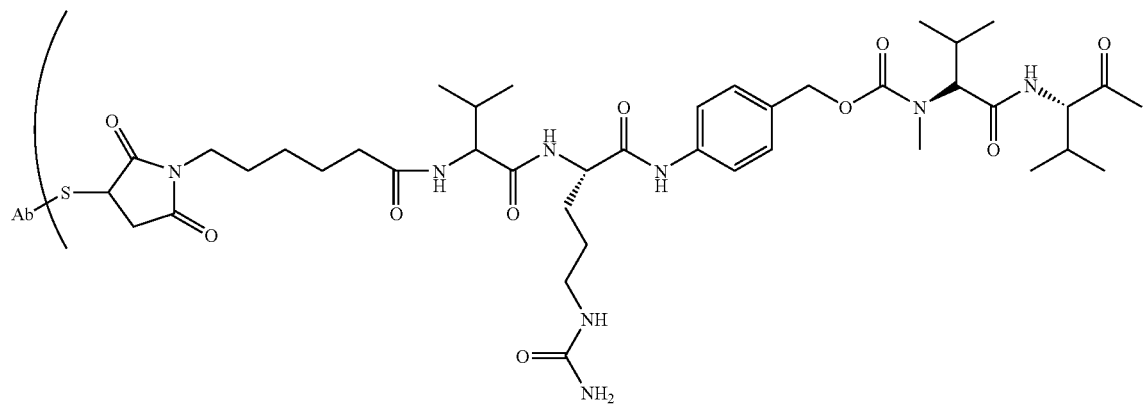
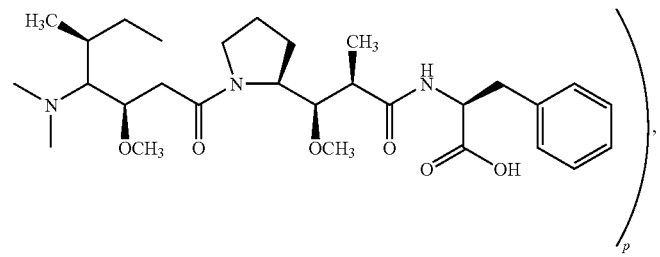

wherein Ab is an antibody or an antibody fragment, S is a reactive thiol group of Ab, and Val-Cit means valine citrulline.

In some embodiments, the Drug-Linker-Ligand conjugate has the formula:

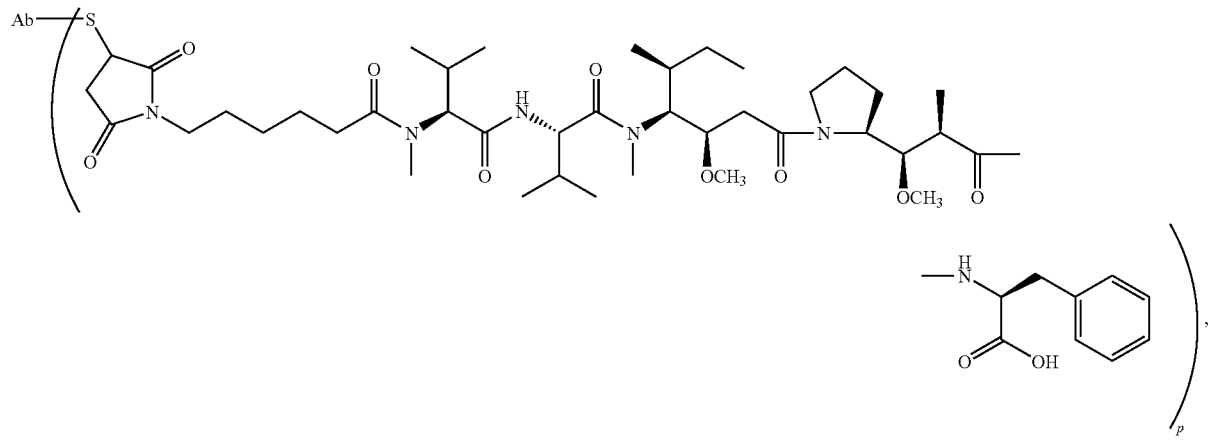

wherein Ab is an antibody or antibody fragment, and S is a reactive thiol group of Ab.

In some embodiments, a substantial amount of the Drug unit is not cleaved from the Drug-Linker-Ligand conjugate until the conjugate enters a cell with a cell-surface receptor specific for the Ligand unit, and the Drug unit is cleaved from the Ligand unit when the Drug-Linker-Ligand conjugate enters the cell. In some embodiments, a substantial amount of the Linker-Drug unit is not cleaved from the Drug-Linker-Ligand conjugate until the conjugate enters a cell with a cell-surface receptor specific for the Ligand unit, and the Linker-Drug unit is cleaved from the Ligand unit when the Drug-Linker-Ligand conjugate enters the cell.

In some embodiments, the bioavailability of the Drug unit or an intracellular metabolite of the Drug unit in a patient is improved when compared to an unconjugated Drug unit. In some embodiments, the bioavailability of the Linker-Drug unit or an intracellular metabolite of the Linker-Drug unit in a patient is improved when compared to an unconjugated Drug unit.

In some embodiments, the bioavailability of the Drug-Linker-Ligand conjugate or an intracellular metabolite of the Drug-Linker-Ligand conjugate in a mammal is improved when compared to an analog of the Drug-Linker-Ligand conjugate not having the Drug unit.

In some embodiments, the Drug-Linker-Ligand conjugate is administered as a pharmaceutical composition comprising an effective amount of the Drug-Linker-Ligand conjugate, or a pharmaceutically acceptable salt thereof, and a pharmaceutically acceptable diluent, carrier or excipient.

In some embodiments, another therapeutic agent, such as a chemotherapeutic agent, can also be administered to the patient. In some embodiments, the cancer is a solid tumor. In some embodiments, the cancer is a hematological cancer. In some embodiments, the cancer is a cell proliferative disorder. In some embodiments, the cancer is breast, ovarian, stomach, endometrial, salivary gland, lung, kidney, colon, colorectal, thyroid, pancreatic, prostate or bladder cancer. In some embodiments, cells of a cancer, a tumor or a cell proliferative disorder are contacted with a Drug-Linker-Ligand conjugate.

DEFINITIONS AND ABBREVIATIONS

Figure 1:
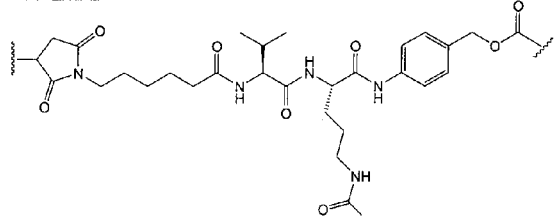
FIG. 1. Structures of drugs and linkers. In the left column are shown the linkers maleimidocaproyl-Val-Cit-PABC (L1), maleimidocaproyl-Val-Cit (L2), maleimidocaproyl-PABC (L3), and maleimidocaproyl (L4). In the right column are shown the drugs MMAF, and MMAF-OMe, and Doxorubicin.

Unless stated otherwise, the following terms and phrases as used herein are intended to have the following meanings:

The term "antibody" as used herein, refers to a full-length immunoglobulin molecule or an immunologically active portion of a full-length immunoglobulin molecule, i.e., a molecule that contains an antigen binding site that immunospecifically binds an antigen of a target of interest or part thereof, such targets including, but not limited to, drug resistant cells (e.g., cancer cells). The antibody disclosed herein can be of any class (e.g., IgG, IgE, IgM, IgD, and IgA), or subclass (e.g., IgG$_1$, IgG$_2$, IgG$_3$, IgG$_4$, IgA$_1$ and IgA$_2$) of immunoglobulin molecule. The antibody can be derived from any species. In one aspect, the antibody is of human, murine, or rabbit origin. In another aspect, the antibody is polyclonal, monoclonal, bispecific, multispecific, human, humanized or a chimeric antibody, or an epitope-binding fragment of any of the above which immunospecifically bind to a target antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site.

Monoclonal antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, that exhibit the desired biological activity (see, e.g., U.S. Pat. No. 4,816,567; Morrison et al., 1984, Proc. Natl. Acad. Sci. USA 81:6851-6855). For example, a chimeric antibody may be derived from the variable region from a mouse antibody and the constant region from a human antibody.

An "antibody fragment" refers to a portion of an intact antibody, typically comprising the antigen-binding or variable region thereof. Examples of antibody fragments include Fab, Fab', F(ab')$_2$, and Fv fragments; linear antibodies; single-chain antibody molecules; an scFv; an IgG ΔC$_H$2, a minibody, a diabody, a triabody, a tetrabody, a dsFv; an sc-Fv-Fc; an (scFv)$_2$; a fragment produced by a Fab expression library; an anti-idiotypic (anti-Id) antibody; and multispecific antibodies formed from antibody fragment(s).

An "intact" antibody is one which comprises an antigen-binding variable region as well as a light chain constant domain (CO and heavy chain constant domains, C$_H$1, C$_H$2 and C$_H$3. The constant domains may be native sequence constant domains (e.g., human native sequence constant domains) or amino acid sequence variants thereof.

The term "polypeptide" refers to a polymer of amino acids and its equivalent and does not refer to a specific length of a product; thus, "peptides" and "proteins" are included within the definition of a polypeptide. Also included within the definition of polypeptides are "antibodies" as defined herein. A "polypeptide region" refers to a segment of a polypeptide, which segment may contain, for example, one or more domains or motifs (e.g., a polypeptide region of an antibody can contain, for example, one or more CDRs). The term "fragment" refers to a portion of a polypeptide typically having at least 20 contiguous or at least 50 contiguous amino acids of the polypeptide. A "derivative" includes a polypeptide or fragment thereof having conservative amino acid substitutions relative to a second polypeptide; or a polypeptide or fragment thereof that is modified by covalent attachment of a second molecule such as, e.g., by attachment of a heterologous polypeptide, or by glycosylation, acetylation, phosphorylation, and the like. Further included within the definition of "polypeptide" is, for example, a polypeptide containing one or more analogs of an amino acid (e.g., unnatural amino acids and the like), polypeptides with unsubstituted linkages, as well as other modifications known in the art, both naturally and non-naturally occurring.

A "native sequence" polypeptide is one which has the same amino acid sequence as a polypeptide (e.g., a tumor-associated antigen) derived from nature. Such native sequence polypeptides can be isolated from nature or can be produced by recombinant or synthetic means. Thus, a native sequence polypeptide can have the amino acid sequence of naturally-occurring human polypeptide, murine polypeptide, or polypeptide from any other mammalian species.

The term "amino acid sequence variant" refers to a polypeptide having an amino acid sequence that differ to some extent from a native sequence polypeptide. Ordinarily, an amino acid sequence variant will possess at least about 70% homology with at least one domain of a native polypeptide, or with at least one domain of a native protein, and preferably, it will be at least about 80%, more preferably, at least about 90% homologous with such protein or domain. The amino acid sequence variants possess substitutions, deletions, and/or insertions at certain positions within the amino acid sequence of the native amino acid sequence.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In certain embodiments, the two sequences are the same length.

The term "substantially identical," in the context of two nucleic acids or polypeptides, refers to two or more sequences or subsequences that have at least 50%, at least 55%, at least 60%, or at least 65% identity; typically at least 70% or at least 75% identity; more typically at least 80% or at least 85% identity; and even more typically at least 90%, at least 95%, or at least 98% identity (as determined using one of the methods set forth infra).

"Similarity" or "percent similarity" in the context of two or more polypeptide sequences, refer to two or more sequences or subsequences that have a specified percentage of amino acid residues that are the same or conservatively substituted when compared and aligned for maximum correspondence, as measured using one of the methods set forth infra. By way of example, a first amino acid sequence can be considered similar to a second amino acid sequence when the first amino acid sequence is at least 50%, 60%, 70%, 75%, 80%, 90%, or even 95% identical, or conservatively substituted, to the second amino acid sequence when compared to an equal number of amino acids as the number contained in the first sequence, or when compared to an alignment of polypeptides that has been aligned by a computer similarity program known in the art (see infra).

The terms "substantial similarity" or "substantially similar," in the context of polypeptide sequences, indicates that a polypeptide region has a sequence with at least 70%, typically at least 80%, more typically at least 85%, and even more typically at least 90% or at least 95% sequence similarity to a reference sequence. For example, a polypeptide is substantially similar to a second polypeptide, for example, where the two peptides differ by one or more conservative substitutions.

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to identify amino acid sequences homologous to a protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. (See, e.g., National Center for Biotechnology Information (NCBI) website.) Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see, e.g., NCBI website.

Alternatively, protein sequence alignment may be carried out using the CLUSTAL W algorithm, as described by Higgins et al., 1996, Methods Enzymol. 266:383-402.

The term "diabodies" refers to small antibody fragments with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., 1993, Proc. Natl. Acad. Sci. USA 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., 1986, Nature 321:522-525; Riechmann et al., 1988, Nature 332:323-329; and Presta, 1992, Curr. Op. Struct. Biol. 2:593-596.

An "isolated molecule" (e.g., an antibody) is one which has been identified and separated and/or recovered from a component of its natural environment. Contaminant components of its natural environment are materials which would interfere with diagnostic or therapeutic uses for the molecule, and may include enzymes, hormones, and other proteinaceous or non-proteinaceous solutes. In some embodiments, the molecule will be purified (1) to greater than 95% by weight of molecule as determined by the Lowry method, or to more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. An "isolated molecule" (e.g., an antibody) includes the molecule in situ within recombinant cells since at least one component of the molecules's natural environment will not be present. Ordinarily, however, an isolated molecule will be prepared by at least one purification step.

The term "effective amount" refers to an amount of a drug or therapeutic agent (e.g., a Drug-Linker-Ligand conjugate) effective to treat (e.g., kill) a cancer cell in a mammal. In the case of cancer, the effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic.

The term "therapeutically effective amount" refers to an amount of a drug (e.g., a Drug-Linker-Ligand conjugate) effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The term "cytotoxic activity" refers to a cell-killing, cytostatic or anti-proliferation effect of a Drug-Linker-Ligand or Drug-Linker conjugate or an intracellular metabolite of such a compound. Cytotoxic activity may be expressed as the $IC_{50}$ value which is the concentration (molar or mass) per unit volume at which half the cells survive.

The terms "cancer" and "cancerous" refer to or describe the physiological condition in mammals that is typically characterized by unregulated cell growth.

The terms "cell proliferative disorder" and "proliferative disorder" refer to disorders that are associated with some degree of abnormal cell proliferation.

The term "tumor" refers to all neoplastic cell growth and proliferation, whether malignant or benign, and all pre-cancerous and cancerous cells and tissues.

A "chemotherapeutic agent" is a chemical compound useful in the treatment of cancer.

The term "prodrug" as used herein refers to a precursor or derivative form of a pharmaceutically active substance that is less cytotoxic to tumor cells compared to the parent drug and is capable of being enzymatically or hydrolytically activated or converted into the more active parent form. See, e.g., Wilman, "Prodrugs in Cancer Chemotherapy," Biochemical Society Transactions, 14, pp. 375-382, 615th Meeting Belfast (1986); and Stella et al., "Prodrugs: A Chemical Approach to Targeted Drug Delivery," Directed Drug Delivery, Borchardt et al., (ed.), pp. 247-267, Humana Press (1985).

The term "package insert" is used to refer to instructions customarily included in commercial packages of therapeutic products that contain information about the indications, usage, dosage, administration, contraindications and/or warnings concerning the use of such therapeutic products.

An "isolated nucleic acid molecule" is a nucleic acid molecule that is identified and separated from at least one other nucleic acid molecule with which it is ordinarily associated in its naturally occurring state; e.g., a natural cell. Thus, an isolated nucleic acid molecule is other than in the form or setting in which it is found in nature. However, an isolated nucleic acid molecule includes a nucleic acid molecule contained in a cell where, for example, the nucleic acid molecule is in a chromosomal location that differs from its location in the natural cell.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA encoding a polypeptide where the polypeptide is expressed as a preprotein that participates in the secretion of the polypeptide. A promoter or enhancer is operably linked to a coding sequence if it affects the transcription of the sequence. A ribosome binding site is operably linked to a coding sequence if it is positioned so as to facilitate translation. Generally, "operably linked" means that the nucleic acid sequences being linked are contiguous, and, in the case of a secretory leader, contiguous and in reading phase. However, enhancers do not have to be contiguous to be operably linked. Linking can be accomplished by ligation at convenient restriction sites. If such sites do not exist, the synthetic oligonucleotide adaptors or linkers can be used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "alkyl" refers to a $C_1$-$C_{18}$ hydrocarbon containing normal, secondary, tertiary or cyclic carbon atoms. Examples include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), and 3,3-dimethyl-2-butyl (—$CH(CH_3)C(CH_3)_3$).

The term "alkenyl" refers to a $C_2$-$C_{18}$ hydrocarbon containing normal, secondary, tertiary or cyclic carbon atoms with at least one site of unsaturation, i.e., a carbon-carbon, $sp^2$ double bond. Examples include, but are not limited to: ethylene or vinyl (—$CH$=$CH_2$), allyl (—$CH_2CH$=$CH_2$), cyclopentenyl (-$C_5H_7$), and 5-hexenyl (—$CH_2CH_2CH_2CH_2CH$=$CH_2$).

The term "alkynyl" refers to a $C_2$-$C_{18}$ hydrocarbon containing normal, secondary, tertiary or cyclic carbon atoms with at least one site of unsaturation, i.e., a carbon-carbon, sp triple bond. Examples include, but are not limited to: acetylenic (—C≡CH) and propargyl (—$CH_2$C≡CH).

The term "alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—), 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like. A "C$_1$-C$_{10}$ alkylene" is a straight chain, saturated hydrocarbon group of the formula —(CH$_2$)$_{1-10}$—. Examples of a C$_1$-C$_{10}$ alkylene include methylene, ethylene, propylene, butylene, pentylene, hexylene, heptylene, octylene, nonylene and decalene.

The term "alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

The term "alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH$_2$C≡C—), and 4-pentynyl (—CH$_2$CH$_2$CH$_2$C≡CH—).

The term "aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —C$_1$-C$_{10}$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$, —NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_{10}$ alkyl and aryl.

The term "arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

The term "heteroarylalkyl" refers to an acyclic alkyl radical in which one of the hydrogen atoms bonded to a carbon atom, typically a terminal or sp$^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g., the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl, respectively, in which one or more hydrogen atoms are each independently replaced with a substituent. Typical substituents include, but are not limited to, —X, —R, —O$^-$, —OR, —SR, —S$^-$, —NR$_2$, —NR$_3$, ═NR, —CX$_3$, —CN, —OCN, —SCN, —N═C═O, —NCS, —NO, —NO$_2$, ═N$_2$, —N$_3$, NC(═O) R, —C(═O)R, —C(═O)NR$_2$, —SO$_3^-$, —SO$_3$H, —S(═O)$_2$ R, —OS(═O)$_2$OR, —S(═O)$_2$NR, —S(═O)R, —OP(═O)(OR)$_2$, —P(═O)(OR)$_2$, —PO$^-_3$, —PO$_3$H$_2$, —C(═O)R, —C(═O)X, —C(═S)R, —CO$_2$R, —CO$_2^-$, —C(═S)OR, —C(═O)SR, —C(═OS)SR, —C(═O)NR$_2$, —C(═S)NR$_2$, or —C(═NR)NR$_2$, where each X is independently a halogen: F, Cl, Br, or I; and each R is independently —H, C$_2$-C$_{18}$ alkyl, C$_6$-C$_{20}$ aryl, C$_3$-C$_{14}$ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g., nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include, by way of example and not limitation, pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

The term "$C_1$-$C_{10}$ alkyl," as used herein refers to a straight chain or branched, saturated or unsaturated hydrocarbon having from 1 to 8 carbon atoms. Representative "$C_1$-$C_{10}$) alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_{10}$ alkyls include, but are not limited to, -isopropyl, -sec-butyl, -isobutyl, -tert-butyl, -isopentyl, 2-methylbutyl, isohexyl, isohexyl, isooctyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl and 3-methylheptyl; unsaturated $C_{1-10}$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl and -3-methyl-1 butynyl. A $C_1$-$C_{10}$alkyl group can be unsubstituted or substituted with one or more groups including, but not limited to, —$C_1$-$C_{10}$ alkyl, —O—($C_1$-$C_{10}$ alkyl), -aryl, —C(O)R', —OC(O)R', —C(O)OR', —C(O)NH$_2$, —C(O)NHR', —C(O)N(R')$_2$, —NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —$C_1$-$C_{10}$ alkyl and aryl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

A "$C_1$-$C_{10}$ alkylene" is a straight chain, saturated hydrocarbon group of the formula —(CH$_2$)$_{1-10}$—. Examples of a $C_1$-$C_{10}$ alkylene include methylene, ethylene, propylene, butylene, pentylene, hexylene, heptylene, ocytylene, nonylene and decalene.

An "arylene" is an aryl group which has two covalent bonds and can be in the ortho, meta, or para configurations as shown in the following structures:

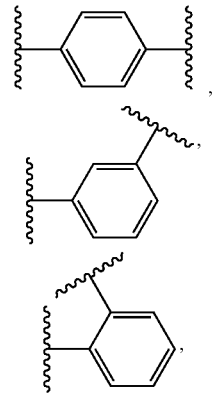

in which the phenyl group can be unsubstituted or substituted with up to four groups including, but not limited to, —$C_1$-$C_{10}$ alkyl, —O—($C_1$-$C_{10}$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_{10}$ alkyl and aryl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_{10}$ alkyl, —O—($C_1$-$C_{10}$ alkyl), -aryl, —C(O)R', —OC(O)R', —C(O)OR', —C(O)NH$_2$, —C(O)NHR', —C(O)N(R')$_2$, —NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_{10}$ alkyl and aryl.

"$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_{10}$ alkyl, —O—($C_1$-$C_{10}$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_{10}$ alkyl and aryl.

The phrase "pharmaceutically acceptable salt," as used herein, refers to a pharmaceutically acceptable organic or inorganic salt. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis -(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refers to an association of one or more solvent molecules and a compound. Examples of solvents that form pharmaceutically acceptable solvates include, but are not limited to, water, isopropanol, ethanol, methanol, DMSO, ethyl acetate, acetic acid, and ethanolamine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984), McGraw-Hill Book Company, New York; and Eliel, E. and Wilen, S., Stereochemistry of Organic Compounds (1994), John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Examples of a "patient" include, but are not limited to, a human, rat, mouse, guinea pig, monkey, pig, goat, cow, horse, dog, cat, bird and fowl. In an exemplary embodiment, the patient is a human.

The terms "treat" or "treatment," unless otherwise indicated by context, refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

In the context of cancer, the term "treating" includes any or all of: preventing growth or proliferation of tumor cells, cancer cells, or of a tumor; preventing replication of tumor cells or cancer cells, lessening of overall tumor burden or decreasing the number of cancerous cells, and ameliorating one or more symptoms associated with the disease.

The following cytotoxic drug abbreviations are used herein and have the indicated definitions: MMAF is N-methylvaline-valine-dolaisoleuine-dolaproline-phenylalanine (MW 731.5).

The following linker abbreviations are used herein and have the indicated definitions: Val Cit is a valine-citrulline, dipeptide site in protease cleavable linker; cit is citrulline; dap is dolaproine; dil is dolaisoleuine; phe is phenylalanine; val is valine; DTNB is 5,5'-dithiobis(2-nitrobenzoic acid); PAB is p-aminobenzylcarbamoyl; (Me)vc is N-methyl-valine citrulline, where the linker peptide bond has been modified to prevent its cleavage by cathepsin B; MC is maleimidocaproyl; MC(PEG)6-OH is maleimidocaproyl-polyethylene glycol; SPP is N-Succinimidyl 4-(2-pyridylthio) pentanoate; DIEA is NN-diisopropylethylamine; and SMCC is N-Succinimidyl 4-(N-maleimidomethyl) cyclohexane-1 carboxylate.

DETAILED DESCRIPTION OF THE INVENTION

The present invention provides methods of treating a patient that has a relapsed or refractory cancer, cell proliferative disorder or tumor. The invention is based on the surprising and unexpected discovery that certain auristatins are effective for treating drug resistant cancers, cell proliferative disorder and tumors. (Unless otherwise indicated by context, the term cancer, as used herein, refers to cancer, cell proliferative disorder or tumor. Similarly, cancer cells refer to cells of a cancer, cell proliferative disorder or tumor, unless otherwise indicated by context.) The auristatin derivatives accumulate in drug resistant cells. As used herein, a "drug resistant" or "refractory" cancer, cell proliferative disorder or tumor refers to a refractory cancer, cell proliferative disorder or tumor which cells exhibit reduced cytotoxicity to a drug that is a substrate for the MDR1 (P-glycoprotein or P-gp) transporter enzyme due to P-gp expression or overexpression, as compared to to a comparable, sensitive cells.

Also provided are methods of treating refractory cancer cells in a patient in need of such treatment (e.g., a mammal such as a human) by administering an effective amount of an auristatin. As used herein, "refractory" cancer cells and "drug resistant" cancer cells refer to cells that have elevated levels of P-gp transport enzymes on the cell surface, that are determined to express elevated levels of P-gp enzyme by standard methods, and/or that exhibit reduced cytotoxicity to drugs that are substrates for MDR1 (P-gp), as compared with equivalent cancer cells otherwise typically deemed sensitive to such drugs. Examples of refractory cancer cells which may be treated include, but are not limited to, adenocarcinoma cells derived from adrenal, kidney, liver, small intestine, and colon tissue; pancreatic cancer cells, carcinoid cells, chronic myelogenous leukemia cells in blast crisis, non-small cell lung carcinoma cells, neuroblastoma cells, pheochromocytoma cells, multiple myeloma cells, adult acute lymphocytic leukemia cells, adult acute nonlymphocytic leukemia cells, nodular poorly differentiated lymphoma cells, ocular melanoma cells, skin melanoma cells, uterine melanoma cells, breast cancer cells and ovarian cancer cells, and metastatic cells (see also infra).

In some embodiments, the auristatin derivative is MMAF (N-methylvaline-valine-dolaisoleuine-dolaproine-phenylalanine) or a derivative thereof. MMAF can be as potent against drug-resistant cell lines as against the parental strains. This difference in potency is due to the zwitterionic charge on MMAF. The charged nature of MMAF allows it to escape recognition and transport by the efflux transporter P-gp and allow it to remain in the cell. Therefore, MMAF and zwitterionic derivatives thereof accumulate to higher intracellular concentrations and result in cell death. In one aspect, the drug is not not a good substrate for P-gp. In another aspect, the drug is a poor substrate for P-gp.

In one aspect, a method of treating drug-resistant cancer cells is provided. In one embodiment, the method comprises administering to a patient an effective amount of MMAF or a derivative thereof to the patient having drug-resistant cancer cells. The drug is typically administered as a Drug-Linker-Ligand conjugate or a Drug-Linker conjugate. In some embodiments, the conjugate is an antibody or antibody fragment drug conjugate.

In another embodiment, the method includes (a) evaluating the patient to determine if the patient has a refractory or drug resistant cancer; (b) administering an effective amount of MMAF or a derivative thereof to the patient; and (c) monitoring the patient to determine the status of the cancer. The drug is typically administered as a Drug-Linker-Ligand conjugate or a Drug-Linker conjugate, such as an antibody drug conjugate.

In one aspect, a Drug-Linker-Ligand Conjugate is provided having Formula I:

or a pharmaceutically acceptable salt or solvate thereof wherein,

L- is a Ligand unit;
LU is a Linker unit;
p is an integer from 1 to about 20; and
-D is a Drug unit having the Formula $D_F$:

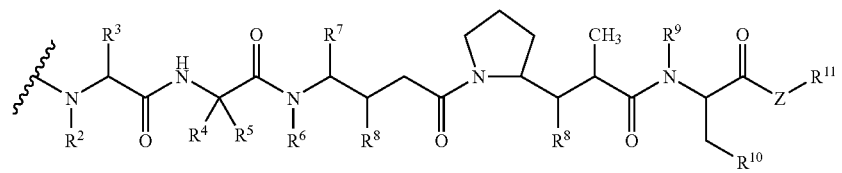

wherein, independently at each location:
$R^2$ is selected from H and $C_1$-$C_{10}$ alkyl;
$R^3$ is selected from H, $C_1$-$C_{10}$ alkyl, $C_3$-$C_8$ carbocycle, aryl, $C_1$-$C_{10}$ alkyl-aryl, $C_1$-$C_{10}$ alkyl-($C_3$-$C_8$ carbocycle), $C_3$-$C_8$ heterocycle and $C_1$-$C_{10}$ alkyl-($C_3$-$C_8$ heterocycle);
$R^4$ is selected from H, $C_1$-$C_{10}$ alkyl, $C_3$-$C_8$ carbocycle, aryl, $C_1$-$C_{10}$ alkyl-aryl, $C_1$-$C_{10}$ alkyl-($C_3$-$C_8$ carbocycle), $C_3$-$C_8$ heterocycle and $C_1$-$C_{10}$ alkyl-($C_3$-$C_8$ heterocycle);
$R^5$ is selected from H and methyl;
or $R^4$ and $R^5$ jointly form a carbocyclic ring and have the formula $-(CR^aR^b)_n-$ wherein $R^a$ and $R^b$ are independently selected from H, $C_1$-$C_{10}$ alkyl and $C_3$-$C_8$ carbocycle and n1 is selected from 2, 3, 4, 5 and 6;
$R^6$ is selected from H and $C_1$-$C_{10}$ alkyl;
$R^7$ is selected from H, $C_1$-$C_{10}$ alkyl, $C_3$-$C_8$ carbocycle, aryl, $C_1$-$C_{10}$ alkyl-aryl, $C_1$-$C_{10}$ alkyl-($C_3$-$C_8$ carbocycle), $C_3$-$C_8$ heterocycle and $C_1$-$C_{10}$ alkyl-($C_3$-$C_8$ heterocycle);
each $R^8$ is independently selected from H, OH, $C_1$-$C_{10}$ alkyl, $C_3$-$C_8$ carbocycle and O—($C_1$-$C_{10}$ alkyl);
$R^9$ is selected from H and $C_1$-$C_{10}$ alkyl;
$R^{10}$ is selected from aryl and $C_3$-$C_8$ heterocycle;
Z is O;
$R^{11}$ is selected from H or Me
wherein the Linker unit can be present or absent.

In some embodiments, the Drug unit has a zwitterionic charge, or is metabolized inside the cell to form a zwitterionic compound.

In another aspect, a Drug-Linker-Ligand Conjugate is provided having Formula IIa:

or a pharmaceutically acceptable salt or solvate thereof,
wherein,
L- is a Ligand unit;
LU is a Linker unit;
p is an integer from 1 to about 20; and
-D is a Drug unit having the Formula

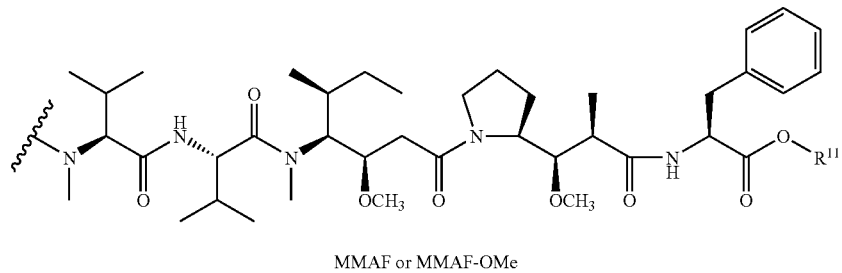

MMAF or MMAF-OMe wherein $R^{11}$=H or Me; and wherein the Linker unit can be present or absent.

In some embodiments, the Drug unit has a zwitterionic charge, or is metabolized inside the cell to form a zwitterionic compound.

In another aspect, a Drug-Linker-Ligand Conjugate is provided having Formula IIb:

or a pharmaceutically acceptable salt or solvate thereof, wherein,

L- is a Ligand unit;

LU is a Linker unit;

p is an integer from 1 to about 20; and

-D is a Drug unit having the Formula:

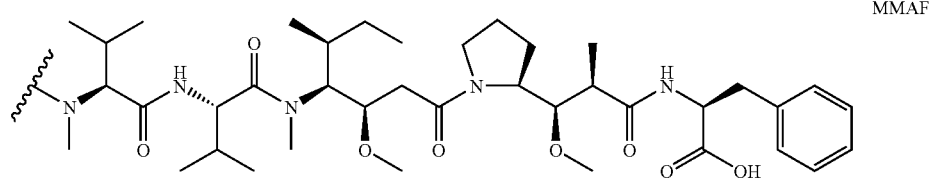

MMAF wherein the Linker unit can be present or absent.

In any of the above examples, the drug loading is represented by p, the average number of drug molecules per Ligand unit (e.g., an antibody drug conjugate or ADC). Drug loading may range from 1 to 20 drugs (D) per Ligand unit (e.g., an antibody). In some embodiments, p is 2, 4, 6 or 8. The average number of drugs per Ligand unit in preparation of conjugation reactions may be characterized by conventional means such as mass spectroscopy, ELISA assay, and HPLC. The quantitative distribution of a Drug-Linker-Ligand conjugate or a Drug-Linker conjugate in terms of p may also be determined. In some instances, separation, purification, and characterization of homogeneous Drug-Linker-Ligand conjugates or Drug-Linker conjugates, where p is a certain value from Drug-Linker-Ligand conjugates with other drug loadings, may be achieved by means such as reverse phase HPLC or electrophoresis.

For some Drug-Linker-Ligand conjugates, where the Ligand unit is an antibody or antibody fragment, p is determined by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In some embodiments, p is 2, 4, 6 or 8.

Typically, fewer than the theoretical maximum of drug moieties are conjugated to an antibody during a conjugation reaction. An antibody may contain, for example, many lysine residues that do not react with the drug-linker intermediate or linker reagent. Only the most reactive lysine groups may react with an amine-reactive linker reagent. Generally, antibodies do not contain many, if any, free and reactive cysteine thiol groups which may be linked to a drug moiety. Most cysteine thiol residues in the antibodies of the compounds of the invention exist as disulfide bridges (e.g., interchain or intrachain) and can be reduced with a reducing agent such as dithiothreitol (DTT). Additionally, the antibody can be subjected to denaturing conditions to reveal reactive nucleophilic groups such as lysine or cysteine. The loading (drug/antibody ratio) of an ADC' may be controlled in several different manners, including: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate, or linker reagent followed by drug moiety reagent, then the resulting product is a mixture of Drug-Linker-Ligand conjugates with a distribution of one or more drug moieties attached to a Ligand. The average number of drugs per antibody may be calculated from the mixture by dual ELISA antibody assay, specific for a Ligand and specific for the drug. Individual Drug-Linker-Ligand molecules may be identified in the mixture by mass spectroscopy, and separated by HPLC, e.g., hydrophobic interaction chromatography ("Effect of drug loading on the pharmacology, pharmacokinetics, and toxicity of an anti-CD30 antibody drug conjugate", Hamblett et al, Abstract No. 624, American Association for Cancer Research, 2004, Annual Meeting, Mar. 27-31, 2004, Proceedings of the AACR, Volume 45, March 2004; and "Controlling the Location of Drug Attachment in Antibody-Drug Conjugates", Alley et al, Abstract No. 627, American Association for Cancer Research; 2004 Annual Meeting, Mar. 27-31, 2004, Proceedings of the AACR, Volume 45, March 2004). Thus, a homogeneous Drug-Linker-Ligand conjugate with a single loading value may be isolated from the conjugation mixture by electrophoresis or chromatography.

The Ligand unit (L-) includes within its scope any unit of a Ligand (L) that binds or reactively associates or complexes with a receptor, antigen or other receptive moiety associated with a given target-cell population. In one aspect, the Ligand unit acts to deliver the Drug unit to the particular target cell population with which the Ligand unit reacts. Such Ligands include, but are not limited to, large molecular weight proteins such as, for example, full-length antibodies, antibody fragments, smaller molecular weight proteins, polypeptide or peptides, lectins, glycoproteins, non-peptides, vitamins, nutrient-transport molecules (such as, but not limited to, transferrin), or any other cell binding molecule or substance.

A Ligand unit can form a bond to a Linker unit (e.g., a Stretcher unit, an Amino Acid unit, and/or a Spacer Unit) or to a Drug Unit. For example, a Ligand unit can form a bond to a Linker unit via a heteroatom of the Ligand. Heteroatoms that may be present on a Ligand unit include, for example, sulfur (e.g., from a sulfhydryl group of a Ligand), oxygen (e.g., from a carbonyl, carboxyl or hydroxyl group of a Ligand) and nitrogen (e.g., from a primary or secondary amino group of a Ligand). These heteroatoms can be present on the Ligand in the Ligand's natural state, for example a naturally-occurring antibody, or can be introduced into the Ligand via chemical modification.

In one embodiment, a Ligand unit has a sulfhydryl group and the Ligand unit bonds to the Linker unit via the sulfhydryl group's sulfur atom.

In yet another aspect, the Ligand unit has one or more lysine residues that can be chemically modified to introduce one or more sulfhydryl groups. The Ligand unit bonds to the Linker unit via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the Ligand unit can have one or more carbohydrate groups that can be chemically modified to have one or more sulfhydryl groups. The Ligand unit bonds to the Linker Unit, such as a Stretcher Unit, via the sulfhydryl group's sulfur atom.

In yet another embodiment, the Ligand unit can have one or more carbohydrate groups that can be oxidized to provide an aldehyde (—CHO) group (see, e.g., Laguzza et al., 1989, J. Med. Chem. 32(3):548-55). The corresponding aldehyde can form a bond with a reactive site on a Stretcher. Reactive sites on a Stretcher that can react with a carbonyl group on a Ligand unit include, but are not limited to, hydrazine and hydroxylamine. Other protocols for the modification of proteins for the attachment or association of Drug units are described in Coligan et al., Current Protocols in Protein Science, vol. 2, John Wiley & Sons (2002), incorporated herein by reference.

In yet other embodiments, the Ligand unit can be linked to a Linker unit or a Drug unit at an amino and/or carboxy terminus.

Useful non-immunoreactive protein, polypeptide, or peptide Ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, lectins and apoprotein from low density lipoprotein.

In some embodiments, the Ligand unit is an antibody or antibody fragment. Useful polyclonal antibodies are heterogeneous populations of antibody molecules derived from the sera of immunized animals. Various procedures well known in the art may be used for the production of polyclonal antibodies to a target antigen (e.g., a cancer cell antigen, a protein, a peptide, a carbohydrate, a chemical, nucleic acid, or fragments thereof). For example, for the production of polyclonal antibodies, various host animals can be immunized by injection with an antigen of interest or derivative thereof, including, but not limited to, rabbits, mice, rats, and guinea pigs. Various adjuvants may be used to increase the immunological response, depending on the host species, including, but not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Useful monoclonal antibodies are homogeneous populations of antibodies to a particular antigenic determinant of a target antigen (e.g., a cancer cell antigen, a protein, a peptide, a carbohydrate, a chemical, nucleic acid, or fragments thereof). A monoclonal antibody (mAb) to a target antigen can be prepared by using any technique known in the art which provides for the production of antibody molecules by continuous cell lines in culture. These include, but are not limited to, the hybridoma technique originally described by Khler and Milstein (1975, Nature 256, 495-497), the human B cell hybridoma technique (Kozbor et al., 1983, Immunology Today 4: 72), and the EBV-hybridoma technique (Cole et al., 1985, Monoclonal Antibodies and Cancer Therapy, Alan R. Liss, Inc., pp. 77-96). Monoclonal antibodies also can be made by recombinant DNA methods (see, e.g., U.S. Pat. No. 4,816,567). Monoclonal antibodies may also be isolated from phage antibody libraries using the techniques described in Clackson et al. (1991, Nature 352:624-628) and Marks et al. (1991, J. Mol. Biol. 222:581-597), for example. The antibodies may be of any immunoglobulin class, including IgG, IgM, IgE, IgA, and IgD, and any subclass thereof. The hybridoma producing the mAbs of use in this invention may be cultivated in vitro or in vivo.

Useful monoclonal antibodies include, but are not limited to, human monoclonal antibodies, humanized monoclonal antibodies, antibody fragments, or chimeric (e.g., human-mouse or other species) monoclonal antibodies. Human monoclonal antibodies may be made by any of numerous techniques known in the art (see, e.g., Teng et al., 1983, Proc. Natl. Acad. Sci. USA 80, 7308-7312; Kozbor et al., 1983, Immunology Today 4, 72-79; and Olsson et al., 1982, Meth. Enzymol. 92, 3-16).

The antibody can also be a multispecific antibody, such as a bispecific antibody. Methods for making bispecific antibodies are known in the art. Traditional production of full-length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules. Procedures are disclosed in International Publication No. WO 93/08829, and in Traunecker et al., EMBO J. 10:3655-3659 (1991).

According to a different approach, antibody variable domains with the desired binding specificities (antibody-antigen combining sites) are fused to an immunoglobulin constant domain sequence(s). The fusion can be with one or more immunoglobulin heavy chain constant domains (e.g., hinge, $C_H1$, $C_H2$, $C_H3$, and/or $C_H4$ regions), or at least part of the hinge, $C_H2$, $C_H3$, and/or $C_H4$ regions. In some embodiments, the first heavy-chain constant region ($C_H1$) containing the site necessary for light chain binding is present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In an embodiment of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in one half of the bispecific molecule provides for a facile way of separation (e.g., International Publication No. WO 94/04690; which is incorporated herein by reference in its entirety).

For further details for generating bispecific antibodies see, for example, Suresh et al., 1986, Methods in Enzymology 121:210; Rodrigues et al., 1993, J. Immunology 151:6954-6961; Carter et al., 1992, Bio/Technology 10:163-167; Carter et al., 1995, J. Hematotherapy 4:463-470; and Merchant et al., 1998, Nature Biotechnology 16:677-681. Using such techniques, bispecific antibodies can be prepared for use in the treatment or prevention of disease as defined herein.

Bifunctional antibodies are also described in European Patent Publication No. EP 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. EP 0 217 577, both of which are incorporated herein by reference in their entirety.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as those having a variable region derived from a murine monoclonal and human immunoglobulin constant regions. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 173 494; International Publication No. WO 86/01533; U.S. Pat. No. 4,816,567; European Patent Publication No. 12 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a target polypeptide. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies (see, e.g., U.S. Pat. Nos. 5,625,126; 5,633,425; 5,569,825; 5,661,016; and 5,545,806; each of which is incorporated herein by reference in its entirety). Other human antibodies can be obtained commercially from, for example, Medarex, Inc. (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. See, e.g., Jespers et al., 1994, Biotechnology 12:899-903. Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan, M. P. and Carter, P., 2002, "The rise of monoclonal antibodies as therapeutics," In Anti-IgE and Allergic Disease, Jardieu, P. M. and Fick Jr., R. B, eds., Marcel Dekker, New York, N.Y., Chapter 20, pp. 427-469).

The antibody can be a functionally active fragment, derivative or analog (as further discussed infra) of an antibody that immunospecifically binds to a cancer cell antigen, or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (see, e.g., Kabat et al., 1991, Sequences of Proteins of Immunological Interest, Fifth Edition, National Institute of Health, Bethesda, Md.; Kabat E et al., 1980, J. Immunology 125(3):961-969).

In some embodiments, the antibody fragment is an Fv, Fab, Fab' or an F(ab')$_2$. Other useful antibodies are heavy chain and light chain dimers of antibodies, single chain antibodies (SCAB) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), a minibody, a diabody, a triabody, a tetrabody, a dsFv, an sc-Fv-Fc, an (scFv)$_2$, a fragment produced by a Fab expression library, an anti-idiotypic (anti-Id) antibody, or multispecific antibodies formed from antibody fragment(s).

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not the antibody. Preferably, the antibody or fragment thereof is covalently linked to the other protein at the C-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to, specific chemical cleavage, acetylation, formylation, metabolic synthesis in the presence of tunicamycin, etc. Additionally, the analog or derivative can contain one or more unnatural amino acids.

The antibodies can have modifications (e.g., substitutions, deletions or additions) in amino acid residues that interact with Fc receptors. In particular, the antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like, in literature publications, or by routine cloning and sequencing.

Antibodies that may be useful in the treatment of cancer include, but are not limited to, antibodies against tumor-associated antigens (TAA), such as an antigen expressed on a cancer cell, a cell of a cell proliferative disorder or a tumor cell. Tumor-associated polypeptides are more abundantly expressed on the surface of the cancer cells as compared to on the surface of the non-cancerous cells. Such tumor-associated antigens are known in the art, and can be prepared for use in generating antibodies using methods and information which are well known in the art.

Virtually any target protein can be targeted by an antibody, including any target protein which expression is correlated with expression on cells of a cancer, cell proliferative disorder or tumor. Suitable target proteins include human tumor antigens recognized by T cells (Robbins and Kawakami, 1996, Curr. Opin. Immunol. 8:628-636, incorporated herein by reference in its entirety), melanocyte lineage proteins, including gp100, MART-1/MelanA, TRP-1 (gp75), tyrosinase; Tumor-specific widely shared antigens, MAGE-1, MAGE-3, BAGE, GAGE-1, N-acetylglucosaminyltransferase-V, p15; Tumor-specific mutated antigens, beta-catenin, MUM-1, CDK4; Nonmelanoma antigens for breast, ovarian, cervical and pancreatic carcinoma, HER-2/neu, human papillomavirus-E6, -E7, MUC-1; cancer antigens, such as KS1/4 pan-carcinoma antigen (Perez and Walker, 1990, J. Immunol. 142:3662-3667; Bumal, 1988, Hybridoma 7(4):407-415); ovarian carcinoma antigen (CA125) (Yu et al., 1991, Cancer Res. 51(2):468-475); prostatic acid phosphate (Tailor et al., 1990, Nucl. Acids Res. 18(16):4928); prostate specific antigen (Henttu and Vihko, 1989, Biochem. Biophys. Res. Comm. 160(2):903-910; Israeli et al., 1993, Cancer Res. 53:227-230); melanoma-associated antigen p97 (Estin et al., 1989, J. Natl. Cancer Instit. 81(6):445-446); melanoma antigen gp75 (Vijayasardahl et al., 1990, J. Exp. Med. 171(4):1375-1380); high molecular weight melanoma antigen (HMW-MAA) (Natali et al., 1987, Cancer 59:55-63; Mittelman et al., 1990, J. Clin. Invest. 86:2136-2144); prostate specific membrane antigen; carcinoembryonic antigen (CEA) (Foon et al., 1994, Proc. Am. Soc. Clin. Oncol. 13:294); polymorphic epithelial mucin antigen; human milk fat globule antigen; a colorectal tumor-associated antigen, such as CEA, TAG-72 (Yokata et al., 1992, Cancer Res. 52:3402-3408), CO 17-1A (Ragnhammar et al., 1993, Int. J. Cancer 53:751-758); GICA 19-9 (Herlyn et al., 1982, J. Clin. Immunol. 2:135), CTA-1 and LEA; Burkitt's lymphoma antigen-38.13; CD19 (Ghetie et al., 1994, Blood 83:1329-1336); human B-lymphoma antigen-CD20 (Reff et al., 1994, Blood 83:435-445); CD33 (Sgouros et al., 1993, J. Nucl. Med. 34:422-430); melanoma specific antigens such as ganglioside GD2 (Saleh et al., 1993, J. Immunol., 151, 3390-3398), ganglioside GD3 (shiara et al., 1993, Cancer Immunol. Immunother. 36:373-380), ganglioside GM2 (Livingston et al., 1994, J. Clin. Oncol. 12:1036-1044), and ganglioside GM3 (Hoon et al., 1993, Cancer Res. 53:5244-5250); tumor-specific transplantation type of cell-surface antigen (TSTA) such as virally-induced tumor antigens including T-antigen DNA tumor viruses and envelope antigens of RNA tumor viruses; oncofetal antigen-alpha-fetoprotein such as CEA of colon, or bladder tumor oncofetal antigen (Hellstrom et al., 1985, Cancer. Res. 45:2210-2188); differentiation antigen such as human lung carcinoma antigen L6 or L20 (Hellstrom et al., 1986, Cancer Res. 46:3917-3923); antigens of fibrosarcoma; human leukemia T cell antigen-Gp37 (Bhattacharya-Chatterjee et al., 1988, J. Immunol. 141:1398-1403); neoglycoprotein, sphingolipids, breast cancer antigen such as EGFR (Epidermal growth factor receptor), HER2 antigen (p185$^{HER2}$), polymorphic epithelial mucin (PEM) (Hilkens et al., 1992, Trends in Bio. Chem. Sci. 17:359); malignant human lymphocyte antigen-APO-1 (Bernhard et al., 1989, Science 245:301-304); differentiation antigen (Feizi, 1985, Nature 314:53-57) such as I antigen found in fetal erythrocytes, primary endoderm, I antigen found in adult erythrocytes and preimplantation embryos, I(Ma) found in gastric adenocarcinomas, M18, M39 found in breast epithelium, SSEA-1 found in myeloid cells, VEP8, VEP9, Myl, $D_{156-22}$ found in colorectal cancer, TRA-1-85 (blood group H), C14 found in colonic adenocarcinoma, F3 found in lung adenocarcinoma, AH6 found in gastric cancer, Y hapten, Le$^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group Le$^a$) found in Adenocarcinoma, NS-10 found in adenocarcinomas, CO-43 (blood group Le$^b$), G49 found in EGF receptor of A431 cells, MH2 (blood group ALe$^b$/Le$^y$) found in colonic adenocarcinoma, 19.9 found in colon cancer, gastric cancer mucins, $T_5A_7$ found in myeloid cells, $R_{24}$ found in melanoma, 4.2, GD3, D1.1, OFA-1, $G_{M2}$, OFA-2, GD2, and M1:22:25:8 found in embryonal carcinoma cells, and SSEA-3 and SSEA-4.

In some embodiments, the antibody in an antibody against one of the following antigens (exemplary cancers are shown in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostate specific membrane antigen, prostatic acid phosphatase (prostate), epidermal growth factor (carcinomas), MAGE-1 (carcinomas), MAGE-2 (carcinomas), MAGE-3 (carcinomas), MAGE -4 (carcinomas), anti transferrin receptor (carcinomas), p97 (melanoma), MUC1-KLH (breast cancer), CEA (colorectal), gp100 (melanoma), MART1 (melanoma), IL-2 receptor (T-cell leukemia and lymphomas), CD20 (non Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail et al., 1993, Science 261:212-215), BR64 (Trail et al., 1997, Cancer Research 57:100 105), mAbs against the CD40 antigen, such as S2C6 mAb (Francisco et al., 2000, Cancer Res. 60:3225-3231) or other anti-CD40 antibodies, such as those disclosed in U.S. Patent Publication Nos. 2003-0211100 and 2002-0142358; mAbs against the CD70 antigen, such as 1F6 mAb and 2F2 mAb (see, e.g., U.S. Patent Publication No. 2006-0083736; and , and mAbs against the CD30 antigen, such as AC10 (Bowen et al., 1993, J. Immunol. 151:5896-5906; Wahl et al., 2002 Cancer Res. 62(13):3736-42) or MDX-0060 (U.S. Patent Publication No. 2004-0006215). Other internalizing antibodies that bind to tumor associated antigens can be used and have been reviewed (Franke et al., 2000, Cancer Biother. Radiopharm. 15:459 76; Murray, 2000, Semin. Oncol. 27:64 70; Breitling, F., and Dubel, S., Recombinant Antibodies, John Wiley, and Sons, New York, 1998).

In certain embodiments, useful antibodies can bind to a receptor or a receptor complex expressed on a target cell. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA 4, PD 1, and ICOS. Non-limiting examples of suitable TNF receptor superfamily members are CD27, CD40, CD95/Fas, CD134/OX40, CD137/4 1BB, TNFR1, TNFR2, RANK, TACI, BCMA, osteoprotegerin, Apo2/TRAIL R1, TRAIL R2, TRAIL R3, TRAIL R4, and APO 3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C type, S type, and I type lectin.

In some embodiments, the Drug-Linker-Ligand conjugate includes a Linker unit. A "Linker unit" (LU) is a bifunctional compound which can be used to link a Drug unit and a Ligand unit to form a Drug-Linker-Ligand Conjugate, or which is useful in the formation of immunoconjugates directed against target antigens. Such immunoconjugates allow the selective delivery of a cytotoxic or cytostatic agent to cancer cells, tumor cells and cells of a cell proliferative disorder. In some embodiments, a Drug-Linker conjugate is provided.

In one embodiment, the Linker unit of the Drug-Linker Compound and Drug-Linker-Ligand Conjugate has the formula:

-A$_a$-W$_w$-Y$_y$- wherein:
-A- is a Stretcher unit;
a is 0 or 1;
each —W— is independently an Amino Acid unit;
w is independently an integer ranging from 0 to 12;
—Y— is a Spacer unit; and
y is 0, 1 or 2.

In the Drug-Linker-Ligand Conjugate, the Linker links the Drug moiety and the Ligand unit. In some embodiments, a+w+y=0. In other embodiments, a+w+y=0 to 15, or 1 to 15. In some embodiments, a+w+y=1, 2 or 3.

The Stretcher unit (-A-), when present, is capable of linking a Ligand unit to an amino acid unit (—W—), the Ligand unit to a Spacer unit, or a Ligand unit to a Drug unit. In this regard a Ligand unit (L) has a functional group that can form a bond with a functional group of a Stretcher. Useful functional groups that can be present on a Ligand unit, either naturally or via chemical manipulation include, but are not limited to, sulfhydryl (—SH), amino, hydroxyl, carboxy, the anomeric hydroxyl group of a carbohydrate, and carboxyl. In one aspect, the Ligand unit's functional groups are sulfhydryl and/or amino. Sulfhydryl groups can be generated by reduction of an intramolecular disulfide bond of a Ligand unit. Alternatively, sulfhydryl groups can be generated by reaction of an amino group of a lysine moiety of a Ligand using 2-iminothiolane (Traut's reagent) or another sulfhydryl generating reagent.

In some embodiments, the Stretcher unit forms a bond with a sulfur atom of the Ligand unit. The sulfur atom can be derived from a sulfhydryl group of a Ligand. Representative Stretcher units of this embodiment are depicted within the square brackets of Formulas Ma and Mb, wherein L-, —W—, —Y—, -D, w and y are as defined above, and R$^{17}$ is selected from —C$_1$-C$_{10}$ alkylene-, —C$_3$-C$_8$ carbocyclo-, —O—(C$_1$-C$_8$ alkyl)-, -arylene-, —C$_1$-C$_{10}$ alkylene-arylene-, -arylene-C$_1$-C$_{10}$ alkylene-, —C$_1$-C$_{10}$ alkylene-(C$_3$-C$_8$ carbocyclo)-, —(C$_3$-C$_8$ carbocyclo)-C$_1$-C$_{10}$ alkylene-, —C$_3$-C$_8$ heterocyclo-, —C$_1$-C$_{10}$ alkylene-(C$_3$-C$_8$ heterocycle)-, —(C$_3$-C$_8$ heterocyclo)-C$_1$-C$_{10}$ alkylene-, —(CH$_2$CH$_2$O)$_r$-—, and —(CH$_2$CH$_2$O)$_r$—CH$_2$—; r is an integer ranging from 1 to 10, t is an integer of 0 to 1 and each R$^{24}$ is H or are combined to form =O. It is to be understood from all the exemplary embodiments of Formula I, IIa and IIb, such as that even where not denoted expressly, from 1 to 20 drug moieties are linked to a Ligand (p=1 to 20).

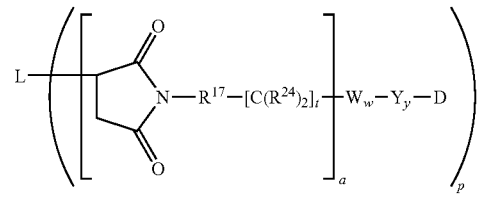

IIIa

-continued

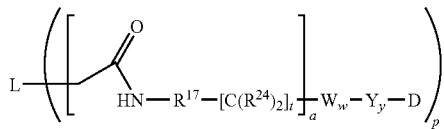

IIIb

An illustrative Stretcher unit is that of Formula IIIa wherein $R^{17}$ is —$(CH_2)_5$—:

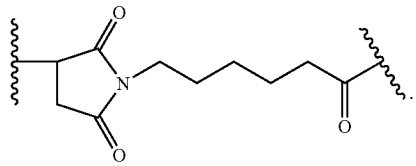

Another illustrative Stretcher unit is that of Formula IIIa wherein $R^{17}$ is —$(CH_2CH_2O)_r$—$CH_2$—; and r is 2:

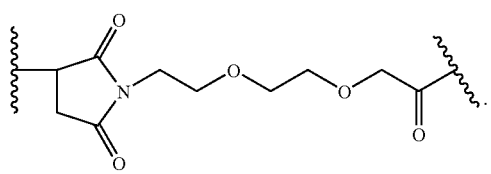

Still another illustrative Stretcher unit is that of Formula IIIb wherein $R^{17}$ is —$(CH_2)_5$—:

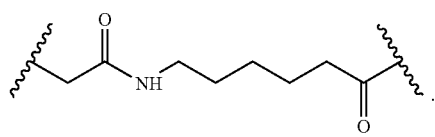

In related embodiments, the Stretcher unit is derived from a haloacetamide unit, such as a bromacetamide unit or an iodoacetamide.

In another embodiment, the Stretcher unit is linked to the Ligand unit via a disulfide bond between a sulfur atom of the Ligand unit and a sulfur atom of the Stretcher unit. A representative Stretcher unit of this embodiment is depicted within the square brackets of Formula IV, wherein $R^{17}$, L-, —W—, —Y—, -D, w and y are as defined above.

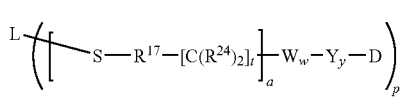

IV

In yet another embodiment, the reactive group of the Stretcher contains a reactive site that can form a bond with a primary or secondary amino group of a Ligand. Example of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R^{17}$—, L-, —W—, —Y—, -D, w and y are as defined above;

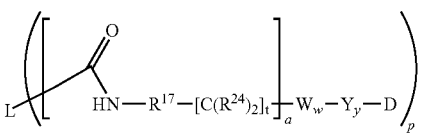

Va

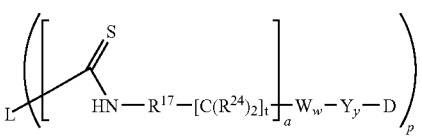

Vb

In yet another aspect, the reactive group of the Stretcher unit contains a reactive site that is reactive to a modified carbohydrate's (—CHO) group that can be present on a Ligand unit. For example, a carbohydrate can be mildly oxidized using a reagent such as sodium periodate and the resulting (—CHO) unit of the oxidized carbohydrate can be condensed with a Stretcher unit that contains a functionality such as a hydrazide, an oxime, a primary or secondary amine, a hydrazine, a thiosemicarbazone, a hydrazine carboxylate, or an arylhydrazide such as those described by Kaneko et al. (1991, Bioconjugate Chem. 2:133-41). Representative Stretcher units of this embodiment are depicted within the square brackets of Formulas VIa, VIb, and VIc, wherein —$R^{17}$—, L-, —W—, —Y—, -D, w and y are as defined above.

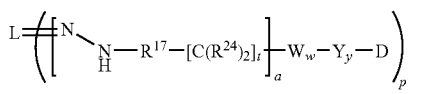

VIa

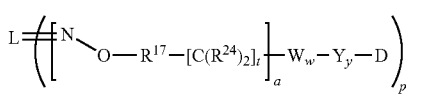

VIb

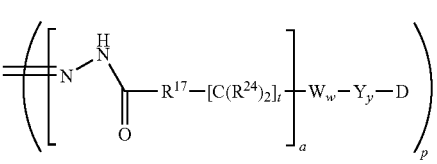

VIc

In some embodiments, the present invention provides an isolated and purified compound having the formula:

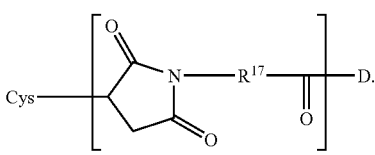

The Amino Acid unit (—W—), when present, links the Stretcher unit to the Spacer unit if the Spacer unit is present, links the Stretcher unit to the Drug moiety if the Spacer unit is absent, and links the Ligand unit to the Drug unit if the Stretcher unit and Spacer unit are absent.

$W_w$— is a dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

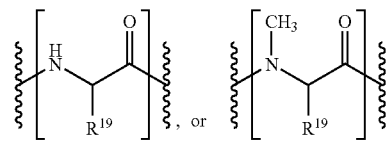

wherein $R^{19}$ is hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

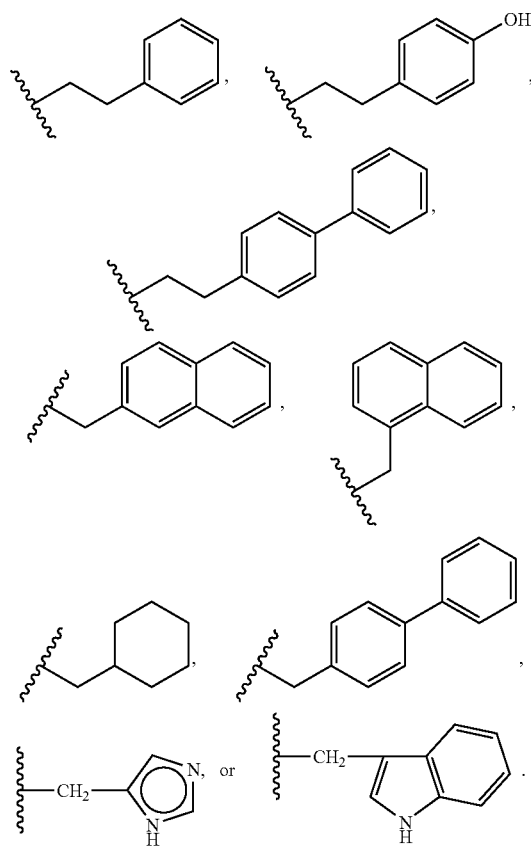

In some embodiments, the Amino Acid unit can be enzymatically cleaved by one or more enzymes, including a cancer or tumor-associated protease, to liberate the Drug unit (-D), which in one embodiment is protonated in vivo upon release to provide a Drug (D).

In certain embodiments, the Amino Acid unit can comprise natural amino acids. In other embodiments, the Amino Acid unit can comprise non-natural amino acids. Illustrative $W_w$ units are represented by formulas (VII)-(IX):

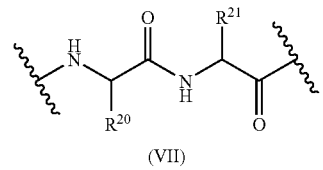

(VII)

wherein $R^{20}$ and $R^{21}$ are as follows:

| $R^{20}$ | $R^{21}$ |
|---|---|
| Benzyl | (CH$_2$)$_4$NH$_2$; |
| methyl | (CH$_2$)$_4$NH$_2$; |
| isopropyl | (CH$_2$)$_4$NH$_2$; |
| isopropyl | (CH$_2$)$_3$NHCONH$_2$; |
| benzyl | (CH$_2$)$_3$NHCONH$_2$; |
| isobutyl | (CH$_2$)$_3$NHCONH$_2$; |
| sec-butyl | (CH$_2$)$_3$NHCONH$_2$; |
| 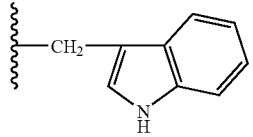 | (CH$_2$)$_3$NHCONH$_2$; |
| benzyl | methyl; and |
| benzyl | (CH$_2$)$_3$NHC(=NH)NH$_2$; |

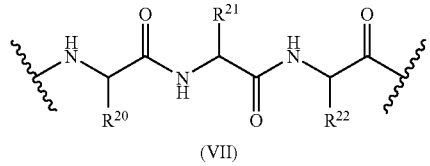

(VII)

wherein $R^{20}$, $R^{21}$ and $R^{22}$ are as follows:

| $R^{20}$ | $R^{21}$ | $R^{22}$ |
|---|---|---|
| benzyl | benzyl | (CH$_2$)$_4$NH$_2$; |
| isopropyl | benzyl | (CH$_2$)$_4$NH$_2$; and |
| H | benzyl | (CH$_2$)$_4$NH$_2$; |

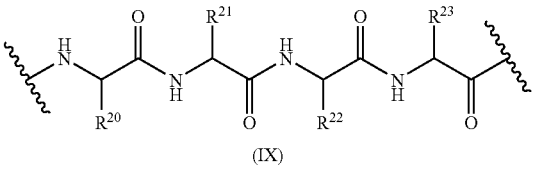

(IX)

wherein $R^{20}$, $R^{21}$, $R^{22}$ and $R^{23}$ are as follows:

| $R^{20}$ | $R^{21}$ | $R^{22}$ | $R^{23}$ |
|---|---|---|---|
| H | benzyl | isobutyl | H; and |
| methyl | isobutyl | methyl | isobutyl. |

Exemplary Amino Acid units include, but are not limited to, units of Formula VII where: $R^{20}$ is benzyl and $R^{21}$ is —(CH$_2$)$_4$NH$_2$; $R^{20}$ is isopropyl and $R^{21}$ is —(CH$_2$)$_4$NH$_2$; or $R^{20}$ is isopropyl and $R^{21}$ is —(CH$_2$)$_3$NHCONH$_2$. Another exemplary Amino Acid unit is a unit of Formula VIII wherein $R^{20}$ is benzyl, $R^{21}$ is benzyl, and $R^{22}$ is —(CH$_2$)$_4$NH$_2$.

Useful —$W_w$— units can be designed and optimized in their selectivity for enzymatic cleavage by a particular enzymes, for example, a tumor-associated protease. In one embodiment, a —$W_w$— unit is that whose cleavage is catalyzed by cathepsin B, C and D, or a plasmin protease.

In one embodiment, —W$_w$— is a dipeptide, tripeptide, tetrapeptide or pentapeptide.

In another embodiment, when R$^{19}$, R$^{20}$, R$^{21}$, R$^{22}$ or R$^{23}$ is other than hydrogen, the carbon atom to which R$^{19}$, R$^{20}$, R$^{21}$, R$^{22}$ or R$^{23}$ is attached is chiral.

Each carbon atom to which R$^{19}$, R$^{20}$, R$^{21}$, R$^{22}$ or R$^{23}$ is attached is independently in the (S) or (R) configuration.

In one aspect of the Amino Acid unit, the Amino Acid unit is valine-citrulline (i.e., val-cit or vc). In another aspect, the Amino Acid unit is phenylalanine-lysine (i.e., fk). In yet another aspect of the Amino Acid unit, the Amino Acid unit is N-methylvaline-citrulline. In yet another aspect, the Amino Acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine (SEQ ID NO:1) or isonepecotic acid.

The Spacer unit (—Y—), when present, links an Amino Acid unit to the Drug unit when an Amino Acid unit is present. Alternately, the Spacer unit links the Stretcher unit to the Drug unit when the Amino Acid unit is absent. The Spacer unit also links the Drug unit to the Ligand unit when both the Amino Acid unit and Stretcher unit are absent.

Spacer units are of two general types: non self-immolative or self-immolative. A non self-immolative Spacer unit is one in which part or all of the Spacer unit remains bound to the Drug moiety after cleavage, particularly enzymatic, of an Amino Acid unit from the Drug-Linker-Ligand Conjugate or the Drug-Linker Compound. Examples of a non self-immolative Spacer unit include, but are not limited to a glycine-glycine Spacer unit and a glycine Spacer unit (both depicted in Scheme 1) (infra). When a conjugate containing a glycine-glycine Spacer unit or a glycine Spacer unit undergoes enzymatic cleavage via an enzyme (e.g., a tumor-cell associated-protease, a cancer-cell-associated protease or a lymphocyte-associated protease), a glycine-glycine-Drug moiety or a glycine-Drug moiety is cleaved from L-A$_a$-W$_w$—. In one embodiment, an independent hydrolysis reaction takes place within the target cell, cleaving the glycine-Drug moiety bond and liberating the Drug.

In another embodiment, —Y$_y$— is a p-aminobenzyl alcohol (PAB) unit (see Schemes 2 and 3) whose phenylene portion is substituted with Q$_m$ wherein Q is —C$_1$-C$_8$ alkyl, —O—(C$_1$-C$_8$ alkyl), -halogen, -nitro or -cyano; and m is an integer ranging from 0 to 4.

Scheme 1

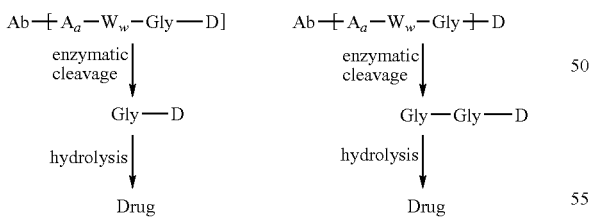

In some embodiments, a non self-immolative the Spacer unit (—Y—) is -Gly-. In some embodiments, a non self-immolative Spacer unit (—Y—) is -Gly-Gly-.

In one embodiment, a Drug-Linker conjugate or a Drug-Linker-Ligand Conjugate, or a pharmaceutically acceptable salt or solvate thereof, is provided in which the Spacer unit is absent (y=0).

Alternatively, a conjugate containing a self-immolative Spacer unit can release the Drug unit -D. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved.

In some embodiments, —Y— is a PAB group that is linked to —W$_w$— via the amino nitrogen atom of the PAB group, and connected directly to -D via a carbonate, carbamate or ether group. Without being bound by any particular theory or mechanism, Scheme 2 depicts a possible mechanism of Drug release of a PAB group which is attached directly to the Drug unit -D via a carbamate or carbonate group as described by Toki et al. (2002, J. Org. Chem. 67:1866-1872).

Scheme 2

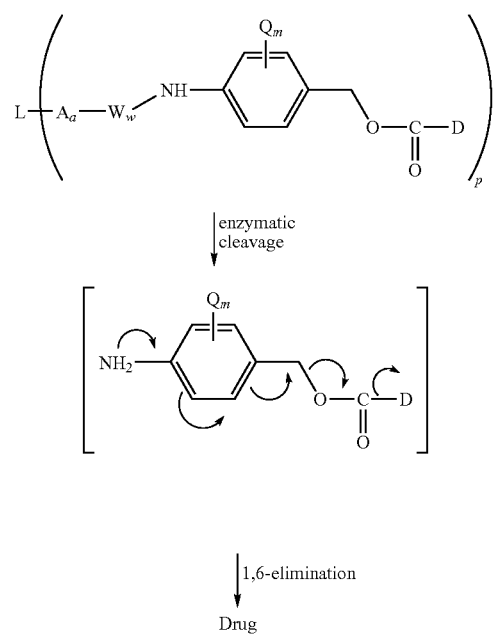

In Scheme 2, Q is —C$_1$-C$_8$ alkyl, —O—(C$_1$-C$_8$ alkyl), -halogen, -nitro or -cyano; m is an integer ranging from 0 to 4; and p ranges from 1 to about 20.

Without being bound by any particular theory or mechanism, Scheme 3 depicts a possible mechanism of Drug release of a PAB group which is attached directly to -D via an ether or amine linkage, wherein D includes the oxygen or nitrogen group is part of the Drug unit.

Scheme 3

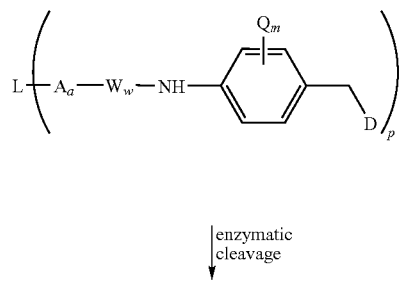

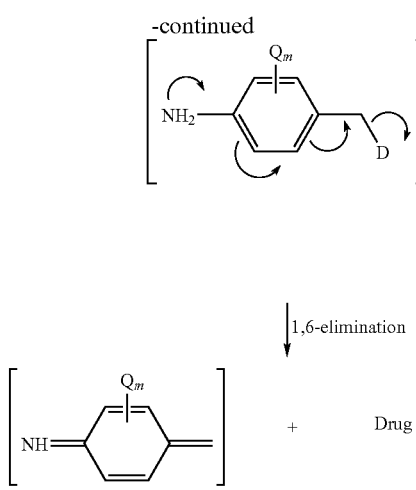

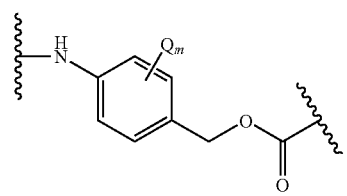

In one aspect, Spacer units (—$Y_y$—) are represented by Formulas (X)-(XII):

wherein Q is —$C_1$-$C_8$ alkyl, —O—($C_1$-$C_8$ alkyl), -halogen, -nitro or -cyano; and m is an integer ranging from 0 to 4;

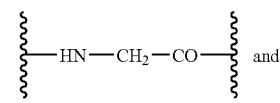

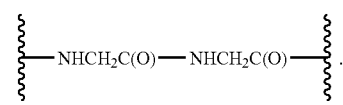

Embodiments of the Formula I, IIa and IIb comprising antibody drug conjugate compounds can include:

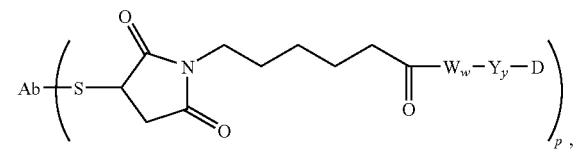

wherein w and y are each 0, 1 or 2, and S is a reactive thiol group of Ab;

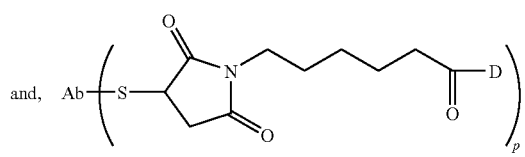

wherein w and y are each 0, and S is a reactive thiol group of Ab;

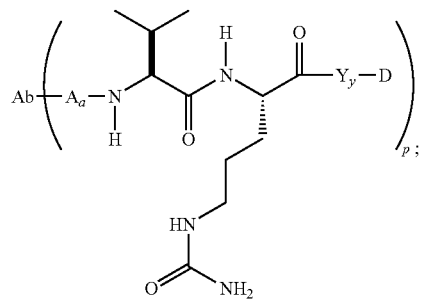

In Scheme 3, Q is —$C_1$-$C_8$ alkyl, —O—($C_1$-$C_8$ alkyl), -halogen, -nitro or -cyano; m is an integer ranging from 0 to 4; and p ranges from 1 to about 20.

Other examples of self-immolative spacers include, but are not limited to, aromatic compounds that are electronically similar to the PAB group such as 2-aminoimidazol-5-methanol derivatives (Hay et al., 1999, Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, Chemistry Biology 2:223), appropriately substituted bicyclo[2.2.1] and bicyclo[2.2.2] ring systems (Storm et al., 1972, J. Amer. Chem. Soc. 94:5815) and 2-aminophenylpropionic acid amides (Amsberry et al., 1990, J. Org. Chem. 55:5867). Elimination of amine-containing drugs that are substituted at the α-position of glycine (Kingsbury et al., 1984, J. Med. Chem. 27:1447) are also examples of self-immolative spacers.

In one embodiment, the Spacer unit is a branched bis (hydroxymethyl)styrene (BHMS) unit as depicted in Scheme 4, which can be used to incorporate and release multiple drugs.

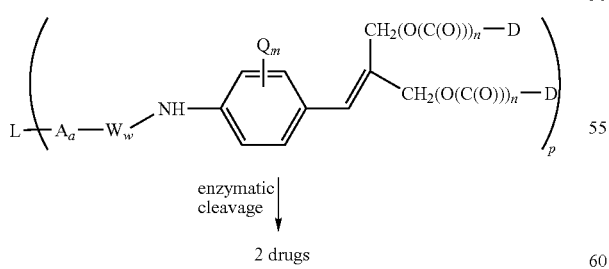

In Scheme 4, Q is —$C_1$-$C_8$ alkyl, —O—($C_1$-$C_8$ alkyl), -halogen, -nitro or -cyano; m is an integer ranging from 0 to 4; n is 0 or 1; and p ranges from 1 to about 20.

In some embodiments, the -D moieties are the same. In yet another embodiment, the -D moieties are different.

-continued

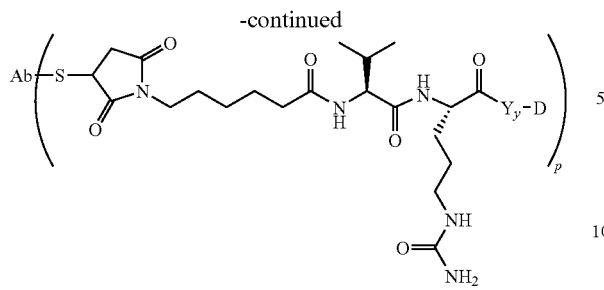

wherein S is a reactive thiol group of Ab; and

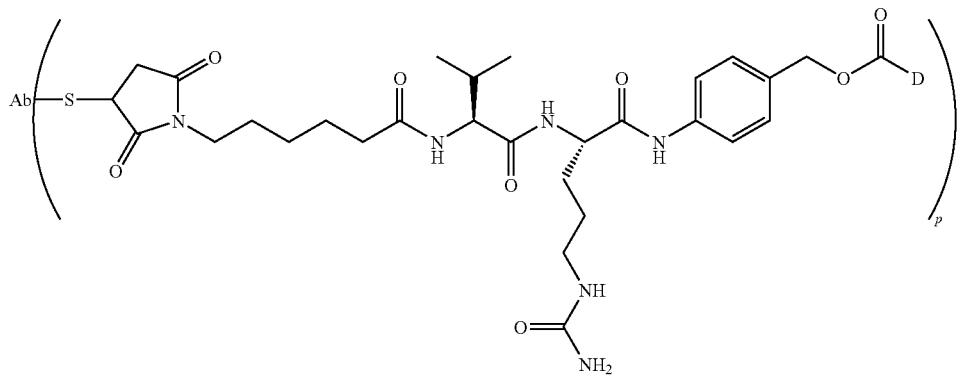

wherein S is a reactive thiol group of Ab.

Other embodiments of the Formula I, IIa and IIb include antibody drug conjugate compounds having the formula:

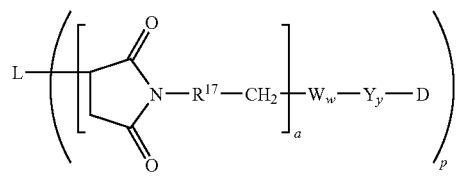

wherein L is an antibody or antibody fragment; $R^{17}$ is $C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O)_r$—, or —($CH_2CH_2O)_r$—$CH_2$—; and r is an integer ranging from 1 to 10.

In other embodiments, the antibody drug conjugate has the formula:

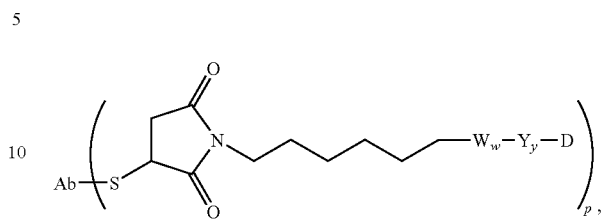

wherein Ab is an antibody or antibody fragment, and S is a reactive thiol group of Ab.

In other embodiments, the antibody drug conjugate has the formula:

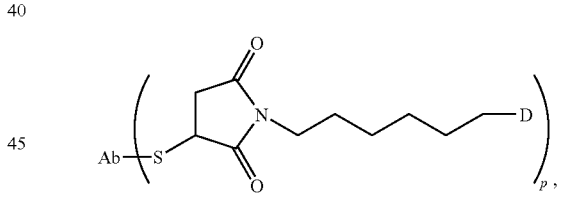

wherein Ab is an antibody or antibody fragment, and S is a reactive thiol group of Ab.

The Drug unit (-D) is an auristatin that is a poor substrate for a P-gp transporter. P-gp can cause resistance to anthracyclines (such as doxorubicin, daunorubicin, and epirubicin), mitxantrone, vinca alkaloids (vinblastine, vincristine), etoposide, the taxanes (paclitaxel, docetaxel), and actinomycin D by increasing efflux of such drugs from the intracellular compartment.

As used herein, a "poor substrate for a P-gp transporter" is a drug or Drug unit that has reduced affinity for and/or transport by P-gp compared to drugs known to be transported by P-gp (e.g., doxorubicin or vincristine). Exemplary poor substrates for a P-gp transporter include, but are not limited to, cisplatin and certain auristatins as described herein. A poor substrate for a P-gp transporter can have P-gp efflux rates that are at least $10^{-1}$, $10^{-2}$, $10^{-3}$, $10^{-4}$ or $10^{-5}$ relative to that of doxorubicin or vincristine. Alternatively, a poor substrate for a P-gp transporter can have an $IC_{50}$ that is less than 2-, 5-, 10-, 15- or 20-fold higher in untreated compared to verapamil-treated cells and/or drug-resistant progeny compared to parental cells.

As used herein, a "good substrate for a P-gp transporter" is a drug or Drug unit that has elevated affinity for and/or transport by P-gp compared to drugs known not to be transported by P-gp (e.g., camptothecin or cisplatin). Exemplary good substrates for a P-gp transporter include, but are not limited to, anthracyclines (such as doxorubicin, daunorubicin, and epirubicin), mitxantrone, vinca alkaloids (vinblastine, vincristine), etoposide, the taxanes (paclitaxel, docetaxel), and actinomycin D. A good substrate for a P-gp transporter can have P-gp efflux rates that are at least $10^1$, $10^2$, $10^3$, $10^4$ or $10^5$ relative to that of campothecin or cisplatin. Alternatively, a good substrate for a P-gp transporter can have an $IC_{50}$ that is more than 20-, 50-, 100-, 200- or 500-fold higher in untreated compared to verapamil-treated cells and/or drug-resistant progeny compared to parental cells. In one embodiment the drug is not a good substrate for P-gp.

As used herein, an "auristatin" refers to a molecule that exhibits a cytotoxic or cytostatic activity on cancer cells and exhibits reduced affinity for and/or transport by P-gp. In some embodiments, the auristatin derivative is a zwitterionic compound. In some embodiments, the auristatin has a P-gp efflux rate that is at least $10^{-1}$, $10^{-2}$, $10^{-3}$, $10^{-4}$ or $10^{-5}$ relative to that of doxorubicin. In some embodiments, the auristatin has comparable cytotoxic or cytotstatic activity in cancer cell lines expressing a functional P-gp in the absence or presence of an effective dose of the P-gp inhibitor verapamil. In this context, "comparable" means that the $IC_{50}$ is less than 2-, 5-, 10-, 15- or 20-fold higher in untreated compared to verapamil-treated cells. In some embodiments, the auristatin has comparable cytotoxic or cytotstatic activity in parental cells compared to their drug-resistant progeny (see Table 2 infra). In this context, "comparable" means that the $IC_{50}$ is less than 2-, 5-, 10-, 15- or 20-fold higher in drug-resistant progeny compared to parental cells.

In one embodiment, -D is of the following formula $D_F$:

wherein, independently at each location:
$R^2$ is selected from H and $C_1$-$C_{10}$ alkyl;
$R^3$ is selected from H, $C_1$-$C_{10}$ alkyl, $C_3$-$C_8$ carbocycle, aryl, $C_1$-$C_{10}$ alkyl-aryl, $C_1$-$C_{10}$ alkyl-($C_3$-$C_8$ carbocycle), $C_3$-$C_8$ heterocycle and $C_1$-$C_{10}$ alkyl-($C_3$-$C_8$ heterocycle);
$R^4$ is selected from H, $C_1$-$C_{10}$ alkyl, $C_3$-$C_8$ carbocycle, aryl, $C_1$-$C_{10}$ alkyl-aryl, $C_1$-$C_{10}$ alkyl-($C_3$-$C_8$ carbocycle), $C_3$-$C_8$ heterocycle and $C_1$-$C_{10}$ alkyl-($C_3$-$C_s$ heterocycle);
$R^5$ is selected from H and methyl; or $R^4$ and $R^5$ jointly form a carbocyclic ring and have the formula —$(CR^aR^b)_{n1}$— wherein $R^a$ and $R^b$ are independently selected from H, $C_1$-$C_{10}$ alkyl and $C_3$-$C_8$ carbocycle and n1 is selected from 2, 3, 4, 5 and 6;
$R^6$ is selected from H and $C_1$-$C_{10}$ alkyl;
$R^7$ is selected from H, $C_1$-$C_{10}$ alkyl, $C_3$-$C_8$ carbocycle, aryl, $C_1$-$C_{10}$ alkyl-aryl, $C_1$-$C_{10}$ alkyl-($C_3$-$C_8$ carbocycle), $C_3$-$C_8$ heterocycle and $C_1$-$C_{10}$ alkyl-($C_3$-$C_8$ heterocycle);
each $R^8$ is independently selected from H, OH, $C_1$-$C_{10}$ alkyl, $C_3$-$C_8$ carbocycle and O—($C_1$-$C_{10}$ alkyl);
$R^9$ is selected from H and $C_1$-$C_{10}$ alkyl;
$R^{10}$ is selected from aryl and $C_3$-$C_8$ heterocycle;
Z is O; and
$R^{11}$ is selected from H or Me.

In one embodiment, $R^3$, $R^4$ and $R^7$ are independently isopropyl or sec-butyl and $R^5$ is H. In an exemplary embodiment, $R^3$ and $R^4$ are each isopropyl, $R^5$ is H, and $R^7$ is sec-butyl.

In another embodiment, $R^2$ and $R^6$ are each methyl, and $R^9$ is H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is H, $R^7$ is sec-butyl, each occurrence of $R^8$ is —$OCH_3$, and $R^9$ is H.

In one embodiment, $R^{10}$ is aryl.

In an exemplary embodiment, $R^{10}$ is -phenyl.

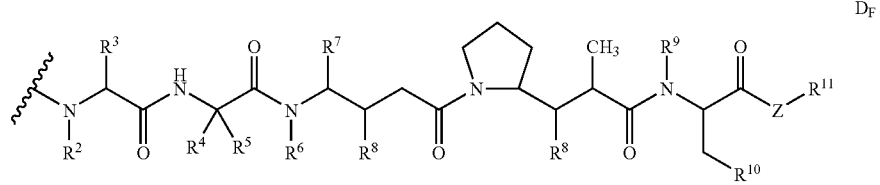

$D_F$

In some embodiments, -D is a Drug unit having the Formula

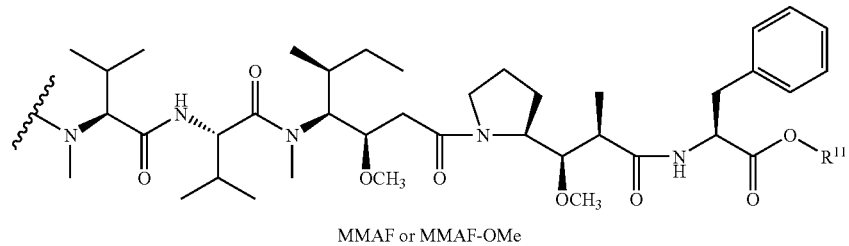

MMAF or MMAF-OMe wherein $R^1$=H or Me.

In some embodiments, the Drug unit (-D) has the following formula:

MMAF

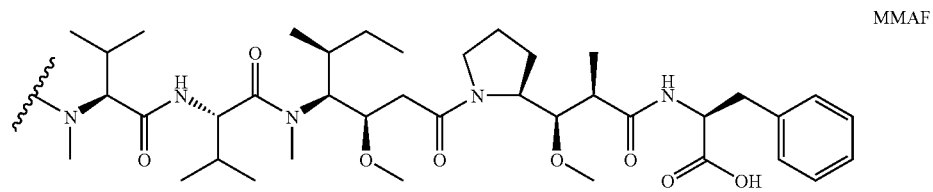

In some embodiments, the Drug unit is not TZT-1027.

The auristatin can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. General methods for preparing auristatins are described in the following: U.S. Pat. No. 5,635,483; U.S. Pat. No. 5,780,588; Pettit et al., 1989, J. Am. Chem. Soc. 111:5463-5465; Pettit et al., 1998, Anti-Cancer Drug Design 13:243-277; and Pettit et al., 1996, J. Chem. Soc. Perkin Trans. 1 5:859-863. More specifically, MMAF and its derivatives can be synthesized as described in International Patent Publication WO2005081711 (the disclosure of which is incorporated in its entirety by reference herein).

Methods of determining whether an agent exerts a cytostatic or cytotoxic effect on a cell are known. Illustrative examples of such methods for Drug-Linker-Ligand Conjugate(s) such as an antibody drug conjugate (ADC) are described infra. Generally, the cytotoxic or cytostatic activity of an ADC can be measured by: exposing mammalian cells expressing a target protein of the antibody of the ADC in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the ADC of the invention.

For determining whether an ADC exerts a cytostatic effect, a thymidine incorporation assay may be used. For example, cancer cells expressing a target antigen at a density of 5,000 cells/well of a 96-well plated can be cultured for a 72-hour period and exposed to 0.5 μCi of $^3$H-thymidine during the final 8 hours of the 72-hour period. The incorporation of $^3$H-thymidine into cells of the culture is measured in the presence and absence of the ADC.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an ADC is useful in the treatment of cancers.

Cell viability can be measured by determining in a cell the uptake of a dye such as neutral red, trypan blue, or ALAMAR™ blue (see, e.g., Page et al., 1993, Intl. J. Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, J. Natl. Cancer Inst. 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane.

Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, Cancer Research 55:3110-16.)

The effects of ADCs can be tested or validated in animal models. A number of established animal models of cancers are known to the skilled artisan, any of which can be used to assay the efficacy of a Drug-Linker-Ligand conjugate, such as an ADC. Non-limiting examples of such models are described infra. Moreover, small animal models to examine the in vivo efficacies of ADCs can be created by implanting human tumor cell lines into appropriate immunodeficient rodent strains, e.g., athymic nude mice or SCID mice.

In another aspect, compositions are provided that include an effective amount of a Drug-Linker-Ligand conjugate(s) or a Drug-Linker conjugate(s), with or without a pharmaceutically acceptable carrier or vehicle. For convenience, the Drug-Linker-Ligand conjugate or a Drug-Linker conjugate can be referred to as a Conjugate. The compositions are suitable for veterinary or human administration.

The compositions can be in any form that allows for the composition to be administered to a patient. For example, the composition can be in the form of a liquid or solid. Typical routes of administration include, without limitation, oral, topical, parenteral, sublingual, rectal, vaginal, ocular, and intra-tumor. Parenteral administration includes subcutaneous injections, intravenous, intramuscular, intrasternal injection or infusion techniques. In one aspect, the compositions are administered parenterally. In yet another aspect, the compositions are administered intravenously.

Pharmaceutical compositions can be formulated so as to allow the Conjugate to be bioavailable upon administration of the composition to a patient. Compositions can take the form of one or more dosage units, where for example, a tablet can be a single dosage unit, and a container of a Conjugate in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the Conjugate, the manner of administration, and the composition employed.

The pharmaceutically acceptable carrier or vehicle can be particulate, so that the compositions are, for example, in tablet or powder form. The carrier(s) can be liquid, with the compositions being, for example, an oral syrup or injectable liquid.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it can contain, in addition to materials of the above type, a liquid carrier such as polyethylene glycol, cyclodextrin or a fatty oil.

The composition can be in the form of a liquid, e.g., an elixir, syrup, solution, emulsion or suspension. In a composition for administration by injection, one or more of a surfactant, preservative, wetting agent, dispersing agent, suspending agent, buffer, stabilizer and isotonic agent can also be included. The liquid can be useful for oral administration or for delivery by injection. When intended for oral administration, a composition can comprise one or more of a sweetening agent, preservatives, dye/colorant and flavor enhancer.

The liquid compositions, whether they are solutions, suspensions or other like form, can also include one or more of the following: sterile diluents such as water for injection, saline solution, such as physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, amino acids, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the Conjugate that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a Conjugate such that a suitable dosage will be obtained. Typically, this amount is at least about 0.01% of a Conjugate by weight of the composition. In some embodiments, the compositions are prepared so that a parenteral dosage unit contains from about 0.01% to about 2% by weight of the Conjugate. When intended for oral administration, this amount can be varied to range from about 0.1% to about 80% by weight of the composition. In one aspect, oral compositions can comprise from about 4% to about 50% of the Conjugate by weight of the composition.

Generally, the dosage of a Conjugate administered to a patient is typically about 0.01 mg/kg to about 2000 mg/kg of the animal's body weight. In one embodiment, the dosage administered to a patient is between about 0.01 mg/kg to about 10 mg/kg of the animal's body weight; in another embodiment, the dosage administered to a patient is between about 0.1 mg/kg and about 250 mg/kg of the animal's body weight. In yet another embodiment, the dosage administered to a patient is between about 0.1 mg/kg and about 20 mg/kg of the animal's body weight. In other embodiments, the dosage administered is between about 0.1 mg'kg to about 20 mg/kg, about 0.5 mg/kg to about 20 mg/kg, about 1 mg/kg to about 20 mg/kg, about 0.1 mg/kg to about 15 mg/kg, about 0.5 mg/kg to about 15 mg/kg, about 1 mg/kg to about 15 mg/kg, about 0.1 mg/kg to about 10 mg/kg, about 0.5 mg/kg to about 10 mg/kg or about 1 mg/kg to about 10 mg/kg of the animal's body weight.

For intravenous administration, the composition can comprise from about 0.01 to about 100 mg of a Conjugate per kg of the animal's body weight. In one aspect, the composition can include from about 1 to about 100 mg of the Conjugate per kg of the animal's body weight. In some embodiments, the amount administered will be in the range from about 0.1 to about 25 mg/kg of body weight of the Conjugate. In yet another embodiment, the dosage administered to a patient is between about 0.1 mg/kg and about 20 mg/kg of the animal's body weight. In other embodiments, the dosage administered is between about 0.1 mg/kg to about 20 mg/kg, about 0.5 mg/kg to about 20 mg/kg, about 1 mg/kg to about 20 mg/kg, about 0.1 mg/kg to about 15 mg/kg, about 0.5 mg/kg to about 15 mg/kg, about 1 mg/kg to about 15 mg/kg, about 0.1 mg/kg to about 10 mg/kg, about 0.5 mg/kg to about 10 mg/kg or about 1 mg/kg to about 10 mg/kg of the animal's body weight.

The Conjugates or compositions can be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a Conjugate or composition. In certain embodiments, more than one Conjugate or composition is administered to a patient.

In specific embodiments, it can be desirable to administer one or more Conjugates or compositions locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers.

In one embodiment, administration can be by direct injection at the site (or former site) of a cancer, tumor or neoplastic or pre-neoplastic tissue. In another embodiment, administration can be by direct injection at the site (or former site) of manifestation of disease.

In certain embodiments, it can be desirable to introduce one or more Conjugates or compositions into the central nervous system by any suitable route, including intraventricular and intrathecal injection. Intraventricular injection can be facilitated by an intraventricular catheter, for example, attached to a reservoir, such as an Ommaya reservoir.

In yet another embodiment, the Conjugates or compositions can be delivered in a controlled release system, such as, but not limited to, a pump or various polymeric materials. In yet another embodiment, a controlled-release system can be placed in proximity of the target of the Conjugates or compositions, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a Conjugate is administered. Such pharmaceutical carriers can be liquids, such as water, including aqueous solutions, and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a patient, the Conjugate or compositions and pharmaceutically acceptable carriers are sterile. Water is an exemplary carrier when the Conjugates are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The compositions, if desired, can also contain minor amounts of wetting or emulsifying agents, or pH buffering agents.

In an embodiment, the Conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a Conjugate is to be administered by infusion, it can be dispensed, for example, with an infusion bottle containing sterile pharmaceutical grade water or saline. Where the Conjugate is administered by injection, an ampoule of sterile water for injection or saline can be provided so that the ingredients can be mixed prior to administration.

Whether in solid or liquid form, the compositions can include a pharmacological agent used in the treatment of cancer, an autoimmune disease or an infectious disease.

The Drug-Linker-Ligand conjugates are useful for treating cancer, in particular, drug resistant or refractory cancers, in a patient. In some embodiments, the patient has a refractory or drug-resistant cancer, where the patient has failed at least one prior treatment with a chemotherapeutic agent.

In some embodiments, drug resistance can be determined by obtaining a sample from a patient and determining P-gp protein and/mRNA levels. See, e.g., Zhan et al., 1997, Blood. 89(10):3795-800. In other embodiments, P-gp levels can be determined using a fluorescent dye or radioactive label(s). See, e.g., Homolya et al., 1993, J. Biol. Chem. 268:21493-21496; Hollo et al., 1994, Biochimica et Biophysica Acta 1191:384-388; Liming a et al., 1994, Exp. Cell Res. 212:291-296; Kessel et al., 1991, Cancer Research 51:4665-4670; Neyfakh, 1988, Exp. Cell Res. 174:168-176; Taki et al., 1998, J. Nucl. Med. 39(7):1179-84; and U.S. Pat. No. 5,872,014; the disclosures of which are incorporated by reference in their entirety herein. Other methods of determining drug resistance are disclosed in U.S. Patent Publication Nos. 2005-0238707, 2005-0227249 and 2004-0176403, the disclosures of which are incorporated by reference herein in their entirety.

The Drug-Linker-Ligand conjugates and Drug-Linker conjugates are accordingly useful in a variety of settings for the treatment of cancers. In some embodiments, the Ligand unit binds to the tumor cell, cancer cell, or a cell of a cell proliferative disorder, wherein the Ligand unit binds to a target protein expressed on the cell. In some embodiments, the Ligand unit binds to a tumor cell antigen, a cancer cell antigen or an antigen of a cell proliferative disorder, which is on the surface of the cell, wherein the Ligand unit binds to a target protein expressed on the cell. In some embodiments, the Ligand unit binds to a tumor cell antigen, a cancer cell antigen or an antigen of a cell of cell proliferative disorder, which is an extracellular matrix protein associated with the cell, wherein the Ligand unit binds to a target protein expressed on the cell. In other embodiments, the Ligand unit binds to an antigen of bystander cell, wherein the bystander cell is associated with the cancer, tumor or cell proliferative disorder.

The specificity of the Ligand unit for a particular tumor cell or cancer cell can be useful for determining those tumors or cancers that are most effectively treated. For example, conjugates having a BR96 Ligand unit can be useful for treating antigen positive carcinomas including those of the lung, breast, colon, ovaries, and pancreas. Conjugates having an anti-CD30 or an anti-CD20 Ligand unit can be useful for treating hematologic malignancies.

Other particular types of cancers that can be treated include, but are not limited to, refractory or drug resistant forms of carcinomas, lymphomas, blastomas, sarcomas, leukemias, lymphoid malignancies, and other cancers, cell proliferative disorders and tumors. In some embodiments, the cancer is one of the cancers listed in the following Table 1:

TABLE 1

Solid tumors, including but not limited to:

fibrosarcoma
myxosarcoma
liposarcoma
chondrosarcoma
osteogenic sarcoma
chordoma
angiosarcoma
endotheliosarcoma
lymphangiosarcoma
lymphangioendotheliosarcoma
synovioma
mesothelioma
Ewing's tumor
leiomyo sarcoma
rhabdomyosarcoma
colon cancer
rectal cancer
colorectal cancer
kidney cancer
pancreatic cancer
bone cancer
breast cancer
ovarian cancer
prostate cancer
penile carcinoma
esophogeal cancer
gastric cancer
gastrointestinal cancer
stomach cancer
peritoneal cancer
hepatic carcinoma
hepatocellular cancer
liver cancer
oral cancer
nasal cancer
throat cancer
squamous cell carcinoma (e.g., epithelial)
basal cell carcinoma
adenocarcinoma
sweat gland carcinoma
sebaceous gland carcinoma
papillary carcinoma
papillary adenocarcinomas TABLE 1-continued Solid tumors, including but not limited to:

cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
endometrial or uterine carcinoma
vulval cancer
testicular cancer
bladder carcinoma
lung cancer, including small cell lung carcinoma, non-small cell lung cancer, adenocarcinoma of the lung and squamous carcinoma of the lung
epithelial carcinoma
glioma
glioblastoma
glioblastoma multiforme
astrocytoma
medulloblastoma
craniopharyngioma
ependymoma
pinealoma
hemangioblastoma
acoustic neuroma
oligodendroglioma
meningioma
skin cancer
melanoma
neuroblastoma
retinoblastoma
salivary gland carcinoma
thyroid cancer
head cancer
neck cancer
anal cancer
Blood-borne cancers (hematologic), including but not limited to:
acute lymphoblastic leukemia "ALL"
acute lymphoblastic B-cell leukemia
acute lymphoblastic T-cell leukemia
acute myeloblastic leukemia "AML"
acute promyelocytic leukemia "APL"
acute monoblastic leukemia
acute erythroleukemic leukemia
acute megakaryoblastic leukemia
acute myelomonocytic leukemia
acute nonlymphocytic leukemia
acute undifferentiated leukemia
chronic myelocytic leukemia "CML"
chronic lymphocytic leukemia "CLL"
hairy cell leukemia
multiple myeloma
Acute and chronic leukemias:
lymphoblastic
myelogenous
lymphocytic
myelocytic leukemias
Lymphomas:
Hodgkin's disease
non-Hodgkin's Lymphoma
Multiple myeloma
Waldenstrom's macroglobulinemia
Heavy chain disease
Polycythemia vera The Conjugates can provide conjugate-specific tumor or cancer targeting, thus reducing general toxicity of these compounds. In some embodiments, the Linker units can stabilize the Conjugates in blood, yet are cleavable by cancer-specific, tumor-specific or cell proliferative disorder-specific proteases within the cell, thereby liberating the Drug intracellularly.

In some embodiments, methods for treating refractory cancers are provided that include administering to a patient in need thereof an effective amount of a Conjugate (e.g., a Drug-Linker-Ligand unit or a Drug-Linker unit) and a chemotherapeutic agent. In one embodiment the chemotherapeutic agent is that to which treatment of the cancer has not been found to be refractory. In another embodiment, the chemotherapeutic agent is that to which the treatment of cancer has been found to be refractory. The Conjugates can be administered to a patient who has also undergone surgery as treatment for the cancer. In one embodiment, the additional method of treatment is radiation therapy.

In a specific embodiment, the Conjugate is administered concurrently with the chemotherapeutic agent or with radiation therapy. In another specific embodiment, the chemotherapeutic agent or radiation therapy is administered prior or subsequent to administration of a Conjugate, in one aspect at least an hour, five hours, 12 hours, a day, a week, a month, in further aspects several months (e.g., up to three months), prior or subsequent to administration of a Conjugate.

A chemotherapeutic agent can be administered over a series of sessions. Any one or a combination of the chemotherapeutic agents listed below can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, methods of treatment of cancer with a Conjugate are provided as an alternative to chemotherapy or radiation therapy where the chemotherapy or the radiation therapy has proven or can prove too toxic, e.g., results in unacceptable or unbearable side effects, for the patient being treated. The patient being treated can, optionally, be treated with another cancer treatment such as surgery, radiation therapy or chemotherapy, depending on which treatment is found to be acceptable or bearable.

The Conjugates also can be used in an in vitro or ex vivo fashion, such as for the treatment of certain cancers, including, but not limited to, leukemias and lymphomas, such treatment involving autologous stem cell transplants. This can involve a multi-step process in which the animal's autologous hematopoietic stem cells are harvested and purged of cancer cells, the animal's remaining bone-marrow cell population is then eradicated via the administration of a high dose of a Conjugate with or without accompanying high dose radiation therapy, and the stem cell graft is infused back into the animal. Supportive care is then provided while bone marrow function is restored and the animal recovers.

Methods for treating drug resistant cancer include administering to a patient in need thereof an effective amount of a Conjugate and optionally another therapeutic agent that is an anti-cancer agent. Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin C, dacarbazine, procarbizine, topotecan, nitrogen mustards, cytoxan, etoposide, 5-fluorouracil, floxuridine, doxifluridine, and ratitrexed, BCNU, irinotecan, a camptothecin, bleomycin, doxorubicin, idarubicin, daunorubicin, dactinomycin, plicamycin, mitoxantrone, asparaginase, vinblastine, vincristine, vinorelbine, paclitaxel, and docetaxel.

In one aspect, the anti-cancer agent includes, but is not limited to, one or more of the following drugs.

Examples of chemotherapeutic agents include alkylating agents such as thiotepa and CYTOXAN® cyclosphosphamide; alkyl sulfonates such as busulfan, improsulfan, pipo-sulfan and treosulfan; decarbazine; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); a dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide or uracil mustard; nitrosureas such as carmustine, chlorozotocin, fotemustine, lomustine, nimustine, and ranimnustine; bisphosphonates such as clodronate; antibiotics such as the enediyne antibiotics (e.g., calicheamicin, especially calicheamicin gammal I and calicheamicin omegall (see, e.g., Agnew, 1994, Chem. Intl. Ed. Engl. 33: 183-186) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins (e.g., bleomycin A2, bleomycin B2 and peplomycin), cactinomycin, carabicin, caminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, tiazofurin, ribavarin, EICAR, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; a folic acid replenisher such as folinic acid (leucovorin); aceglatone; anti-folate antineoplastic agents such as ALIMTA®, LY231514 pemetrexed, dihydrofolate reductase inhibitors such as methotrexate and trimetrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEXRM, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; deferoxamine; lentinan; lonidainine; a maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; cytosine arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); epipodophyllins such as etoposide (VP-16), teniposide, tepotecan, 9-aminocamptothecin, camptothecin and crisnatol; ifosfamide; mitoxantrone; vinca alkaloids such as vincristine (ONCOVIN®), vindesine, vinca alkaloid, and vinorelbine (NAVELBINE®); novantrone; edatrexate; daunomycin; aminopterin; xeloda; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Also included are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, megestrol, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, leuprolide acetate, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; vitamin DA analogs such as EB 1089, CD 1093 and KH 1060; and pharmaceutically acceptable salts, acids or derivatives of any of the above.

In additional embodiments, the agent can be a photodynamic agent such as vertoporfin (BPD-MA), phthalocyanine, photosensitizer Pc4, demethoxy-hypocrellin A (2BA-2-DMHA); a cytokine such as Interferon-α, Interferon-γ or tumor necrosis factor; Gemcitabine, Velcade™ (bortezomib), Revlamid™ (lenalidomide) or Thalamid; Lovastatin; 1-methyl-4-phenylpyridinium ion; staurosporine; an actinomycin such as Actinomycin D or dactinomycin; an Anthracyclines such as daunorubicin, doxorubicin (adriamycin), idarubicin, epirubicin, pirarubicin, zorubicin and mtoxantrone; and MDR inhibitors such as verapamil and a Ca2+ ATPase inhibitors such as thapsigargin; and pharmaceutically acceptable salts, acids or derivatives of any of the above.

The invention is further described in the following examples, which are not intended to limit the scope of the invention.

EXAMPLES

Example 1

Cell lines expressing CD71 (transferrin receptor) or Lewis Y antigen were treated with antibody drug conjugates (ADCs). The ADCs were composed of antibodies, OKT-9 for CD71 and cBR96 for Lewis Y antigen, linked to MMAF or doxorubicin by a linker, "val-cit" (maleimidocaproyl-valine-citrulline-p-aminobenzyloxycarbonyl-; also referred to as "vc"). Each ADC contained an average of 8 drugs per mAb. When delivered as an ADC using either antibody, MMAF retained its ability to kill drug resistant cell lines. The doxorubicin-based ADC was ineffective at killing the resistant cell lines. ADCs carrying valcit-MMAF molecules are therefore capable of selectively targeting and killing drug resistant cells as well as sensitive cells.

Cell Lines.

The following parental and drug resistant cell lines were used to determine their MMAF-drug sensitivity. The resistant cell lines exhibit P-gp-mediated drug resistance.

TABLE 2

Parental and Drug-Resistant Cell Lines

| Parent:Drug Resistant Progeny* | Source |
| --- | --- |
| A2780:A2780adr | Ovarian Cancer |
| MES-SA:MES-SA/Dx5 | Uterine Sarcoma |
| NCI-H69:NCI-H69/LX-4 | Small Cell Lung Cancer |
| HL60:HL60/RV | Acute Myeloid Leukemia |
| NA:HCT-15 | Colon Carcinoma |
| NCI/ADR-RES:NA | Genetically Similar to Ovarian Carcinoma Cell Line |
| A2780:OVCAR-8 :NA | Human Ovarian Carcinoma |

*NA indicates the cell line (either parent or progeny) was not used.

Testing for Drug Sensitivity.

The activity of various drugs against parental and drug resistant subline pairs was tested. The pairs of cell lines tested were A2780 and A2780adr; MES-SA and MES-SA/Dx5; NCI-H69 and NCI-H69/LX-4; and HL60 and HL60/RV. Cell lines were plated and incubated 24 hr. Culture medium containing serial dilutions of the drugs doxorubicin, vincristine, cisplatin, dolastatin 10 or MMAF were then added. The cultures were incubated to 96 hr and labeled with resazurin. Sensitivity to each drug was measured by determining the $IC_{50}$ of the parent and drug resistant subline pair. The drug resistance (as "fold resistance") was determined from the $IC_{50}$ value of the resistant cell line divided by the $IC_{50}$ value of the parental line; Mean fold resistance is the average across the cell line panel. The results are shown in Table 3.

TABLE 3

Comparison of Drug Sensitivities Between Parental and Drug Resistant Cell Line Pairs

| Drug | Cell Line Pair (Fold Resistance) | | | | |
|---|---|---|---|---|---|
| | A2780adr A2780 | MES-SA/ Dx5 MES-SA | NCI-H69/ LX4 NCI-H69 | HL60/ RV HL60 | Mean Fold Resistance |
| Doxorubicin | 137 | 83 | 103 | 24 | 88 |
| Vincristine | 2000 | 284 | 56888 | 258 | >260 |
| Cisplatin | 2.7 | 1.6 | 4.7 | 13 | 5.5 |
| Dolastatin 10 | 500 | 8275 | ND | ND | >500 |
| MMAF | 7.5 | 3 | 4 | 6 | 5 |

Referring to Table 3, the sensitivity or resistance of the cell line pairs is shown. For the drugs doxorubicin, vincristine and dolastin, the parental cell lines were significantly (at least 24 fold) more sensitive to the drug than the resistant subline pair. In contrast, for the drugs cisplatin and MMAF, the difference in sensitivity of the parent and resistant line was thirteen fold or less.

Alteration of Drug Potency by Verapamil.

Verapamil is a known inhibitor of the P-gp transporter. The following study was conducted to measure the effect of verapamil on P-gp-mediated transport of doxorubicin, vincristine, cisplatin and MMAF.

HCT-15 (colon carcinoma) cells were plated and allowed to adhere to the plates. Neat culture medium or medium containing 40 μM verapamil was added, and the cultures were incubated for 4 hr. Serial dilutions of doxorubicin, vincristine, cisplatin or MMAF were then added. The cultures were incubated to 96 hr and labeled with resazurin. Referring to Table 4, the values shown are the $IC_{50}$ determined from 4-parameter curve fits. The fold difference was determined by dividing the $IC_{50}$ of the drug alone treatment by that of the verapamil plus drug treated cultures.

TABLE 4

Effect of Inhibition of P-gp Mediated Drug Resistance

| | Culture Conditions ($IC_{50}$) | | |
|---|---|---|---|
| Molecule | Alone | +10 μM Verapamil | Fold Difference |
| Doxorubicin | 335 nM | 62 nM | 5.4 |
| Vincristine | 70 nM | <0.001 nM | >10,000 |
| Cisplatin | 5.5 mM | 4.8 mM | 1.04 |
| MMAF | 1000 nM | 174 nM | 5.7 |

As shown in Table 4, addition of verapamil to the culture medium dramatically increased sensitivity to vincristine, a known substrate for P-gp. In contrast, the sensitivity to doxorubicin, cisplatin and MMAF was only slightly enhanced by verapamil, suggesting that these drugs are poor substrates for P-gp.

Effect of Antibody Drug Conjugates of MMAF or Doxorubicin on Cell Lines.

HCT-15 (colon carcinoma) cells were plated and allowed to adhere. Neat culture medium or medium containing 40 μM verapamil was added and cultures were incubated 4 hr. The target cell surface antigens were CD71 (transferrin receptor) and Lewis Y antigen. ADCs were synthesized using OKT-9 as the anti-CD71 mAb and cBR96 as the mAb against anti-Lewis Y antigen, "vc" (maleimidocaproyl-valine-citrulline-p-aminobenzyloxycarbonyl-) as the linker, and MMAF and doxorubicin as the drugs. Each ADC had approximately 8 drugs/mAb. Serial dilutions of the ADCs were added to the cultures.

The cultures were incubated to 96 hr and labeled with resazurin. Referring to Table 5, the values shown are the $IC_{50}$ determined from 4-parameter curve fits. The fold difference was calculated by dividing the $IC_{50}$ of the drug treatment alone by that of the verapamil plus drug treated cultures.

TABLE 5

Drug Sensitivity of HCT-15 to MMAF Antibody Drug Conjugates

| | Culture Conditions ($IC_{50}$) | | |
|---|---|---|---|
| | ADC Only | ADC + 10 μM Verapamil | Fold Difference |
| mOKT9-vcMMAF | 67 ng/mL | 22 ng/mL | 3.0 |
| cBR96-vcMMAF | 13 ng/mL | 4.7 ng/mL | 2.8 |
| cBR96-vcDoxorubicin | 83 mg/mL | 3.4 mg/mL | 24.0 |

When delivered as an ADC using an antibody against either CD71 (mOKT-9) or Lewis Y antigen (cBR96), MMAF demonstrated an ability to kill drug resistant cell lines. This drug resistance was not significantly enhanced by the presence of verapamil. The doxorubicin based ADC was ineffective at killing the resistant cell line, exhibiting an $IC_{50}$ at least 1000 greater than that of the MMAF ADC. The effect of OKT9-vc-doxorubicin ADC, which showed no activity in the presence or absence of verapamil, is not included in the table. Verapamil was much less effective at increasing MMAF-ADC-mediated cell toxicity, as compared with doxorubicin-ADC-mediated toxicity.

Effect of Antibody Drug Conjugates of MMAF or Doxorubicin on a Parental and P-glycoprotein-expressing Cell Lines.

NCI-H69 (parent) and NCI-H69/LX4 (drug resistant) cell lines (small cell lung carcinoma) were plated and incubated for 24 hr. Serial dilutions of the ADCs mOKT9-vcMMAF, cBR96-vcMMAF or cBR96-vcDoxorubicin were then added. The cultures were incubated to 6 days, then labeled with resazurin during the last 24 hr. Referring to Table 6, the values are the $IC_{50}$ in mg/mL determined from 4-parameter curve fits. The fold difference was calculated by dividing the $IC_{50}$ of the NCI-H69/LX4 cell line by that of the NCI-H69 cell line.

TABLE 6

Drug Sensitivity of Cell Line Pairs to MMAF Antibody Drug Conjugates

| | Cell Line ($IC_{50}$) | | |
|---|---|---|---|
| ADC | NCI-H69 | NCI-H69/LX4 | Fold Difference |
| mOKT9-vcMMAF | 0.2 | 0.8 | 4 |
| cBR96-vcMMAF | 0.9 | 0.5 | 0.6 |
| cBR96-vcDoxorubicin | 150 | >600 | ND |

"ND" means not determined.

When delivered as an ADC using mOKT-9 or cBR96, MMAF demonstrated a comparable or slightly enhanced ability to kill drug the resistant cell line NCI-H69/LX4, as compared to the parent cell line (Table 6, middle columns). In contrast, the doxorubicin-based ADC was significantly less effective at killing the resistant cell line.

Comparison of Cell Killing Mediated by Free Drugs or MMAF-ADCs.

NCI/ADR-RES cells were plated and allowed to adhere. Neat culture medium or medium containing 40 µM verapamil was added, and the cultures were incubated for 4 hr. Serial dilutions of the free drugs (doxorubicin, cisplatin, or MMAF) or MMAF ADCs (cBR96-vcMMAF or mOKT9-vcMMAF) were then added. The cultures were incubated to 96 hr and labeled with resazurin. Referring to Table 7, the values are the $IC_{50}$ in mM (doxorubicin, cisplatin, MMAF) or mg/mL (cBR96-vcMMAF, mOKT9-vcMMAF) determined from 4-parameter curve fits. The fold difference is determined by dividing the $IC_{50}$ from the drug alone treatment by that of the drug treated plus verapamil cultures.

TABLE 7

Comparison of Cell Killing Mediated by Free Drugs or MMAF-ADCs

| Drug | Culture Conditions ($IC_{50}$) | | |
|---|---|---|---|
| | Drug or ADC Only | (Drug or ADC) + 10 µM Verapamil | Fold Difference |
| Doxorubicin | 10 | 0.56 | 17.9 |
| Cisplatin | 2.9 | 3.3 | 0.88 |
| MMAF | 0.45 | 0.07 | 6.4 |
| cBR96-vcMMAF | 1.9 | 0.93 | 2 |
| mOKT9-vcMMAF | 0.27 | 0.12 | 2.2 |

The cytotoxicity of the free drug cisplatin was largely unaffected by addition of the P-gp inhibitor verapamil. The cytotoxicity of MMAF increased to some extent in the presence of verapamil. In contrast, the toxicity of doxorubicin markedly increased in the presence of verapamil. As shown above, when MMAF was introduced as an ADC (cBR96-vcMMAF or mOKT9-vcMMAF), its toxicity was only marginally enhanced in the presence of verapamil.

In summary, this study demonstrates that MMAF is a poor substrate for the P-gp transporter. Antibody drug conjugates carrying vc-MMAF molecules are capable of selectively targeting and killing P-gp overexpressing cell lines (drug resistant) as well as parental cell lines. This effect is independent of antigen system and represents a new method for eradicating drug resistant tumors in patients.

Example 2

MMAF is an antimitotic auristatin derivative with a charged C-terminal phenylalanine residue that attenuates its cytotoxic activity, most likely due to impaired intracellular access. In vitro cytotoxicity studies indicated that mAb-maleimidocaproyl-valine-citrulline-p-aminobenzyloxycarbonyl-MMAF (mAb-L1-MMAF) conjugates showed >2,200-fold more anti-proliferative activity than free MMAF on a large panel of CD30 positive hematologic cell lines. MMAF ADCs induced complete and partial regressions of established xenograft tumors at well tolerated doses. To further optimize the ADC, several linker variants were generated in which various components within the L1 linker were either altered or deleted. One of the linkers contained a non-cleavable maleimidocaproyl (L4) spacer between the drug and the mAb. cAC10-L4-MMAF was approximately as potent in vitro as AC10-L1-MMAF against a large panel of cell lines, and was equally potent in vivo. AC10-L4-MMAF was tolerated at >3 times the MTD of AC10-L1-MMAF. LC/MS studies indicated that drug released from AC10-L4-MMAF was the cysteine-L4-MMAF adduct, which likely arises from mAb degradation within the lysosomes of target cells. This linker technology appears to be ideally suited for drugs that are both relatively cell-impermeable and tolerant of substitution with amino acids.

Procedures and Materials

General.

Unless otherwise noted, materials were obtained from commercial suppliers in the highest purity grade available and used without further purifications. Anhydrous DMF and $CH_2Cl_2$ were purchased from Aldrich. N-Fmoc-L-[ring-$^{13}C_6$]-Phenylalanine was obtained from Cambridge Isotope laboratories, Inc. (Andover, Mass.). 2-Chlorotrityl chloride resin was purchased from Advanced ChemTech and loaded with N-Fmoc-L-[ring-$^{13}C_6$]-phenylalanine according to manufacture's specifications. Phenylalanine-2-chlorotrityl resin was purchased from Novabiochem. The phenylalanine loading level of the resin was determined (0.55 mmol/gram) by extensive acylation with Fmoc-Cl followed by spectrophotometric Fmoc-quantitation assay. Solid phase synthesis was performed in plastic syringes (National Scientific Company) fitted with a filter cut out of fritware PE medium grade porous sheet (Scienceware). A Burrell wrist action® shaker (Burrell Scientific, Pittsburg, Pa.) was used for agitation. All solid-phase yields reported are based upon the initial phenylalanine substitution level of the resin and constitute a mass balance of isolated pure material from support, unless otherwise stated. Fmoc-Dap was custom synthesized by Albany Molecular Research, Inc. (Albany, N.Y.).

The structures of the linkers and drugs used in this example are shown in FIG. 1.

HPLC assays were performed using a C12 Phenomenex Synergy MAX-RP 4µ, 80 Å reversed-phase column, 150×2.0 mm. The eluent was a linear gradient of acetonitrile from 5% to 95% in 5 mM aqueous ammonium phosphate, pH 7.0, in 10 min, then 95% acetonitrile for 10 min, flow rate 1 mL/min, 215 nm detection. Preparative HPLC purifications were performed on a Varian instrument equipped with a C12 Phenomenex Synergy MAX-RP 4µ reversed phase column, 250×21.2 mm, and eluting with 0.1% TFA in a water-acetonitrile gradient. Flash chromatography was carried out using Whatman 60 Å 230-400 mesh ASTM silica gel.

Low resolution mass spectra (LCMS) were recorded on a ZMD-Micromass Single Quadrupole Mass Spectrometer equipped with an electrospray ion source (45 eV) coupled with HP1100 HPLC system (reverse phase C12 Phenomenex column, 4µ, 100 Å, 150×2.0 mm). The eluent was a linear gradient of acetonitrile from 5% to 95% in water in the presence of 0.1% formic acid in 10 min, then 95% acetonitrile for 5 min, flow rate 400 µL/min). High resolution (exact mass) electrospray ionization data were obtained at the University of Washington Medicinal Chemistry Mass Spectrometry Center on a Bruker APEXIII 47e [FT(ICR)]MS. NMR data were recorded on Varian Mercury 400 MHz Instrument. Chemical shifts (δ) are reported in ppm downfield from an internal solvent peak; J values are in hertz.

The chimeric $IgG_1$ cAC10 (Wahl et al., 2002, Cancer Res. 62:3736-42) and cBR96 (Trail et al., 1993, Science 261:212-5) mAbs recognize the CD30 and Lewis Y antigens, respectively. The human lymphoma cell lines Karpas 299, SUP-M2, SU-DHL-1, SR-786, DEL, HDLM-2, L428, KMH-2 and WSU-NHL were obtained from the DSMZ (Braunschweig, Germany). 786-O and Caki-1 renal cell carcinoma and HH lymphoma cell lines were purchased from the ATCC (Manassas, Va.). H3396 breast carcinoma cells were obtained as described earlier (Wahl et al., supra). The parent/drug resistant cell line pair NCI-H69, NCI-H69/LX4 was obtained from the ECACC (Salisbury, England), and the Hodgkin's disease cell line L540cy has been previously described (Reeve et al., 1989, Br. J. Cancer 60:339-42). All cell lines were grown according to the manufacturers' recommendations and routinely checked for mycoplasma contamination.

Maleimidocaproyl-MMAE (L4-MMAE).

To a solution of MMAE (Doronina et al., 2003, Nat. Biotechnol. 21:778-84) (72 mg, 0.1 mmol) in anhydrous $CH_2Cl_2$ (2 mL) 6-maleimidocaproic acid (30 mg, 0.15 mmol, 1.5 equiv) was added followed by DEPC (36 µl, 0.2 mmol, 2 equiv) and DIEA (55 µl, 0.3 mmol, 3 equiv). The reaction mixture was stirred at room temperature for 2 h. $CH_2Cl_2$ (30 mL) was added, and the mixture was washed with 10% aqueous citric acid (2×20 mL), water (20 mL), brine (20 mL) and concentrated to near dryness. Product was isolated by flash chromatography on silica gel eluting with 5% MeOH in $CH_2Cl_2$ to give a white solid 32 mg (35%). Reversed-phase HPLC analysis: 98% at 9.48 min. $^1$H NMR (DMSO-$d_6$): δ 0.70-0.89 (18H, m), 0.95-1.05 (6H, m), 1.19-1.34 (m), 1.44-1.55 (m), 1.66-1.84 (m), 1.88-2.02 (m), 2.06-2.16 (m), 2.22-2.46 (m), 2.81 (s), 2.86 (s), 2.90 (s), 2.93 (s), 2.97 (d), 3.01-3.08 (m), 3.12 (d), 3.17 (d), 3.20 (d), 3.23 (dd), 3.35-3.40 (m), 3.42-3.50 (m), 3.52-3.59 (m), 3.77 (d), 3.93-4.04 (m), 4.37-4.54 (m), 4.59-4.64 (m), 4.70-4.78 (m), 5.36 (d), 5.43 (d), 7.01-7.02 (2H, m), 7.14-7.31 (5H, m), 7.65 (d), 7.74 (d), 7.78 (d), 7.89-7.92 (m), 8.56-8.61 (m). HRMS (ESI) calcd for $C_{49}H_{79}N_6O_{10}$ $(MH^+)^+$ 911.5858; found, m/z 911.5839.

Fmoc-MMAF-OMe.

Fmoc-MeVal-Val-Dil (Doronina et al., supra) (0.50 g, 0.78 mmol) and Dap-Phe-OMe.HCl (Doronina et al., supra) (0.30 g, 0.78 mmol) were dissolved in $CH_2Cl_2$ (5 mL) followed by the addition of DIEA (0.30 mL, 1.71 mmol, 2.2 equiv). DEPC (0.20 mL, 1.17 mmol, 1.5 equiv) was added next while the contents stirred under Argon (Ar). The reaction was complete according to HPLC analysis after 1 h. The mixture was concentrated and purified on silica gel eluting with a step gradient of EtOAc (from 50% to 100%) in hexane to provide a white foam 0.65 g (87%). Reversed-phase HPLC analysis: 95% at 16.2 min. $^1$H NMR (DMSO-$d_6$): δ 0.71-0.95 (20H, m), 1.01-1.07 (3H, dd), 1.22-1.30 (m), 1.34-1.52 (m), 1.60-1.83 (m), 1.92-2.11 (m), 2.16-2.28 (2H, m), 2.31-2.42 (m), 2.79-2.89 (m), 2.96-3.07 (m), 3.15-3.16 (m), 3.19 (s), 3.24 (s), 3.29 (d), 3.42-3.55 (m), 3.63 (1.5H, s), 3.66 (1.5H, s), 3.75 (0.51-1, d), 3.96 (1H, m), 4.09-4.11 (m), 4.21-4.51 (m), 4.61-4.74 (m), 7.15-7.23 (5H, m), 7.31 (2H, t), 7.41 (3H, t), 7.62 (2H, d), 7.89 (2H, d), 8.05 (0.5H, d), 8.11 (0.5H, d), 8.29 (0.5H, d), 8.51 (0.5H, d). LCMS (ESI): m/z 968.35 $(MH)^+$ (eluted at 14.84 min).

MMAF-OMe.

Fmoc-MMAF-OMe (140 mg, 0.14 mmol) in $CH_2Cl_2$ (5 mL) was treated with diethylamine (2 mL). After 2 h, the reaction was concentrated and purified by preparative HPLC to give a TFA salt of MMAF-OMe as a white solid, 126 mg (98%). Reversed-phase HPLC analysis: 94% at 11.25 min. $^1$H NMR (DMSO-$d_6$): δ 0.77 (3H, m), 0.87-1.07 (19H, m), 1.22-1.32 (m), 1.37-1.52 (m), 1.60-1.88 (m), 1.96-2.12 (m), 2.18-2.29 (m), 2.32-2.54 (m), 2.83-2.90 (m), 2.99 (s), 3.07 (s), 3.16-3.20 (m), 3.26 (s), 3.42-3.58 (m), 3.64 (s), 3.66 (s), 3.75 (d), 3.98 (m), 4.43-4.52 (m), 4.55-4.76 (m), 7.17-7.58 (5H, m), 8.30 (0.5H, d), 8.56 (0.5H, d), 8.83-8.93 (3H, m). HRMS (ESI) calcd for $C_{40}H_{68}N_5O_8$ $(MH)^+$ 746.5068; found, m/z 746.5037.

Maleimidocaproyl-Val-Cit-PABC-MMAF-OMe (L1-MMAF-OMe).

MMAF-OMe.TFA (110 mg, 0.13 mmol, 1.0 equiv), maleimidocaproyl-Val-Cit-PAB-OCO-pNP (Dubowchik et al., 2002, Bioconjug. Chem. 13:855-69) (103 mg, 0.14 mmol, 1.1 equiv), and HOBt (3.4 mg, 26 µmol, 0.2 equiv) were dissolved in pyridine (0.5 mL) and DMF (2 mL) under Ar. To this mixture was added DIEA (22.5 µL, 0.13 mmol, 1.0 equiv). The resulting solution stirred for 3 h before more DIEA (22.5 µL) was added. After stirring for 40 h total, the mixture was concentrated, taken up in DMSO (2 mL). Preparative HPLC purification followed by precipitation from $CH_2Cl_2$ (2 mL) with ether resulted in 90 mg (52%) of white solid. Reversed-phase HPLC analysis: 95% at 9.48 min. $^1$H NMR (DMSO-$d_6$): δ 0.72-0.94 (28H, m), 1.02-1.06 (3H, dd), 1.14-1.52 (m), 1.54-1.82 (m), 1.90-2.38 (m), 2.28-2.46 (m), 2.85 (br s), 2.97 (s), 3.04 (s), 3.16 (s), 3.18 (s), 3.20 (s), 3.25 (s), 3.28-3.30 (m), 3.42-3.58 (m), 3.63 (s), 3.66 (s), 3.75 (d), 3.96 (m), 4.17-4.21 (m), 4.23-4.28 (m), 4.32-4.42 (m), 4.44-4.55 (m), 4.60-4.74 (m), 4.94-5.12 (m), 6.01 (1H, br s), 7.01 (2H, s), 7.18-7.32 (9H, m), 7.58 (2H, m), 7.81 (1H, d), 8.07-8.12 (1.5H, m), 8.29 (1H, m), 8.51 (0.5H, d), 10.0 (1H, d). HRMS (ESI) calcd for $C_{69}H_{106}N_{11}O_{16}$ $(MH)^+$ 1344.7819; found, m/z 1344.7776.

Maleimidocaproyl-PAB-OCO-pNP.

To a suspension of 6-maleimidocaproic acid (1.0 g, 4.52 mmol) in $CH_2Cl_2$ (13.0 mL) was added p-aminobenzyl alcohol (1.11 g, 9.04 mmol, 2.0 equiv) and EEDQ (2.24 g, 9.04 mmol, 2.0 equiv). The reaction mixture was stirred at ambient temperature for 16 h, and then concentrated to near dryness. The residue was purified by flash chromatography on silica gel, eluting with a step gradient from 25 to 100% ethyl acetate in hexane, to give 1.38 g (96%) of maleimidocaproyl-PABOH as a white solid. Maleimidocaproyl-PABOH (0.85 g, 2.69 mmol) was then activated by reaction with bis p-nitrophenyl carbonate (2.45 g, 8.07 mmol, 3 equiv) and DIEA (0.94 mL, 5.38 mmol, 2 equiv) in DMF (10 mL). After 1 hour, HPLC analysis indicated complete consumption of starting material. Solvent was removed under reduced pressure, and the residue was triturated with diethyl ether (5×20 mL) resulting in 1.25 g (96%) of an off white solid. Reversed-phase HPLC analysis: 99% at 9.98 min. $^1$H NMR (CDCl$_3$): δ 1.37 (2H, m), 1.64 (2H, m), 1.77 (2H, m), 2.37 (2H, t, J=7.6), 3.54 (2H, t, J=7.2), 6.68 (2H, s), 7.37 (2H, d, J=9.2), 7.41 (2H, d, J=8.8), 7.57 (2H, d, J=8.8), 8.27 (2H, d, J=9.2).

MeVal-Val-Dil-Dap-Phe-2-chlorotrityl resin.

Fmoc-Dap (450 mg, 1.1 mmol) and HATU (418 mg, 1.1 mmol, 2 equiv) were dissolved in anhydrous DMF (8 mL), and DIEA (384 µl, 2.2 mmol, 4 equiv). The resulting solution was added to the 20 mL syringe containing Phe-2-chlorotrityl resin (1 g, 0.55 mmol). The mixture was agitated for 3 h. Reaction completion was determined by LCMS analysis of material cleaved off a small amount of resin. The resin was filtered, washed with DMF (6×10 mL), $CH_2Cl_2$ (6×10 mL), ethyl ether (6×10 mL), and dried in vacuo for 2 h. A 20% piperidine in DMF solution (5 mL) was added to the syringe, and the mixture was agitated for 2 h. The resin was then filtered, rinsed with DMF (6×10 mL), $CH_2Cl_2$ (6×10 mL), ethyl ether (6×10 mL), and dried in vacuo. In a separate flask Fmoc-MeVal-Val-Dil tripeptide (Doronina et al., supra) (702 mg, 1.1 mmol), HATU (418 mg, 1.1 mmol, 2 equiv) were dissolved in anhydrous DMF (8 mL) followed by the addition of DIEA (384 µl, 2.2 mmol, 4 equiv). The solution was then transferred to the syringe containing the resin, and the mixture was agitated for 3 h. LCMS analysis of material cleaved from a small amount of resin was used to determine reaction completion. The resin was filtered, washed with DMF (6×10 mL), $CH_2Cl_2$ (6×10 mL), ethyl ether (6×10 mL), and dried in vacuo for 2 h. A 20% piperidine solution in DMF (5 mL) was added to the resin, and the mixture was agitated for 2 h. The resin was then filtered, washed with DMF (6×10 mL), $CH_2Cl_2$ (6×10 mL), ethyl ether (6×10 mL), and dried in vacuo.

MMAF (MeVal-Val-Dil-Dap-Phe).

MeVal-Val-Dil-Dap-Phe-2-chlorotrityl resin (100 mg, 0.044 mmol) in a 5 mL syringe was treated with 2% TFA in $CH_2Cl_2$ (4 mL) for 5 min at ambient temperature. Preparative HPLC purification provided 27 mg (73%) of white solid. Reversed-phase HPLC analysis: 95% at 5.74 min. $^1$H NMR (DMF-$d_7$): δ 0.78 (3H, t), 0.90-1.15 (19H, m), 1.28-1.44 (m), 1.46-1.62 (m), 1.75-2.00 (m), 2.03-2.12 (m), 2.14-2.23 (m), 2.24-2.48 (m), 2.50-2.61 (m), 2.78-2.82 (m), 2.97-3.09 (m), 3.12 (s), 3.18-3.21 (m), 3.26 (d), 3.30 (s), 3.34 (s), 3.41-3.46 (m), 3.49 (d), 3.53-3.60 (m), 3.61-3.69 (m), 3.72-3.78 (m), 3.93 (d), 4.10 (2H, br d), 4.12-4.38 (1H, br), 4.64-4.92 (3H, m), 7.21-7.35 (5H, m), 8.12 (0.5H, d), 8.40 (0.5H, d), 8.78-8.83 (1H, m), 9.03 (1H, br s), 9.63 (1H, br s). HRMS (ESI) calcd for $C_{39}H_{66}N_5O_8$ (MH)$^+$ 732.4911; found, m/z 732.4890.

Maleimidocaproyl-Val-Cit-PABC-MMAF (L1-MMAF).

MeVal-Val-Dil-Dap-Phe-2-chlorotrityl resin (120 mg, 0.053 mmol) in 5 mL syringe was treated with a solution of maleimidocaproyl-Val-Cit-PAB-OCOpNP (313 mg, 0.42 mmol, 8 equiv), HOAt (2 mg, 0.015 mmol, 0.3 equiv) and DIEA (148 µL, 0.84 mmol, 16 equiv) in DMF (4 ml) for 16 h. The resin was then filtered, washed with DMF (6×3 mL), $CH_2Cl_2$ (6×3 mL), and ethyl ether (6×3 mL). Cleavage from resin by treatment with 2% TFA in $CH_2Cl_2$ (4 mL) for 5 min and preparative HPLC purification of the released material generated 15 mg (21%) of white solid that was 98% pure by reversed-phase HPLC analysis (retention time 7.20 min). $^1$H NMR (DMSO-$d_6$): δ 0.75-0.95 (28H, m), 1.05 (3H, t), 1.14 (m), 1.22-1.53 (m), 1.53-1.80 (m), 1.80-2.40 (m), 2.80 (br s), 2.96 (d), 3.11 (s), 3.13 (s), 3.20 (s), 3.62-3.70 (d), 3.83-3.94 (m), 4.08-4.24 (m), 4.28-4.5 (m), 4.50-4.68 (m), 4.90-5.10 (m), 5.35 (s), 5.96 (1H, t), 7.02 (2H, s), 7.08-7.32 (9H, m), 7.54 (2H, d), 7.80 (d), 8.04-8.12 (m), 8.16-8.33 (m), 10.0 (1H, br s). HRMS (ESI) calcd for $C_{68}H_{104}N_{11}O_{16}$(MH)$^+$ 1330.7663; found, m/z 1330.7665.

Maleimidocaproyl-Val-Cit-MMAF (L2-MMAF).

Fmoc-Cit (140 mg, 0.352 mmol), and Fmoc-Val (60 mg, 0.176 mmol) were coupled sequentially to MeVal-Val-Dil-Dap-Phe-2-chlorotrityl resin (200 mg, 0.088 mmol) using HATU coupling chemistry as described above for MeVal-Val-Dil-Dap-Phe-2-chlorotrityl resin. Then, to the dry Val-Cit-MeVal-Val-Dil-Dap-Phe-2-chlorotrityl resin a solution of 6-maleimidocaproic acid N-hydroxysuccinimide ester (54 mg, 0.176 mmol) in DMF (3 mL) was added. The mixture was shaken at room temperature for 4 h. Cleavage from resin by treatment with 2% TFA in $CH_2Cl_2$ (4 mL) for 5 min provided 28 mg (27%) of white solid after preparative HPLC purification. Reversed-phase HPLC analysis: 98% at 6.16 min. $^1$H NMR (DMF-$d_7$): δ 0.69-0.92 (28H, m), 1.01-1.06 (3H, m), 1.17 (m), 1.42-1.53 (m), 1.53-1.68 (m), 1.70-2.28 (m), 2.28-2.46 (m), 2.74-2.88 (m), 2.89-3.00 (m), 3.04-3.06 (m), 3.15 (s), 3.18 (s), 3.24 (s), 3.40-3.47 (m), 3.48-3.58 (m), 3.59-3.68 (m), 3.71-3.76 (d), 3.96 (m), 4.14 (t), 4.23 (m), 4.38-4.52 (m), 4.58-4.76 (m), 4.89 (m), 5.95 (m), 7.01 (2H, s), 7.17-7.28 (5H, m), 7.77 (m), 7.89 (m), 7.96 (m), 8.04 (m), 8.17 (m), 8.28 (m), 8.38 (d), 8.47 (m). HRMS (ESI) calcd for $C_{60}H_{97}N_{10}O_{14}$ (MH)$^+$ 1181.7186; found, m/z 1181.7164.

Maleimidocaproyl-PABC-MMAF (L3-MMAF).

MeVal-Val-Dil-Dap-Phe-2-chlorotrityl resin (100 mg, 0.044 mmol) was treated with a solution of maleimidocaproyl-PAB-OCO-pNP (42 mg, 0.088 mmol, 2 equiv) and HOBt (1 mg, 9 µmol, 0.1 equiv) and DIEA (30 µL, 0.176 mmol, 4 equiv) in DMF (3 ml) for 16 h. The resin was then filtered, washed with DMF (6×3 mL), $CH_2Cl_2$ (6×3 mL), and ethyl ether (6×3 mL). Cleavage from resin by treatment with 2% TFA in $CH_2Cl_2$ (4 mL) for 5 min followed by preparative HPLC purification provided 31 mg (66%) of white solid which was 99% pure by reversed-phase HPLC analysis (retention time 7.14 min). NMR (DMF-$d_7$): δ 0.76-0.98 (18H, m), 1.04 (2H, d), 1.12 (3H, m), 1.25-1.40 (m), 1.51-1.61 (m), 1.63-1.69 (m), 1.76-1.90 (m), 1.94-2.40 (m), 1.35-2.38 (m), 2.50-2.60 (m), 2.96 (s), 3.10 (s), 3.23 (s), 3.27 (s), 3.30 (s), 3.34 (s), 3.41-3.50 (m), 3.50-3.80 (m), 3.90-4.20 (m), 4.33-4.48 (m), 4.54-4.62 (m), 4.63-4.77 (m), 4.82-4.93 (m), 5.06-5.20 (m), 7.02 (2H, s), 7.36-7.21 (9H, m), 7.70 (2H, d), 8.11 (0.5H, d), 8.36 (0.5H, d), 10.00 (1H, br s). HRMS (ESI) calcd for $C_{57}H_{84}N_7O_{13}$ (MH)$^+$ 1074.6127; found, m/z 1074.6095.

Maleimidocaproyl-MMAF (L4-MMAF).

6-Maleimidocaproic acid (37 mg, 0.176 mmol, 2 equiv), and HATU (67 mg, 0.176 mmol, 2 equiv) were dissolved in anhydrous DMF (3 mL), followed by the addition of DIEA (62 µl, 0.35 mmol, 4 equiv). The solution was then transferred to a 5 mL syringe containing MeVal-Val-Dil-Dap-Phe-2-chlorotrityl resin (200 mg, 0.088 mmol), and the mixture was agitated for 3 h. The resin was filtered, washed with DMF (6×3 mL), $CH_2Cl_2$ (6×3 mL), ethyl ether (6×3 mL), and dried in vacuo. Drug-linker was cleaved off the resin by treatment with 2% TFA in $CH_2Cl_2$ (4 mL) for 5 min and then purified by preparative HPLC to give 57 mg (70%) of white solid. Reversed-phase HPLC analysis: 98% at 6.72 min. $^1$H NMR (DMF-$d_7$): δ 0.78-0.96 (18H, m), 1.04 (2H, t), 1.12 (3H, m), 1.25-1.36 (m), 1.41 (2H, d), 1.46-1.65 (m), 1.73-1.87 (m), 1.88-2.07 (m), 2.08-2.26 (m), 2.32-2.48 (m), 2.48-2.67 (m), 2.79-2.84 (m), 2.96 (d), 3.02 (d), 3.10 (d), 3.23 (d), 3.27 (s), 3.30 (s), 3.34 (s), 3.45 (t), 3.52-3.61 (m), 3.62-3.80 (m), 3.93 (d), 4.09-4.28 (m), 4.54-4.78 (m), 4.82-4.91 (2H, m), 7.03 (2H, s), 7.21-7.35-(5H, m), 7.51 (0.5H, d), 8.11 (0.5H, d), 8.36 (0.5H, d), 8.48 (0.5H, d), 13.0 (br s). HRMS (ESI) calcd for $C_{49}H_{77}N_6O_{11}$ (MH)$^+$ 925.5650; found, m/z 925.5636.

Maleimidocaproyl-[$^{13}$C]MMAF (L4-[$^{13}$C]MMAF)

Maleimidocaproyl-[$^{13}$C]MMAF (L4-[$^{13}$C]MMAF) was prepared as described above starting from N-Fmoc-L-[ring-$^{13}C_6$]-phenylalanine-2-chlorotrityl resin. LCMS (ESI): m/z 931.62 (MH)$^+$.

Preparation of Antibody Drug Conjugates.

The conjugates with 8 drug molecules per antibody were prepared as described previously (Doronina et al., supra; Francisco et al., 2003, Blood 102:1458-65). Briefly, cBR96 or cAC10 were mixed with DTT at 37° C. for 30 min, and the buffer was exchanged by elution through Sephadex G-25 resin with PBS containing 1 mmol/L diethylenetriaminepentaacetic acid. PBS containing 1 mmol/L diethylenetriaminepentaacetic acid was added to reduce mAb final concentration to 2.5 mg/mL. The thiol concentration was ~8.4 thiols/mAb as measured by Ellman's reagent, DTNB. A 9.5-fold molar excess of linker-drug (L1-MMAF, L1-Dox (Dubowchik et al., 2002, supra), L1-MMAE (Doronina et al., supra), or L4-MMAE) was added to the reduced antibody at 4° C. for 1 h, and the conjugation reaction was quenched by adding a 20-fold excess of cysteine. The reaction mixture was concentrated by centrifugal ultrafiltration and buffer-exchanged through Sephadex G-25 equilibrated with PBS at 4° C. The conjugate was then sterile filtered through a 0.2-μm filter.

cAC10 antibody drug conjugates with four drugs per antibody were prepared by partial reduction of the mAb (Hamblett et al., 2004, Clin. Cancer Res. 10:7063-70; Sun et al., 2005, Bioconjug. Chem. 16:1282-90) followed by reaction with desired linker-drug (L1-MMAF, L2-MMAF, L3-MMAF, or L4-MMAF). The antibody cAC10 (10 mg/mL) was partially reduced by addition of 3.0 molar equivalents of DTT at pH 8.0, followed by incubation at 37° C. for ~2 h. The reduction reaction was then chilled to ~10° C., and the excess DTT removed via diafiltration. The thiol concentration was determined by DTNB, and the SH/Ab ratio found to be in the range of 3.8-4.5. The linker-drug was then added to a linker-drug/reduced cysteine molar ratio of ~1.15. The conjugation reaction was carried out in the presence of 15% v/v of DMSO. After conjugation, excess free cysteine (2 mol/L cysteine per mol/L linker-drug) was added to quench unreacted linker-drug to produce the cysteine-linker-drug adduct. The reaction mixture was purified and buffer-exchanged into PBS by diafiltration to obtain the partially loaded cAC10-linker-drug conjugate referred to as cAC10-Lx-MMAF. The molar ratio of drug substitution was determined according to previously published methods (Hamblen et al., supra; Sun et al., supra).

Released Drug Identification.

Lysosomal extracts of L540cy cells were prepared by swelling $2.4 \times 10^8$ cells in 9 mL of 0.25 M sucrose, 1 mM EDTA, and 10 mM HEPES, pH 7.4. After 30 min on ice, cells were Dounce homogenized until >95% were broken as measured by Trypan Blue dye exclusion. Homogenates were centrifuged (3,000×g, 10 min, 4° C.) to pellet cellular debris, the supernatant ($4 \times 10^7$ cell equivalents per tube) transferred to polyallomar ultracentrifuge tubes (13×51 mm), and centrifuged (17,000×g, 15 min, 4° C.) in a TLA100.3 rotor to isolate the lysosome-containing light mitochondrial pellet. Pellets were stored at −80° C. The pellets were thawed and resuspended in 500 μl of 50 mM sodium acetate pH 5.0 and 2 mM DTT. cAC10-L4-[$^{12}$C]MMAF, cAC10-L4-[$^{13}$C]MMAF, and cAC10-L4-[$^{12/13}$C]MMAF (50 μg/mL) were independently added to one pellet. After three freeze/thaw cycles to break open lysosomes, samples were incubated for 24 h at 37° C. Cold methanol (2 vol) was added to precipitate protein, the samples centrifuged at 14,000×g to pellet debris, and 100 μL of supernatant analyzed by low resolution mass spectrometry as described above. Authentic cysteine-L4-MMAF was prepared by treating 100 μM L4-MMAF with 1 mM cysteine in PBS at room temperature for 10 min.

In Vitro Growth Inhibition.

Log phase cultures of cells were collected and cells plated at seeding densities ranging from 500-10,000 cells/well according to pre-determined conditions. After incubating 24 h to allow surface protein reconstitution, serial dilutions of test molecules were added and cultures incubated a further 4-6 days depending on cell line. Assessment of cellular growth and data reduction to generate $IC_{50}$ values was done using Alamar Blue (Biosource International, Camarillo, Calif.) dye reduction assay as previously described, according to previously published methods (Doronina et al., supra; Hamblett et al., supra; Law et al., 2004, Clin. Cancer Res. 10:7842-51; Francisco et al., supra). Briefly, a 40% solution (wt/vol) of Alamar Blue was freshly prepared in complete media just before cultures were added. Ninety-two hours after drug exposure, Alamar Blue solution was added to cells to constitute 10% culture volume. Cells were incubated for 4 h, and dye reduction was measured on a Fusion HT fluorescent plate reader (Packard Instruments, Meriden, Conn.).

In Vivo Therapy Experiments.

For the localized, subcutaneous disease model of anaplastic large cell lymphoma, $5 \times 10^6$ Karpas 299 cells were implanted into the right flanks of C.B.-17 SCID mice. Therapy was initiated when the tumor size in each group of 5 animals averaged approximately 100 mm$^3$. Treatments consisted of a single injection of solutions of the conjugates or controls in PBS intravenously (tail vein). Tumor volume was determined using the formula $(L \times W^2)/2$. For the disseminated ALCL model, $1 \times 10^6$ Karpas 299 were injected in the tail vein into C.B.-17 SCID mice. Single dose injection treatment was performed at 9 days after tumor injection. Mice that developed hind limb paralysis or other signs of significant disease were euthanized in accordance with Animal Care and Use Committee guidelines.

In Vivo Localization of Antibodies via Immunohistochemistry.

When subcutaneous Karpas 299 tumor size reached 300 mm$^3$, three animals per group received one injection of 10 mg antibody component/kg body weight of either cAC10-L1-MMAF$_4$ or cBR96-L1-MMAF$_4$ intravenously. Tumors were then removed and placed in OCT compound (Sakura Finetec, Torrence, Calif.) and 5 μm-thin frozen tissue sections were stained using immunohistochemistry evaluation. Briefly, frozen tissues on the slides were air dried then fixed in 4% paraformaldehyde for 15 min at room temperature. Endogenous peroxidase activity was blocked using 0.6% $H_2O_2$ for 15 min. Additional blocking for endogenous biotin was done using the Avidin-Biotin Blocking kit (Vector Labs). Biotinylated-anti-human-Fc and biotinylated-anti-drug antibodies (both Seattle Genetics) were incubated on tissues at 2 μg/ml concentration for 1 hr at room temperature. Following incubation of slides with avidin conjugated to HRP (Vectastatin Elite ABC kit, Vector Labs), DAB was used as a substrate for HRP. Tissues were counterstained using hematoxylin, slides were dehydrated and coverslipped. Images were taken using the Zeiss Axiovert light microscope.

TUNEL Assay.

Apoptosis was evaluated by TUNEL Staining (In Situ Cell Death Detection Kit, TR Red, Roche Applied Science, Germany) according to the manufacturer's instructions. TUNEL staining was carried out on sections of frozen specimens embedded in OCT. Labeling was visualized by Zeiss Axiovert fluorescence microscopy.

Results

Development of MMAF-Based Conjugates.

The structure of the antimitotic agent MMAE is shown in FIG. 1. This drug has previously displayed $IC_{50}$ values in the range of 1-5 nM on hematologic cell lines (Doronina et al., supra; Law et al., supra), and was designed for mAb-based targeted delivery using peptide based linkers appended to the N-terminal methylvaline residue (Doronina et al., supra; Francisco et al., supra). The synthesis of MMAE proceeded through a solution-phase route involving the coupling of the amino-protected N-terminal trimer to the C-terminal dimer. Due to the convergent nature of the process, it was possible to produce a large number of auristatins with varied solubilities, potencies and pharmacokinetic properties. One molecule that emerged was MMAF-OMe (FIG. 1), a C-terminal phenylalanine containing auristatin that remains one of the most potent drugs isolated so far (Table 8). MMAF-OMe is a prodrug of MMAF (FIG. 1), with the potential of having facilitated intracellular uptake due to the presence of a neutral C-terminus. In addition, intracellular ester hydrolysis of MMAF-OMe should rapidly generate MMAF, a C-terminally charged molecule expected to have impaired membrane translocation capabilities. Therefore, MMAF was synthesized using solid phase synthetic methodology, and as expected was much less potent than MMAE on all cell lines tested (Table 8). In addition, the maximum tolerated dose in mice of MMAF (>16 mg/kg) was much higher than MMAE (1 mg/kg). Thus, MMAF was of great interest for targeted delivery, since the free drug had attenuated potency, lower toxicity, and much higher aqueous solubility compared to MMAE. Facilitated intracellular transport was expected to greatly enhance its activity.

Conjugates of MMAF were produced using the maleimidocaproyl-Val-Cit-PABC linker (L1, FIG. 1) as described earlier for MMAE (Doronina et al., supra; Francisco et al., supra). The mAbs used were BR96 (Trail et al., 1993, supra) and AC10 (Francisco et al., supra), chimeric IgG1 mAbs that bind to the LeY antigen on human carcinomas and the CD30 antigen on hematologic malignancies, respectively. Initial studies were undertaken with conjugates that had 8 drugs/mAb. More recent data demonstrating improved pharmacokinetic and toxicologic properties of conjugates having lower drug loadings (Hamblett et al., supra) prompted investigation of the activities of conjugates with fewer drugs/mAb. These were obtained through carefully controlled mAb disulfide reduction with limiting amounts of dithiothreitol (DTT) sufficient to produce an average of 4 thiol groups/mAb. Alkylation with drugs bearing thiol-reactive maleimide functionalities led to the formation of conjugates having an average of 4 drugs/mAb. The resulting distributions of species were as previously described (Sun et al., supra). It was found that the ability of the parent unmodified mAb to bind to cell-surface receptors was maintained (Doronina et al., supra), and aggregate (<5%) and free drug levels (0.5%) were very low.

TABLE 8

In Vitro Cytotoxicity of Auristatins

| Cell Line | Type | $IC_{50}$ (nM)[a] | | |
|---|---|---|---|---|
| | | MMAE | MMAF | MMAF-OMe |
| Karpas 299 | Anaplastic large cell lymphoma | 0.5 | 119 | <0.001 |
| H3396 | Breast carcinoma | 0.1 | 105 | <0.001 |
| 786-O | Renal cell carcinoma | 2.0 | 257 | 0.01 |
| Caki-1 | Renal cell carcinoma | 0.7 | 200 | <0.001 |

[a]Cells were exposed to the drugs, and the cytotoxic activities were determined 96 h later using Alamar Blue dye conversion as a measure of cell viability.

In Vitro Growth Inhibition.

cAC10-L1-MMAF was tested on a panel of both CD30 positive and negative cell lines as shown in Table 9 (infra). Cells were exposed to the ADCs continuously for 96 h, and the cytotoxic effects, as determined by Alamar Blue conversion, were compared to those of free MMAF. On a molar basis, the cAC10-L1-MMAF$_4$ (the subscript indicating an average of four MMAF molecules per antibody molecule) was an average of >2,200-fold more potent than free MMAF, and was active on all the CD30-positive cell lines tested. The effects were immunologically specific, since WSU-NHL cells, which do not express detectable levels of the CD30 antigen, were unaffected by the conjugate. Limited studies were also undertaken with the cAC10-L1-MMAF-OMe$_4$ based conjugates, and it was found that they displayed $IC_{50}$ values on Karpas 299 (0.04 nM) and L540cy (0.11 nM) cells that were comparable to those of cAC10-L1-MMAF$_4$ (Table 9). This is consistent with the assumption stated earlier that the active form of MMAF-OMe is the free acid MMAF.

Figure 2:
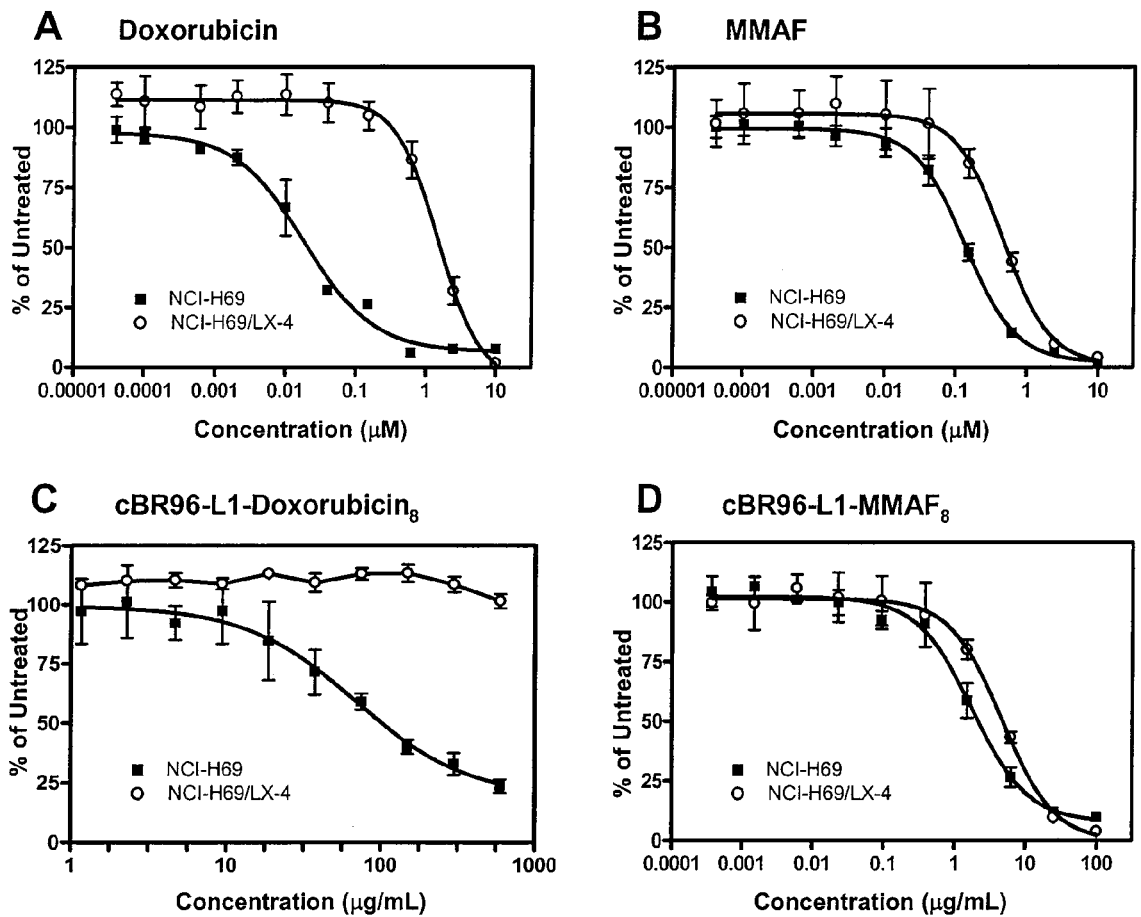
FIG. 2. Cytotoxic effects of drugs (A, B) and cBR96-drug conjugates (C, D) on human small cell lung carcinoma cell line H69 (-■-) and its P-glycoprotein overexpressing counterpart H69/LX-4 (-○-). Both cell lines are Lewis Y positive. The cBR96 antibody specifically binds to the Lewis Y antigen. The cells were incubated with either the drug Doxorubicin (A) or MMAF (B), or anti-Lewis Y antigen antibody-linker-drug conjugate, cBR96-L1-Doxorubicin$_8$ (C) or cBR96-L1-MMAF$_8$ (D) for 6 days, and the cytotoxic effects were determined by metabolism of Alamar Blue during the last 24 h of incubation.

Further studies were undertaken with MMAF and the cBR96-L1-MMAF conjugate on a LeY positive human small cell lung carcinoma cell line (H69), and its P-glycoprotein overexpressing counterpart H69/LX4 (Reeve et al., supra). The results were compared to doxorubicin and cBR96-L1-doxorubicin, a previously described conjugate with 8 doxorubicin molecules/mAb (Trail et al., 1993, supra; Trail et al., 1997, Cancer Res. 57:100-5). H69/LX-4 cells were approximately 100-times less sensitive to doxorubicin compared to the parental cell (FIG. 2A), while there was only a 3-fold difference with MMAF (FIG. 2B). This trend extended to the conjugates, in that the drug resistant cell line was refractory to BR96-L1-doxorubicin (FIG. 2C), but quite sensitive to the corresponding MMAF conjugate (FIG. 2D). These results have been confirmed on several MDR positive cell lines (data not shown), in which it has been found that MMAF and MMAF-based immunoconjugates circumvent common forms of the MDR phenotype.

Linker Technologies.

The linker joining the drug to the mAb carrier plays a significant role in conjugate potency (Wu et al., 2005, Nat. Biotechnol. 23:1137-46; Trail et al., 1997, supra; Chari et al., 1992, Cancer Res. 52:127-31; Hamann et al., 2005a, Bioconjug. Chem. 16:346-53; Hamann et al., 2005b, Bioconjug. Chem. 16:354-60). Peptide linker technology was applied to MMAF, based on its successful application with MMAE (Doronina et al., supra; Hamblett et al., supra; Law et al., supra; Francisco et al., supra; Sun et al., supra), and other drug classes (Dubowchik et al., 1999, Pharmacol. Ther. 83:67-123; Dubowchik et al., 1998, Bioorg. Med. Chem. Lett. 8:3341-6; Dubowchik et al., 2002, supra; Dubowchik et al., 1998, Bioorg. Med. Chem. Lett. 8:3347-52).

To expand the understanding of the role that the linker plays in drug release and cytotoxicity, truncated linker-MMAF derivatives were prepared lacking the p-aminobenzyloxycarbonyl (PABC) self-immolative group (L2, FIG. 1), the peptide (L3), and both the peptide and the PABC group (L4). The resulting modified drugs were attached to cAC10, forming ADCs with approximately 4 drugs/mAb. As expected from earlier work with related doxorubicin ADCs (Dubowchik et al. (1999), supra; Dubowchik et al., 1998, supra; Dubowchik et al., 2002, supra; Dubowchik et al., 1998, supra), cAC10-L2-MMAF$_4$ was devoid of activity on Karpas 299 cells (Table 9). In contrast, both cAC10-L3-MMAF and cAC10-L4-MMAF were highly active, and were as active as the full-length construct (cAC10-L1-MMAF). ADCs with truncated linkers (L2, L3, and L4) were not substrates for human cathepsin B, which was an important design element in forming the original proteolytically cleavable linker technology for doxorubicin ((Dubowchik et al., 1999, supra; Dubowchik et al., 1998, supra; Dubowchik et al., 2002, supra; Dubowchik et al., 1998, supra). The effects of the truncated linkers were drug-dependent, in that cAC10-L4-MMAE had no cytotoxic activity above 50 nM (1000 ng/mL) on Karpas 299 cells.

The results prompted testing of cAC10-L4-MMAF$_4$ on the broad panel of hematologic cell lines shown in Table 9. The conjugate was active against all CD30 positive cell lines tested, and had approximately half the activity of cAC10-L1-MMAF. In addition, the effects were immunologically specific, as CD30 negative SU-NHL cells were not affected by cAC10-L4-MMAF$_4$. Thus, MMAF can be attached to cAC10 through linkers not designed for proteolytic cleavage, without significant loss in potency.

TABLE 9

In Vitro Cytotoxicity of cAC10-MMAF ADCs and Free MMAF

| Cell Line | Tumor Type | IC$_{50}$ (nM)$^a$ | | |
|---|---|---|---|---|
| | | cAC10-L1-MMAF$_4$ | cAC10-L4-MMAF$_4$ | MMAF |
| Karpas 299 | Anaplastic large cell lymphoma | 0.057 | 0.059 | 119 |
| SUP-M2 | Anaplastic large cell lymphoma | 0.023 | 0.024 | 79.7 |
| SU-DHL-1 | Anaplastic large cell lymphoma | 0.007 | 0.045 | 34.7 |
| SR-786 | Anaplastic large cell lymphoma | 0.01 | 0.016 | 38.1 |
| DEL | Anaplastic large cell lymphoma | 0.038 | 0.046 | 69 |
| HH | Cutaneous T-cell lymphoma | 0.016 | 0.022 | 30.7 |
| L540cy | Hodgkin's disease | 0.06 | 0.085 | 70.4 |
| HDLM-2 | Hodgkin's disease | 0.08 | 0.21 | 66 |
| L428 | Hodgkin's disease | 0.021 | 0.058 | 68 |
| KMH-2 | Hodgkin's disease | 0.009 | 0.068 | 45.4 |
| RPMI 6666 | Hodgkin's disease | 0.091 | 0.18 | 164 |
| WSU-NHL | Non-Hodgkin's lymphoma, CD30$^-$ | No effect | No effect | 60.3 |
| Mean (all lines) | | 0.034$^b$ | 0.066$^c$ | 70.4 |

Figure 3:
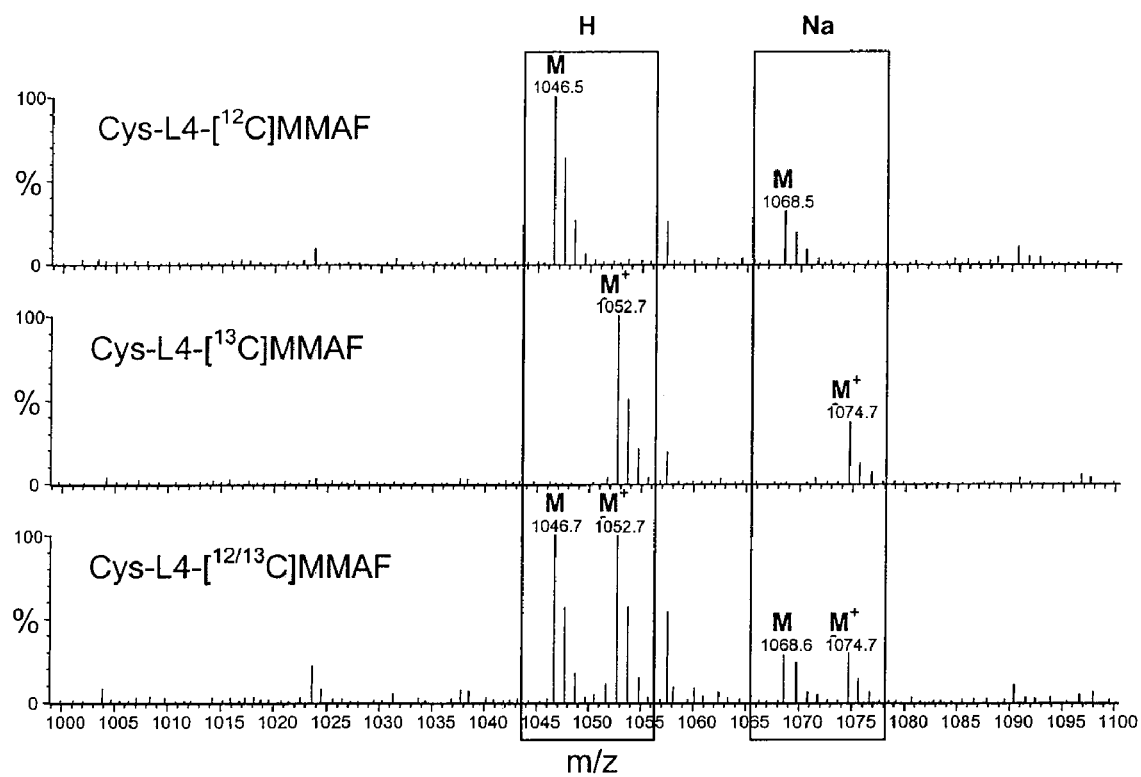
FIG. 3. LC/MS analysis of products released in lysosomal extracts of L540cy cells from cAC10-L4-MMAF conjugate comprised of [$^{12}C_6$-Phe]-MMAF (top), [$^{13}C_6$-Phe]-MMAF (middle), and a 1:1 mixture of these two conjugates (bottom). The fragments obtained from the co-mixture of the conjugates were analyzed for M and M+6 (M$^+$) molecular ion clusters. Cysteine-L4-MMAF, m/z 1046/1052, was the only identifiable MMAF component.

$^a$Cytotoxicity was measured as indicated in Table 1. Concentrations of the ADCs are represented by the drug component
$^b$Represents 1.36 ng/mL mAb component
$^c$Represents 2.64 ng/mL mAb component To determine what drug-related molecule might be released from the conjugate, a $^{13}$C-phenylalanine substituted L4-MMAF was synthesized and conjugated to cAC10. $^{12}$C—, $^{13}$C—, and a 1:1 mixture of $^{12}$C- and $^{13}$C-cAC10-L4-MMAF were then incubated in lysosomal extracts of L540cy cells. Low molecular weight products were separated from proteins and were analyzed by LC/MS. The identification of released drugs was based on the 6 mass unit shifts between the $^{12}$C and $^{13}$C derivatives of the drug. After inspection of mass spectra for such shifts, the only detectable drug related molecule that was found was the cysteine adduct of maleimidocaproyl-MMAF (FIG. 3). To confirm this, a sample of cysteine-L4-MMAF was synthesized, and was shown to have the same elution and LC/MS profile as the drug released from the cAC10-L4-MMAF$_4$ ADC. The mAb is the likely source for cysteine in cysteine-L4-MMAF, since this was the residue to which the drug was attached. Thus, drug release takes place through mAb degradation.

Maximum Tolerated Doses.

The maximum tolerated doses (MTDs) of the cAC10-MMAF conjugates were determined in BALB/c mice and in Sprague-Dawley rats, and are defined as the highest dose that did not induce more than 20% weight loss, distress, or overt toxicities in any of the animals. This dose was generally within 20% of doses where such events took place. cAC10-L1-MMAF$_4$ has an MTD of 50 mg/kg in mice and 15 mg/kg in rats. The corresponding cAC10-L4-MMAF$_4$ ADC was much less toxic, having MTDs in mice and rats of more than 150 mg/kg (the highest dose tested, which resulted in no apparent toxicity) and 90 mg/kg in rats, respectively. This result indicates that the method by which the drug is attached to the mAb can affect ADC tolerability, and the ADC lacking the peptide spacer within the linker was much less toxic than the peptide-based ADC.

Immunohistochemical Analyses.

Studies were undertaken to determine if cAC10-L1-MMAF$_4$ localized into subcutaneous Karpas 299 tumors in nude mice. Animals were injected intravenously with cAC10-L1-MMAF$_4$ or cBR96-L1-MMAF$_4$ at 10 mg antibody component/kg body weight. Tumors were removed 24 h later and frozen sections were evaluated for the presence of the mAb and drug components using immunohistochemistry with biotinylated anti-human-Fc and anti-MMAF mAbs as secondary antibodies respectively. The results showed that cAC10-L1-MMAF$_4$ accumulated much more efficiently within Karpas 299 tumors compared to the cBR96 non-binding control ADC. Both the mAb and drug moieties were detected throughout the tumor, indicating that the ADC was delivered as an intact molecule.

Additional studies were undertaken to determine the effects of ADC localization on apoptosis. The results showed that there were significant levels of fragmented DNA in tumors of animals that received cAC10-L1-MMAF$_4$. This was established by TUNEL analysis, which measured bromodeoxyuridine incorporation into fragmented DNA. A non-binding control ADC did not induce nearly this level of fragmentation, which was consistent with the localization data.

In Vivo Therapy Studies.

Figure 4:
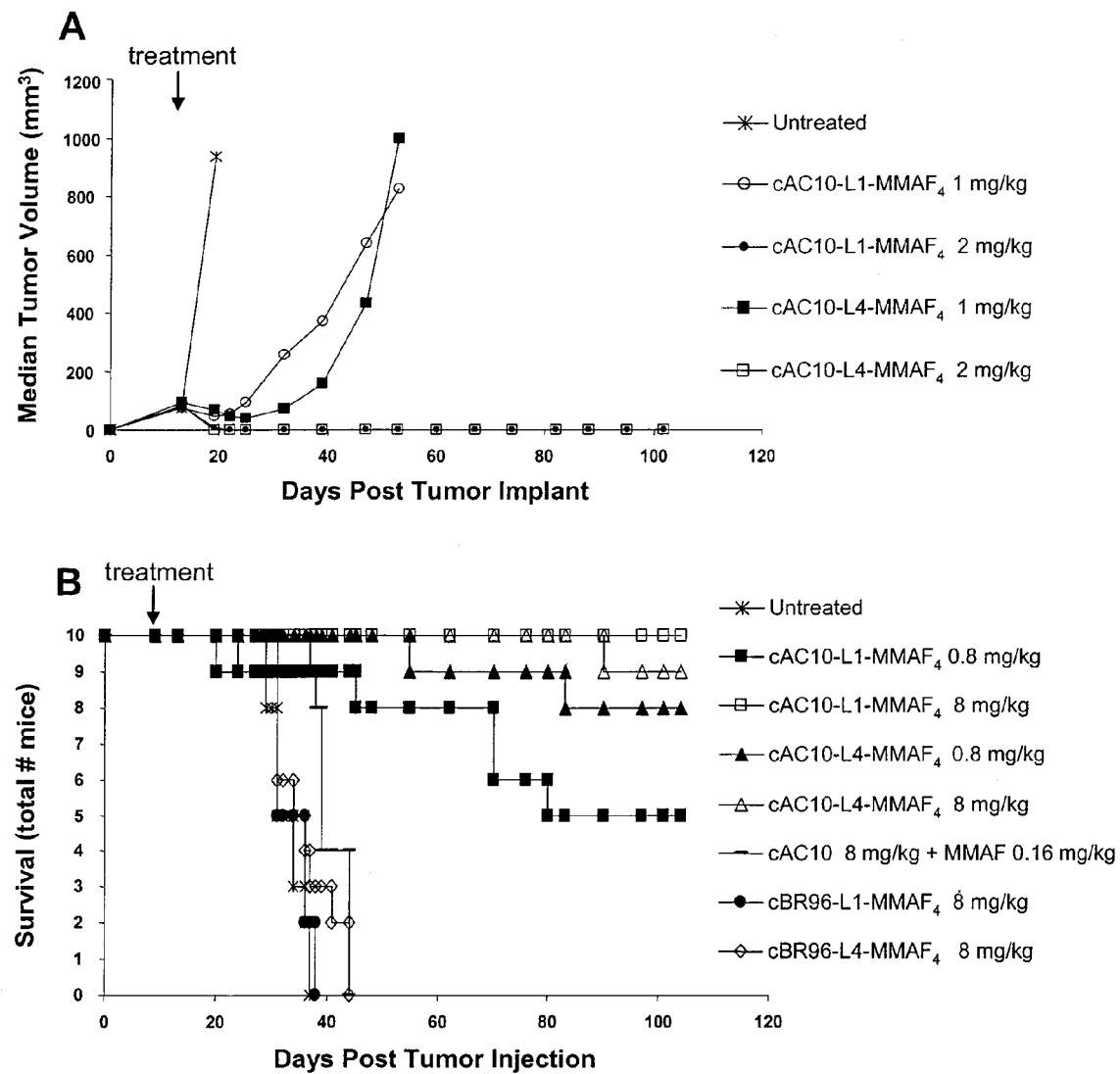
FIG. 4. In vivo therapeutic efficacy of the MMAF drug conjugates in SCID mice. (A) Groups of mice (6/group) with subcutaneous Karpas 299 human ALCL tumors (CD30$^+$) of approximately 100 mm$^3$ average in size were treated with anti-CD30 antibody-linker-drug conjugate, cAC10-L1-MMAF$_4$ or cAC10-L4-MMAF$_4$, at 1 mg and 2 mg mAb component/kg. (B) Groups of mice (5/group) with disseminated Karpas 299 ALCL tumor model (CD30$^+$, Lewis Y negative) were treated on day 9 after tumor injection with an anti-CD30 antibody-linker-drug conjugate, cAC10-L1-MMAF$_4$ or cAC10-L4-MMAF$_4$, the antibody cAC10 in combination with unconjugated MMAF; or an anti-Lewis Y antigen antibody-linker-drug conjugate, cBR96-L1-MMAF$_4$, or cBR96-L4-MMAF$_4$, at the doses indicated.

The therapeutic effects of the ADCs were determined in nude mice with subcutaneous or disseminated Karpas 299 tumors. In animals with subcutaneous tumors, significant antitumor effects were obtained with a single injection of either cAC10-L1-MMAF$_4$ or cAC10-L4-MMAF$_4$, which were indistinguishably potent and active (FIG. 4A). Nearly all animals that received single ADC injections at 2 mg antibody component/kg body weight were cured. In lowering the dose to 1 mg/kg, efficacy for both ADCs, dropped off in an apparently equal manner. At this dose, there were still 2 of 6 and 3 of 6 animals cured with the cAC10-L1-MMAF$_4$ and cAC10-L4-MMAF$_4$ ADCs, respectively.

In order to establish disseminated tumors, Karpas 299 cells were injected intravenously, and allowed to distribute and become established before therapy was initiated 9 days later. In the absence of any treatment, all of the animals succumbed to disseminated disease by day 45. A single administration with either cAC10-L1-MMAF$_4$ or cAC10-L4-MMAF$_4$ was sufficient to cure most of the animals, with a slight dose response between 0.8 mg/kg and 8 mg/kg. The differences between the L1 and L4 linkers were not significant in this tumor model. One of the noteworthy findings in this experiment was the level of specificity. The non-binding control ADCs, cBR96-L1-MMAF$_4$ and cBR96-L1-MMAF$_4$ were inactive, even at 8 mg/kg, which is 10-times the effective dose of the corresponding cAC10 ADCs. Thus, the MMAF conjugates exhibit pronounced activity at very well tolerated doses, and are highly immunologically specific. Furthermore, the therapeutic window of cAC10-L4-MMAF$_4$ is measurably greater than that of cAC10-L1-MMAF$_4$, indicating that the linker technology plays a critical role in the design of effective ADCs that can be safely administered.

Discussion

ADCs comprised of MMAF have distinct properties as compared with those composed of other drugs. The activities of MMAF are potentiated an average of 2,200 fold when the drug is attached through the L1 linker to cAC10, a mAb that is efficiently taken up within the lysosomes of target cells (Table 9). This study describes the activity of cAC10-L4-MMAF$_4$, an ADC that has no built-in provision for drug release. Purified human enzymes that were tested were unable to facilitate release of MMAF or any identifiable MMAF fragments, yet cAC10-L4-MMAF$_4$ is highly potent, both in vitro and in vivo. The mechanism of drug release may involve degradation of the mAb, based on the identification of the cysteine adduct of L4-MMAF.

The data in Table 10 also demonstrate that the various linkers within the MMAF ADC family provide a range of cytotoxic activities. The fact that cAC10-L2-MMAF$_4$ was inactive suggests that the released agent from the L2-MMAF ADC is highly attenuated in activity. The cAC10-L4-MMAF$_4$ was used for further work rather than cAC10-L3-MMAF$_4$, since the PABC group in the L3 linker is hydrophobic and apparently unnecessary for activity.

The objective of the study with various linkers was to determine if the mode of drug release could affect ADC therapeutic index. cAC10-L4-MMAF$_4$ differed from cAC10-L1-MMAF$_4$ by an average of only 2-fold on a large panel of hematologic cell lines (Table 9) in spite of the fact that L1 linker cleavage is quite facile through enzymes such as cathepsin B, while drug release through the L4 linker requires antibody degradation. This observation provided the basis for in vivo experiments, since it was anticipated that the different pathways required for drug elimination could strongly influence the therapeutic windows of the ADCs. Indeed, it was found that cAC10-L4-MMAF$_4$ was tolerated at significantly higher doses in rodents than cAC10-L1-MMAF$_4$, but was equally efficacious in vivo. These results reported herein suggest that the therapeutic window is increased by at least 3-fold through the L4 linker system.

TABLE 10

In Vitro Cytotoxicity of Drug-Linker Combinations

| Conjugate | Target Antigen | IC$_{50}$ (ng/mL) in Karpas 299 cells[a] |
|---|---|---|
| cAC10-L1-MMAF$_4$ | CD30 | 1.2 |
| cAC10-L2-MMAF$_4$ | CD30 | >1500 |
| cAC10-L3-MMAF$_4$ | CD30 | 2.2 |
| cAC10-L4-MMAF$_4$ | CD30 | 2.6 |
| cAC10-L1-MMAE$_8$ | CD30 | 3.6 |
| cAC10-L4-MMAE$_8$ | CD30 | >1000 |
| cBR96-L1-MMAF$_4$ | Lewis Y | >1000 |
| cBR96-L4-MMAF$_4$ | Lewis Y | >1000 |

[a] Karpas 299 cells are CD30 positive, Lewis Y negative. Cytotoxicity was measured as indicated in Table 8.

Deposit of Hybridoma

Hybridoma S2C6, secreting native monoclonal antibody S2C6, was deposited on May 25, 1999, with the American Type Culture Collection (ATCC), 10801 University Boulevard, Manassass, Va. 20110-2209, under the provisions of the Budapest Treaty on the International Recognition of the Deposit of Microorganisms for the Purpose of Patent Procedures, and assigned accession number PTA-110.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Various references, including patent applications, patents, and scientific publications, are cited herein, the disclosures of each of which is incorporated herein by reference in its entirety.

What is claimed is:
1. A purified compound having the formula:
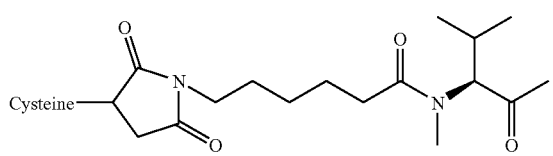
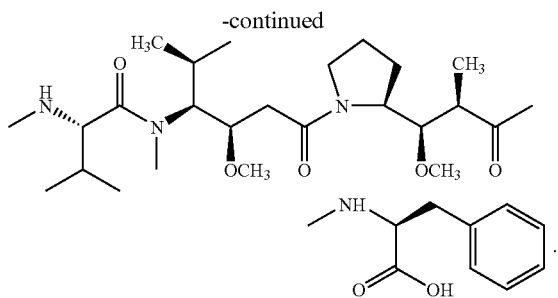
* * * * *

UNITED STATES PATENT AND TRADEMARK OFFICE
CERTIFICATE OF CORRECTION

| | | |
|---|---|---|
| PATENT NO. | : 7,750,116 B1 | Page 1 of 1 |
| APPLICATION NO. | : 11/677029 | |
| DATED | : July 6, 2010 | |
| INVENTOR(S) | : Doronina et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 314 days.

Signed and Sealed this
Fifteenth Day of February, 2011

David J. Kappos
*Director of the United States Patent and Trademark Office*

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

```
<400> SEQUENCE: 1
Gly Ser Val Glu
1
```